United States Patent
Broughton et al.

(10) Patent No.: US 6,262,103 B1
(45) Date of Patent: Jul. 17, 2001

(54) THIENYCYCLOHEXANONE DERIVATIVES AS LIGANDS OF THE GABA$_A$ α5 RECEPTOR SUBTYPE

(75) Inventors: Howard Barff Broughton, Harlow; Mark Stewart Chambers, Puckeridge; Sarah Christine Hobbs, Great Dunmow; Angus Murray MacLeod, Bishop Stortford; Austin John Reeve, Great Dunmow, all of (GB)

(73) Assignee: Merck Sharp & Dohme Limited, Hoddesdon (GB)

( * ) Notice: Subject to any disclaimer, the term of this patent is extended or adjusted under 35 U.S.C. 154(b) by 0 days.

(21) Appl. No.: 09/284,591

(22) PCT Filed: Oct. 28, 1997

(86) PCT No.: PCT/GB97/02970

§ 371 Date: Apr. 16, 1999

§ 102(e) Date: Apr. 16, 1999

(87) PCT Pub. No.: WO98/18792

PCT Pub. Date: May 7, 1998

(30) Foreign Application Priority Data

Oct. 28, 1996 (GB) .................................................. 9622370

(51) Int. Cl.$^7$ ..................... A61K 31/4155; C07D 409/04
(52) U.S. Cl. .................. 514/406; 548/364.4; 548/311.4; 548/253; 548/201; 548/130; 548/131; 546/281.1; 544/333; 544/405; 514/397; 514/382; 514/337; 514/256; 514/253
(58) Field of Search ..................................... 514/253, 255, 514/256, 337, 361, 378, 364, 365, 382, 397, 406, 422; 544/333, 405; 546/281.1; 548/130, 131, 201, 253, 364.4, 311.4, 247, 525

(56) References Cited

FOREIGN PATENT DOCUMENTS

| WO 95/11885 | 5/1995 | (WO) |
| WO 96/16954 | 6/1996 | (WO) |
| WO 96/26929 | 9/1996 | (WO) |
| WO 96/33194 | 10/1996 | (WO) |

OTHER PUBLICATIONS

A. Michiel van Rhee, et al., Tetrahydrobenzothiophenone Derivatives as a Novel Class of Adenosine Receptor Antagonists, J. Med. Chem., 1996, 39, pp. 398–406.

Chemical Abstracts, "Synthesis of new 3–methylthio–4,5,6, 7–tetrahydrobenzo[c]thiophene–4–ones" vol. 123, No. 17, Abstract No. 227923K (1995) p. 1164.

PCT International Search Report, Jan. 26, 1998.

*Primary Examiner*—Charanjits S. Aulakh
(74) *Attorney, Agent, or Firm*—Shu Muk Lee; P. L. Durette; David L. Rose

(57) ABSTRACT

A pharamceutical composition comprises a compound of formula (I) or a pharmaceutically acceptable salt thereof, wherein A is $C_{1-6}$alkyl, $C_{2-6}$alkenyl, $C_{2-6}$-alkynyl, $C_{3-6}$-cycloalkyl, aryl$C_{1-6}$alkyl, aryl, $S(O)_pR^1$.

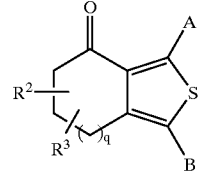

(I)

15 Claims, No Drawings

THIENYCYCLOHEXANONE DERIVATIVES AS LIGANDS OF THE GABA$_A$ α5 RECEPTOR SUBTYPE

This application is a 371 of PCT/GB97/02970 Oct. 29, 1997 now WO98/18792 May 7, 1998.

The present invention relates to pharmaceutical compositions comprising substituted thienylcylohexanone derivatives, to their use in therapy and to novel compounds. More particularly, this invention is concerned with substituted derivatives which are ligands for GABA$_A$ receptors, in particular for GABA$_A$ α5 receptors and are therefore useful in therapy particularly where cognition enhancement is required.

Receptors for the major inhibitory neurotransmitter, gamma-aminobutyric acid (GABA), are divided into two main classes: (1) GABA$_A$ receptors which are members of the ligand-gated ion channel superfamily; and (2) GABA$_B$ receptors, which maybe members of the G-protein linked receptor superfamily. Since the first cDNAs encoding individual GABA$_A$ receptor subunits were cloned the number of known members of the mammalian family has grown to thirteen (six α subunits, three β subunits, three γ subunits and one δ subunit). It may be that further subunits remain to be discovered; however, none has been reported since 1993.

Although knowledge of the diversity of the GABA$_A$ receptor gene family represents a huge step forward in our understanding of this ligand-gated ion channel, inside into the extent of subtype diversity is still at an early stage. It has been indicated that an α subunit, a β subunit and a γ subunit constitute the minimum requirement for forming a fully functional GABA$_A$ receptor expressed by transiently transfecting cDNAs into cells. As indicated above, a δ subunit also exists, but is apparently uncommon in the native receptor.

Studies of receptor size and visualisation by electron microscopy conclude that, like other members of the ligand-gated ion channel family, the native GABA$_A$ receptor exists in pentameric form. The selection of at least one α one β and one γ subunit from a repertoire of thirteen allows for the possible existence of more than 10,000 pentameric subunit combinations. Moreover, this calculation overlooks the additional permutations that would be possible if the arrangement of subunits around the ion channel had no constraints (i.e., there could be 120 possible variants for a receptor composed of five different subunits).

Receptor subtype assemblies which do exist include α1β2γ2, α2β2/3γ2, α3βγ2/3, α2βγ1, α5β3γ2/3, α6βγ2, α6βδ and α4βδ. Subtype assemblies containing an α1 subunit are present in most areas of the brain and account for over 40% of GABA$_A$ receptors in the rat. Subtype assemblies containing α2 and α3 subunits respectively account for about 25% and 17% of GABA$_A$ receptors in the rat. Subtype assemblies containing an α5 subunit are primarily hippocampal and represent about 4% of receptors in the rat.

A characteristic property of some GABA$_A$ receptors is the presence of a number of modulatory sites, of which the most explored is the benzodiazepine (BZ) binding site through which anxiolytic drugs such as diazepam and temazepam exert their effect. Before the cloning of the GABA$_A$ receptor gene family, the benzodiazepine binding site was historically subdivided into two subtypes, BZ1 and BZ2, on the basis of radioligand binding studies. The BA1 subtype has been shown to be pharmacologically equivalent to a GABA$_A$ receptor comprising the α1 subunit in combination with β2 and γ2. This is the most abundant GABA$_A$ receptor subtype, representing almost half of all GABA$_A$ receptors in the brain.

Two other major populations are the α2βγ2 and α3βγ2/3 subtypes. Together these constitute approximately a further 35% of the total GABA$_A$ receptor repertoire. Pharmacologically this combination appears to be equivalent to the BZ2 subtype as defined previously by radioligand binding, although the BZ2 subtype may also include certain α5-containing subtype assemblies. The physiological role of these subtypes has hitherto been unclear because no sufficiently selective agonists or antagonists were known.

It is now believed that agents acting as BZ agonists at α1βγ2, α2βγ2 or α3βγ2 subunits will possess desirable anxiolytic properties. The α1-selective GABA$_A$ receptor agonists alpidem and zolpidem are clinically prescribed as hyphotic agents, suggesting that at least some of the sedation associated with known anxiolytic drugs which act at the BZ1 binding site is mediated through GABA$_A$ receptors containing the α1 subunit. Accordingly, it is considered that GABA$_A$ receptor agonists which bind more effectively to the α2 and/or α3 subunit than to α1 will be effective in the treatment of anxiety with a reduced propensity to cause sedation. Also, agents which are antagonists or inverse agonists at α1 might be employed to reverse sedation or hypnosis caused by α1 agonists.

A number of dementing illnesses such as Alzheimer's disease are characterised by a progressive deterioration in cognition in the sufferer. It would clearly be desirable to enhance cognition in subjects desirous of such treatment, for example for subjects suffering from a dementing illness. It is believed this can be done utilising compounds which are ligands for the GABA$_A$ α5 receptor subtype.

WO-A-9616954 mentions three thienylcyclohexanone derivatives substituted by substituted arylaminocarbonyl on the thiophene ring as fungicides.

Van Rhee et al., *J. Med. Chem.*, 1996, 39, 398–406 discloses related compounds as adenosine receptor antagonists which differ in having an ester group on the thiophene ring.

The present invention provides a pharmaceutical composition comprising a compound of formula (I) or a pharmaceutically acceptable salt thereof:

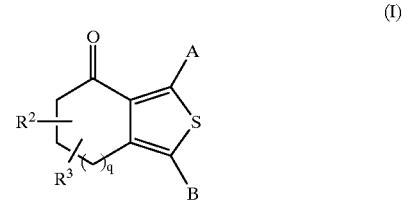

where A is $C_{1-6}$alkyl, $C_{2-6}$alkenyl, $C_{2-6}$alkylnyl, $C_{3-6}$cycloalkyl, aryl$C_{1-6}$alkyl, aryl, $S(O)_pR^1$, $OR^1$ or $NR^1R^{14}$;

B is a 5-membered ring having one or two unsaturations containing 1, 2, 3 or 4 heteroatoms chosen from O, N and S provided that not more than one heteroatoms is other than N, or a 6-membered aromatic ring containing 1, 2, 3 or 4 nitrogen atoms, which ring is optionally substituted by one or more substituents independently chosen from: $C_{1-6}$alkyl; $C_{1-6}$haloalkyl; halogen; $S(O)_pR^4$; $COR^5$; and aryl or aryl $C_{1-6}$alkyl wherein the aryl ring is optionally substituted by one, two or three substituents independently chosen from halogen, $CF_3$, $OCH_3$, nitro and cyano;

$R^1$ is hydrogen; $C_{1-6}$-alkyl;, $C_{2-6}$alkenyl, $C_{2-6}$alkynyl, $C_{3-6}$cycloalkyl or $C_{3-6}$cycloalkenyl each of which is optionally substituted by amino, $C_{1-6}$-alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom, aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$ cycloalkyl group;

$R^4$ is hydrogen, $C_{1-8}$alkyl, $C_{2-8}$alkenyl, $C_{2-8}$alkynyl, aryl or $CH_2(CO)_m NR^8 R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{10}$ is hydrogen, hydroxy, $C_{1-6}$alkoxy, $C_{2-6}$alkenyloxy or $C_{2-6}$alkynyloxy;

$R^{11}$ is $C_{1-6}$alkyl, $C_{2-6}$alkenyl, $C_{2-6}$alkynyl, $C_{1-6}$haloalkyl, $C_{2-6}$haloalkenyl or $C_{2-6}$haloalkynyl;

$R^{12}$ and $R^{13}$ are individually hydrogen, $C_{1-6}$alkyl, $C_{2-6}$alkenyl, $C_{2-6}$alkynyl or $C_{3-8}$cycloalkyl or $R^{12}$ and $R^{13}$, together with the nitrogen atom to which they are attached, form a saturated 4 to 8 membered ring optionally containing an oxygen atom or a further nitrogen atom as a ring member, the further nitrogen atom being unsubstituted or substituted by $C_{1-4}$alkyl, $C_{2-4}$alkenyl or $C_{2-4}$alkynyl;

$R^{14}$ is hydrogen or $C_{1-6}$alkyl;

L is a bond or an unbranched, saturated or monounsaturated hydrocarbon chain having 1–6 carbon atoms;

m is zero or 1;

n is 1 or 2;

p is zero, 1 or 2;

q is 1 or 2; and r is 0, 1 or 2;

and a pharmaceutically acceptable excipient.

B is preferably a 5- or 6-membered optionally substituted aromatic ring.

Thus when B is an aromatic ring it may be a thiazole, pyrazole, pyrimidine, tetrazole, triazole, oxadiazole, oxazole, pyridine, imidazole or pyrazine which is unsubstituted or substituted by $C_{1-6}$alkyl, halogen, $SR^4$, $COR^5$ or benzyl optionally substituted by halogen. When B is a 5- and 6-membered ring having one unsaturation it is preferably oxazolidinyl or imidazolyinyl optionally substituted by halogen or $C_{1-4}$alkyl.

Particularly embodiments of B are (1-phenylsulphonyl) pyrazol-3-yl, 1-acetylpyrazol-3-yl, (3-ethoxycarbonyl) isoxazol-5-yl, (3-isopropyl)-1,2,4-oxaidazol-5-yl, imidazolin-2-yl, pyrazol-4-yl, 2-methyl-1,3,4-oxadiazol-5-yl, oxazolidin-2-yl, 2-methyltetrazol-5-yl, pyrazol-3-yl, 2-propyltetrazol-5-yl, thiazol-2-yl, 4-methyl-1,2,4-triazol-3-yl, (4-ethoxycarbonyl)thiazol-2-yl, (4-trifluoromethyl) thiazol-2-yl, (4-acetyl)thiazol-2-yl, (4-methyl)thiazol-2-yl, pyrrol-2-yl, pyrid-2-yl, 3-methyl-1,2,4-oxadiazol-5-yl, 4-benzyl-1,2,4-triazol-3-yl, 1-methyl-1,2,4-triazol-3-yl, oxazol-2-yl, pyrazin-2-yl, pyrimidin-5-yl, 3-(N-methylaminocarbonyl)thiazol-2-yl, thiazol-5-yl, isoxazol-5-yl, pyrid-3-yl, pyrid-4-yl, 1,3,4-oxadiazol-5-yl and 1-methylsulphonylpyrazol-3-yl.

$R^1$ is preferably $C_{1-6}$alkyl, $C_{2-6}$alkenyl or $C_{3-6}$cycloalkyl each of which is optionally substituted by amino, di($C_{1-6}$alkyl)amino, hydroxy, $C_{1-6}$alkoxy $C_{1-6}$alkylaminocarbonyl or one, two or three halogen atoms; aryl or aryl$C_{1-6}$alkyl optionally substituted on the aryl ring by halogen, $C_{1-6}$alkylcarbonylamino or $C_{1-6}$alkoxy; or a five-membered aromatic ring containing 1, 2 or 3 heteroatoms chosen from O, N and S provided that not more than one heteroatom is other than N, or a six-membered aromatic ring containing 1 or 2 nitrogen atoms, which ring is optionally substituted by halogen, $C_{1-6}$alkoxy, $C_{1-6}$alkylthio, aryl or $C_{1-6}$alkyl.

More preferably $R^1$ is $C_{1-6}$alkyl, $C_{1-4}$alkenyl, or $C_{4-6}$cycloalkyl each of which is optionally substituted by di($C_{1-4}$alkylamino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio.

When A is not $S(O)_p R^1$, $OR^1$ or $NR^1R^{14}$ it is preferably $C_{1-6}$alkyl, $C_{2-6}$-alkenyl or $C_{3-6}$cycloalkyl.

When A is $OR^1$, $R^1$ is generally $C_{1-6}$alkyl optionally substituted by $C_{1-4}$alkoxy, $C_{3-6}$cycloalkyl or aryl.

Particularly embodiments of A are phenyl, cyclohexyl, 2-methylprop-1-enyl, methylthio, ethyl, isopropyl, propyl, cyclobutyl, but-3-enyl, cyclopropyl, methanesulphonyl, methyl, henzyl, methanesulphinyl, (1,1-dimethylethyl)thio, pentylthio, (4-methyl-1,2,4-triazol-3-yl)thio, hexylthio, benzylamino, (3-imidazol-1-ylpropyl)amino, (pyrid-2-yl) amino, 2-methylprop-1-yl, [3-(4-methylpiperazin-1-yl) propyl]amino, methylamino, (2-hydroxyethyl)amino, azetidin-1-yl, tert-butylamino, isopropylthio, (2-hydroxyethyl)thio, methoxy, dimethylamino, cyclobutoxy, phenoxy, butylthio, (3-chloropropyl)thio, (2-phenylethyl)thio, propylthio, (2-methylbutyl)thio, (2,2,2-trifluoroethyl)thio, (1-methylpropyl)thio, (4-chlorophenyl) thio, (3-fluorophenyl)thio, (4-acetylaminophenyl)thio, (4-methoxyphenyl)thio, (1-methylimidazol-2-yl)thio, (thiophen-2-yl)thio, (imidazol-2-yl)thio, (4-phenylthiazol-2-yl)thio, (1,2,4-triazol-3-yl)thio, (5-methyl-1,3,4-thiadiazol-2-yl)thio, (5-methylthio-1,3,4-thiadiazol-2-yl)thio, benzylthio, cyclopentylthio, (2-methylpropylthio, (furan-2-ylmethyl)thio, (2-hydroxy-1-methylpropyl)thio (2,3-dihydroxypropyl)thio, (2-hydroxypropyl)thio, ((N-methylaminocarbonyl)methyl)thio, (pyrid-4-yl)thio, (pyrimidin-2-yl)thio, (thiazol-2-yl)thio, prop-2-enylthio, (pyrid-2-yl)thio, ethylthio, phenylthio, (N,N-dimethyl-2-aminoethyl)thio, (2-methoxyethyl)thio, (furan-2-ylmethyl) amino, (2-methylpropyl)amino, propylamino, (2-methoxyethyl)amino, cyclopropylamino, isopropylamino, ethylamino cyclobutylamino and isopropoxy.

$R^2$ and $R^3$ are preferably independently chosen from hydrogen and methyl or are attached to the same carbon atom and together with that atom form a $C_{3-6}$cycloalkyl group, and are most preferably both methyl. Preferably $R^2$ and $R^3$ are geminal to each other, preferably at the 6-position, i.e. beta to the carbonyl group in formula I.

$R^4$ may be hydrogen, $C_{1-4}$alkyl, $C_{2-4}$alkyl, $C_{2-4}$alkenyl, $C_{2-4}$alkynyl, aryl or $CH_2(CO)_mNR^8R^9$, $R^4$ is preferably hydrogen, $C_{1-4}$alkyl or $CH_2(CO)_mNR^8R^9$, more preferably hydrogen, methyl or $CH_2CONR^8R^9$ and most preferably methyl or $CH_2CONR^8R^9$.

$R^5$ is preferably methyl, ethoxy, ethoxy or $NR^6R^7$ and most preferably methyl, ethoxy or $NR^6R^7$.

$R^6$ may be hydrogen, $C_{1-4}$alkyl, $C_{2-4}$alkenyl, $C_{2-4}$alkynyl, aryl or $CH_2(CO)_mNR^8R^9$. $R^6$ is preferably hydrogen or $C_{1-4}$alkyl and most preferably hydrogen.

$R^7$ is preferably phenyl unsubstituted or substituted by halogen, nitro or cyano, more preferably optionally substituted by halogen, such as chlorine.

$R^8$ is preferably hydrogen or $C_{1-6}$alkyl and most preferably hydrogen.

$R^9$ is preferably $C_{1-6}$alkyl or phenyl unsubstituted or substituted by one, two or three substituents independently chosen from halogen, nitro and cyano, more preferably $C_{1-6}$alkyl or phenyl optionally substituted by one or two substituents independently chosen from halogen and nitro and most preferably tert-butyl or phenyl optionally substituted with one or two substituents chosen from chlorine and nitro, such as 4-chlorophenyl.

$R^{10}$ is generally hydrogen, hydroxy or $C_{1-4}$alkoxy and most preferably hydrogen.

$R^{11}$ is generally $C_{1-4}$alkyl or $C_{1-4}$haloalkyl, more particularly $C_{1-1}$alkyl or $C_{1-4}$fluoroalkyl, and most preferably $CF_3$.

$R^{12}$ and $R^{13}$ are preferably independently hydrogen, $C_{1-4}$alkyl or $C_{3-6}$cycloalkyl or $R^{12}$ and $R^{13}$, together with the nitrogen atom to which they are attached, form a saturated 5 to 7-membered ring optionally containing an oxygen atom or a further nitrogen atom at the 4-position the further nitrogen atom being unsubstituted or substituted with $C_{1-4}$alkyl. More particularly $R^{12}$ and $R^{13}$ are independently hydrogen, methyl or cyclohexyl or $R^{12}$ and $R^{13}$ together with the nitrogen atom to which they are attached form a piperidine, piperazine or morpholine ring the further nitrogen atom in the piperazine ring being optionally substituted by methyl.

$R^{14}$ is generally hydrogen or $C_{1-4}$alkyl and most preferably hydrogen.

L is preferably a bond or an unbranched unsaturated hydrocarbon chain having 1 to 4 carbon atoms, more particularly L is a bond or $-CH=CH-$. Generally L is a bond.

m is preferably 1.
n is preferably 1.
p is preferably zero or two, most preferably zero.
q is preferably 1.
r is preferably 1.

A subclass of compositions according to the present invention comprises a compound of formula (I) or a pharmaceutically acceptable salt thereof in which:

A is $SR^1$;

B is a nitrogen containing aromatic ring which is 5-membered and contains 1, 2, 3, or 4 heteroatoms chosen from O, N and S provided that not more than one heteroatom is other than N, or is 6-membered and contains 1, 2, 3 or 4 nitrogen atoms, which ring is optionally substituted by $C_{1-6}$alkyl, halogen, $SR^4$, $COR^5$ or benzyl optionally substituted by one or two substituents independently chosen from halogen, nitro and cyano;

$R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiodiazole, each of which is unsubstituted or substituted by $C_{1-4}$alkyl, phenyl, fluorine or $C_{1-4}$alkylthio;

$R^2$ and $R^3$ are independently chosen from hydrogen and methyl;

$R^4$ is hydrogen, methyl or $CH_2CONR^8R^9$;

$R^5$ is methyl, methoxy, ethoxy or $NR^6R^7$;

$R^6$ is hydrogen or $C_{1-4}$alkyl;

$R^7$ is phenyl unsubstituted or substituted by halogen, nitro or cyano;

$R^8$ is hydrogen or $C_{1-6}$alkyl;

$R^9$ is $C_{1-6}$alkyl or phenyl optionally substituted by one or two substituents independently chosen from halogen or nitro;

$R^{10}$ is hydrogen;

$R^{11}$ is $C_{1-4}$alkyl or $C_{1-4}$fluoroalkyl;

$R^{12}$ and $R^{13}$ are independently hydrogen, methyl or cyclohexyl or $R^{12}$ and $R^{13}$ together with the nitrogen atom to which they are attached form a piperidine, piperazine or morpholine ring, the further nitrogen atom in the piperazine ring being optionally substituted by methyl;

$R^{14}$ is hydrogen or $C_{1-4}$alkyl;

L is a bond or $-CH=CH-$;

p is zero; and q is 1;

and a pharmaceutically acceptable excipient.

The preferred definitions of each substituent hereinbefore recited apply mutotis mutandis to this subclass.

The present invention also provides pharmaceutical composition comprising a compound of formula (I') or a pharmaceutically acceptable salt thereof:

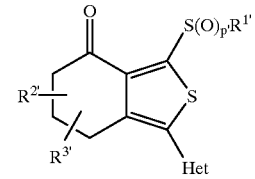

(I')

where Het is a 5-membered aromatic ring containing 1, 2, 3 or 4 heteroatoms chosen from O, N and S provided that not more than one heteroatom is other than N, or a 6-membered aromatic ring containing 1, 2, 3 or 4 nitrogen atoms, which ring is optionally substituted by one or more substituents independently chosen from $C_{1-6}$alkyl; halogen; $SR^{4'}$; $COR^{5'}$; and phenyl optionally substituted by one, two or three substituents independently chosen from halogen, $CF_3$, $OCH_3$, nitro and cyano, $R^{1'}$ is hydrogen, $C_{1-6}$-alkyl, $C_{3-6}$cycloalkyl, $C_{3-6}$cycloalkynyl $C_{2-6}$alkenyl, $C_{2-6}$alkynyl, aryl$C_{1-}$ $_6$alkyl, arylC$_{2-6}$alkenyl or arylC$_{2-6}$alkynyl optionally substituted on the aryl ring by halogen, nitro or cyano; thiophene or pyridine;

R$^{2'}$ and R$^{3'}$ are independently hydrogen or C$_{1-6}$alkyl;

R$^{4'}$ is C$_{1-4}$alkyl, C$_{2-4}$alkenyl, C$_{2-4}$alkylnyl or CH$_2$(CO)$_{m'}$-NR$^{5'}$R$^{9'}$;

R$^{5'}$ is NR$^{6'}$R$^{7'}$, C$_{1-6}$alkyl or C$_{1-6}$alkoxy;

R$^{6'}$ is hydrogen or is independently as defined for R$^{4'}$;

R$^{7'}$ is aryl optionally substituted by halogen, nitro or cyano;

R$^{8'}$ is independently as defined for R$^{1'}$;

R$^{9'}$ is C$_{1-6}$alkyl; C$_{2-6}$alkenyl; C$_{2-6}$alkynyl; or phenyl optionally substituted by one, two or three substituents independently chosen from halogen, CF$_3$, OCH$_3$, nitro and cyano;

m' is zero or 1; and p' is zero, 1 or 2;

and a pharmaceutically acceptable excipient.

R$^{1'}$ is preferably C$_{1-6}$alkyl, arylC$_{1-6}$alkyl wherein the aryl ring is unsubstituted or substituted by halogen, nitro or cyano, thiophene or pyridine; more preferably C$_{1-6}$alkyl, phenylC$_{1-6}$alkyl optionally substituted on the phenyl ring by halogen, nitro or cyano, thiophene or pyridine; more preferably still C$_{1-6}$alkyl and most preferably methyl.

R$^{2'}$ and R$^{3'}$ are preferably independently chosen from hydrogen and methyl and are most preferably both methyl. Preferably R$^{2'}$ and R$^{4'}$ are geminal to each other, preferably at the 6-position.

R$^{4'}$ is preferably hydrogen, C$_{1-4}$alkyl or CH$_2$(CO)$_{m'}$—NR$^{8'}$R$^{9'}$, more preferably hydrogen, methyl or CH$_2$CONR$^{8'}$R$^{9'}$ and most preferably hydrogen or methyl.

R$^{5'}$ is preferably methyl, methoxy or NR$^{6'}$R$^{7'}$ and most preferably methyl or NR$^{6'}$R$^{7'}$.

R$^{6'}$ is preferably hydrogen or C$_{1-4}$alkyl and most preferably hydrogen.

R$^{7'}$ is preferably phenyl unsubstituted or substituted by halogen, nitro or cyano, more preferably optionally substituted by halogen, such as chlorine.

R$^{8'}$ is preferably hydrogen or C$_{1-6}$alkyl and most preferably hydrogen.

R$^{9'}$ is preferably C$_{1-6}$alkyl or phenyl unsubstituted or substituted by one, two or three substituents independently chosen from halogen, nitro and cyano, more preferably C$_{1-6}$alkyl or phenyl optionally substituted by one or two substituents independently chosen from halogen and nitro and most preferably tert-butyl or phenyl optionally substituted with one or two substituents chosen from chlorine and nitro, such as 4-chlorophenyl.

m' is preferably 1.

p' is preferably zero.

Het is preferably a nitrogen containing ring such as a pyrimidine or pyrazole. Het may be unsubstituted. Het may be substituted. When Het is a pyrimidine it is preferably attached to the rest of the compound via the 4-position and when a pyrazole via the 3-position. When Het is a pyrimidine it is preferably optionally substituted at the 2-position and when a pyrazole at 1- or 4-position.

Het is preferably unsubstituted or substituted by one substituent. When Het is a pyrimidine it is preferably optionally substituted by a group SR$^{4'}$ where R$^{4'}$ is as defined in any of the definitions of R$^{4'}$ above. When Het is a pyrazole it is preferably optionally substituted at the 4-position by a halogen such as bromine or by a group COR$^{5'}$ where R$^{5'}$ is as defined above. Het is optionally not a thiazole.

A subclass of compositions according to the present invention comprises a compound of formula (I') in which:

Het is a nitrogen containing aromatic ring which is 5-membered and contains 1, 2, 3 or 4 heteroatoms chosen from O, N and S provided that not more than one heteroatom is other than N, or is 6-membered and contains 1, 2, 3 or 4 nitrogen atoms, which ring is optionally substituted by C$_{1-6}$alkyl, halogen, SR$^{4'}$, COR$^{5'}$ or phenyl optionally substituted by one or two substituents independently chosen from halogen, nitro and cyano;

R$^{1'}$ is C$_{1-6}$alkyl, arylC$_{1-6}$alkyl, thiophene or pyridine;

R$^{2'}$ and R$^{3'}$ are independently chosen from hydrogen and methyl;

p' is zero; and

R$^{4'}$, R$^{5'}$, R$^{6'}$, R$^{7'}$, R$^{8'}$, R$^{9'}$ and m' are as defined for formula (I');

and a pharmaceutically acceptable excipient.

An alternative subclass of compositions according to the present invention comprises a compound of formula (I') in which:

Het is a nitrogen containing aromatic ring which is 5-membered and contains 1, 2, 3 or 4 heteroatoms chosen from O, N and S provided that not more than one heteroatom is other than N, or is 6-membered and contains 1, 2, 3 or 4 nitrogen atoms, which ring is optionally substituted by halogen, SR$^{4'}$ or COR$^{5'}$;

R$^{1'}$ is C$_{1-6}$alkyl, arylC$_{1-6}$alkyl, thiophene or pyridine;

R$^{2'}$ and R$^{3'}$ are independently chosen from hydrogen and methyl;

R$^{4'}$ is hydrogen or C$_{1-4}$alkyl;

p' is zero; and

R$^{5'}$, R$^{6'}$, R$^{7'}$, R$^{8'}$, R$^{9'}$ and m' are as defined for formula (I');

and a pharmaceutically acceptable excipient.

The preferred definitions of each substituent hereinbefore recited for compound of formula (I') apply mutatis mutandis to both these subclasses.

Specific Examples of compounds which can be used in the compositions of the present invention are:

6,6-dimethyl-3-methylthio-1-(pyrazol-3-yl)-4,5,6,7-tetrahydrobenzo[c]thiophen-4-one;

1-(1-[4-(chlorophenyl)aminocarbonyl]pyrazol-3-yl)-6,6-dimethyl-3-methylthio-4,5,6,7-tetrahydrobenzo[c]thiophen-4-one;

1-(4-bromopyrazol-3-yl)-6,6-dimethyl-3-methylthio-4,5,6,7-tetrahydrobenzo[c]thiophen-4-one;

6,6-dimethyl-3-methylthio-1-(2-methylthiopyrimidin-4-yl)-4,5,6,7-tetrahydrobenzo[c]thiophen-4-one;

6,6-dimethyl-3-methylthio-1-(2-thiopyrimidin-4-yl)-4,5,6,7-tetrahydrobenzo[c]thiophen-4-one;

6,6-dimethyl-3-methylthio-1-[1-(phenylaminocarbonyl)pyrazol-3-yl]-4,5,6,7-tetrahydrobenzo[c]thiophen-4-one;

1-(1-acetylpyrazol-3-yl)-6,6-dimethyl-3-methylthio-4,5,6,7-tetrahydrobenzo[c]thiophen-4-one;

1-[2-([2-chlorophenyl]aminocarbonylmethylthio)pyrimidin-4-yl]-6,6-dimethyl-3-methylthio-4,5,6,7-tetrahydrobenzo[c]thiophen-4-one;

6,6-dimethyl-1-(1-methylpyrazol-3yl)-3-methylthio-4,5,6,7-tetrahydrobenzo[c]thiophen-4-one.

The pharmaceutically acceptable salts of the above compounds can also be used in the compositions of the present invention.

Further specific compounds which can be used in the compositions of the present invention are:

6,6-Dimethyl-1-(2-methyltetrazol-5-yl)-3-methylthio-4,5,6,7-tetrahydrobenzo[c]thiophen-4-one;

6,6-Dimethyl-3-methanesulphinyl-1-(pyrazol-3-yl)-4,5,6,7-tetrahydrobenzo[c]thiophen-4-one;

6,6-Dimethyl-3-ethyl-1-(pyrazol-3-yl)-4,5,6,7-tetrahydrobenzo[c]thiophen-4-one;

6,6-Dimethyl-3-methylthio-1-(2-propyltetrazol-5-yl)-4,5,6,7-tetrahydrobenzo[c]-thiophen-4-one;

6,6-Dimethyl-1-(1-methanesulphonylpyrazol-3-yl)-3-methylthio-4,5,6,7-tetrahydrobenzo[c]thiophen-4-one;

6,6-Dimethyl-3-(2-methylprop-1-yl)-1-(thiazol-2-yl)-4,5,6,7-tetrahydrobenzo[c]thiophen-4-one;

6,6-Dimethyl-3-isopropyl-1-(thiazol-2-yl)-4,5,6,7-tetrahydrobenzo[c]thiophen-4-one;

6,6-Dimethyl-3-propyl-1-(thiazol-2-yl)-4,5,6,7-tetrahydrobenzo[c]thiophen-4-one;

6,6-Dimethyl-3-phenyl-1-(thiazol-2-yl)-4,5,6,7-tetrahydrobenzo[c]thiophen-4-one;

3-Cyclohexyl-6,6-dimethyl-1-(thiazol-2-yl)-4,5,6,7-tetrahydrobenzo[c]thiophen-4-one 3-Cyclobutyl-6,6-dimethyl-1-(thiazol-2-yl)-4,5,6,7-tetrahydrobenzo[c]thiophen-4-one;

3-(But-3-enyl)-6,6-dimethyl-1-(thiazol-2-yl)-4,5,6,7-tetrahydrobenzo[c]thiophen-4-one;

3Cyclopropyl-6,6-dimethyl-1-(thiazol-2-yl)-4,5,6,7-tetrahydrobenzo[c]thiophen-4-one;

6,6-Dimethyl-3-(2-methylprop-1-enyl)-1-(thiazol-2-yl)-4,5,6,7-tetrahydrobenzo[c]thiophen-4-thione;

3-Methylthio-1-(pyrid-2-yl)-4,5,6,7-tetrahydro[c]thiophen-4-one;

6,6-Dimethyl-3-methanesulphonyl-1-(pyrazol-3-yl)-4,5,6,7-tetrahydrobenzo[c]thiophen-4-one;

1-(Thiazol-2-yl)-3,6,6-trimethyl-4,5,6,7-tetrahydrobenzo[c]thiophen-4-one;

3-Benzyl-6,6-dimethyl-1-(thiazol-2-yl)-4,5,6,7-tetrahydrobenzo[c]thiophen-4-one;

6,6-Dimethyl-3-methylthio-1-((1-phenylsulphonyl)pyrazol-3-yl)-4,5,6,7-tetrahydrobenzo[c]thiophen-4-one;

6,6-Dimethyl-3-isopropylthio-1-(2-methyltetrazol-5-yl)-4,5,6,7-tetrahydrobenzo[c]thiophen-4-one;

1-(1-Acetylpyrazol-3-yl)-6,6-dimethyl-3-methanesulphinyl-4,5,6,7-tetrahydrobenzo[c]thiophen-4-one;

6,6-Dimethyl-3-[(2-hydroxyethyl)thio]-1-(thiazol-2-yl)-4,5,6,7-tetrahydrobenzo[c]thiophen-4-one;

6,6-Dimethyl-3-[(1,1-dimethylethyl)thio]-1-(pyrazol-3-yl)-4,5,6,7-tetrahydrobenzo[c]thiophen-4-one;

6,6-Dimethyl-3-methoxy-1-(pyrazol-3-yl)-4,5,6,7-tetrahydrobenzo[c]thiophen-4-one;

6,6-Dimethyl-1-(4-methyl-1,2,4-triazol-3-yl)-3-methylthio-4,5,6,7-tetrahydrobenzo[c]thiophen-4-one;

6,6-Dimethyl-1-((4-ethoxycarbonyl)thiazol-2-yl)-3-methylthio-4,5,6,7-tetrahydrobenzo[c]thiophen-4-one;

6,6-Dimethyl-1-((4-trifluoromethyl)thiazol-2-yl)-3-methylthio-4,5,6,7-tetrahydrobenzo[c]thiophen-4-one;

6,6-Dimethyl-3-methylthio-1-(thiazol-2-yl)-4,5,6,7-tetrahydrobenzo[c]thiophen-4-one;

6,6-Dimethyl-3-dimethylamino-1-((4-ethoxycarbonyl)thiazol-2-yl)-4,5,6,7-tetrahydrobenzo[c]thiophen-4-one;

1-((4-Acetyl)thiazol-2-yl)-6,6-dimethyl-3-methylthio-4,5,6,7-tetrahydrobenzo[c]thiophen-4-one;

6,6-Dimethyl-1-((4-methyl)thiazol-2-yl)-3-methylthio-4,5,6,7-tetrahydrobenzo[c]thiophen-4-one;

6,6-Dimethyl-3-isopropylthio-1-(thiazol-2-yl)-4,5,6,7-tetrahydrobenzo[c]thiophen-4-one;

6,6-Dimethyl-3-methylthio-1-(pyrazol-4-yl)-4,5,6,7-tetrahydrobenzo[c]thiophen-4-one;

6,6-Dimethyl-3-methylthio-1-(pyrrol-2-yl)-4,5,6,7-tetrahydrobenzo[c]thiophen-4-one;

6,6-Dimethyl-3-methylthio-1-(pyrid-2-yl)-4,5,6,7-tetrahydrobenzo[c]thiophen-4-one;

6,6-Dimethyl-3-((2-hydroxyethyl)thio)-1-(pyrid-2-yl)-4,5,6,7-tetrahydrobenzo[c]thiophen-4-one;

3-Methylthio-1-(thiazol-2-yl)-4-oxo-5,6,7,8-tetrahydro-4H-cyclohepta[c]thiophene;

6,6-Dimethyl-3-methylthio-1-(3-methyl-1,2,4-oxadiazol-5-yl)-4,5,6,7-tetrahydrobenzo[c]thiophen-4-one;

6,6-Dimethyl-3-methylthio-1-(3-isopropyl-1,2,4-oxadiazol-5-yl)-4,5,6,7-tetrahydrobenzo[c]thiophen-4-one;

6,6-Dimethyl-1-(4-benzyl-1,2,4-triazol-3-yl)-3-methylthio-4,5,6,7-tetrahydrobenzo[c]thiophen-4-one;

6,6-Dimethyl-3-methylthio-1-(1-methyl-1,2,4-triazol-3-yl)-4,5,6,7-tetrahydrobenzo[c]thiophen-4-one;

6,6-Dimethyl-3-methylthio-1-(oxazolidin-2-yl)-4,5,6,7-tetrahydrobenzo[c]thiophen-4-one;

3-Methylthio-1-(oxazol-2-yl)-4,5,6,7-tetrahydrobenzo[c]thiophen-4-one;

6,6-Dimethyl-3-methylthio-1-(pyrazin-2-yl)-4,5,6,7-tetrahydrobenzo[c]thiophen-4-one;

6,6-Dimethyl-3-methylthio-1-(pyrimidin-5-yl)-4,5,6,7-tetrahydrobenzo[c]thiophen-4-one;

6,6-Dimethyl-1-(imidazolin-2-yl)-3-methylthio-4,5,6,7-tetrahydrobenzo[c]thiophen-4-one;

3-Methylthio-6,6-spirocyclohexyl-1-(thiazol-2-yl)-4,5,6,7-tetrahydrobenzo[c]thiophen-4-one;

6,6-Dimethyl-1-(3-(N-methylaminocarbonyl)thiazol-2-yl)-3-methylthio-4,5,6,7-tetrahydrobenzo[c]thiophen-4-one;

6,6-Dimethyl-3-methylthio-1-(thiazol-5-yl)-4,5,6,7-tetrahydrobenzo[c]thiophen-4-one;

6,6-Dimethyl-3-tert-butylamino)-1-(pyrazol-3-yl)-4,5,6,7-tetrahydrobenzo[c]thiophen-4-one;

3-Cyclobutoxy-6,6-dimethyl-1-(pyrazol-3-yl)-4,5,6,7-tetrahydrobenzo[c]thiophen-4-one;

6,6-Dimethyl-1-[(3-ethoxycarbonyl)isoxazol-5-yl)-3-methylthio-4,5,6,7-tetrahydrobenzo[c]thiophen-4-one;

6,6-Dimethyl-3-phenoxy-1-(pyrazol-3-yl)-4,5,6,7-tetrahydrobenzo[c]thiophen-4-one;

6,6-Dimethyl-3-pentylthio-1-(pyrazol-3-yl)-4,5,6,7-tetrahydrobenzo[c]thiophen-4-one;

3-Butylthio-6,6-dimethyl-1-(pyrazol-3-yl)-4,5,6,7-tetrahydrobenzo[c]thiophen-4-one;

3-[(3-Chloropropyl)thio]-6,6-dimethyl-1-(pyrazol-3-yl)-4,5,6,7-tetrahydrobenzo[c]thiophen-4-one;

6,6-Dimethyl-3-((2-phenylethyl)thio)-1-(pyrazol-3-yl)-4,5,6,7-tetrahydrobenzo[c]thiophen-4-one;

6,6-Dimethyl-3-propylthio-1-(pyrazol-3-yl)-4,5,6,7-tetrahydrobenzo[c]thiophen-4-one;

6,6-Dimethyl-3-((2-methylbutyl)thio)-1-(pyrazol-3-yl)-4,5,6,7-tetrahydrobenzo[c]thiophen-4-one;

6,6-Dimethyl-1-(pyrazol-3-yl)-3-((2,2,2-trifluoroethyl)thio)-4,5,6,7-tetrahydrobenzo[c]thiophen-4-one;

6,6-Dimethyl-3-((1-methylpropyl)thio)-1-(pyrazol-3-yl)-4,5,6,7-tetrahydrobenzo[c]thiophen-4-one;

3-((4-Chlorophenyl)thio)-6,6-dimethyl-1-(pyrazol-3-yl)-4,5,6,7-tetrahydrobenzo[c]thiophen-4-one;

6,6-Dimethyl-3-((3-fluorophenyl)thio)-1-(pyrazol-3-yl)-4,5,6,7-tetrahydrobenzo[c]thiophen-4-one;

3-((4-Acetylaminophenyl)thio)-6,6-dimethyl-1-(pyrazol-3-yl)-4,5,6,7-tetrahydrobenzo[c]thiophen-4-one;

6,6-Dimethyl-3-((4-methoxyphenyl)thio)-1-(pyrazol-3-yl)-4,5,6,7-tetrahydrobenzo[c]thiophen-4-one;

6,6-Dimethyl-3-((1-methylimidazol-2-yl)thio)-1-(pyrazol-3-yl)-4,5,6,7-tetrahydrobenzo[c]thiophen-4-one;

6,6-Dimethyl-3-((thiophen-2-yl)thio)-1-(pyrazol-3-yl)-4,5,6,7-tetrahydrobenzo[c]thiophen-4-one;

6,6-Dimethyl-3-((imidazol-2-yl)thio)-1-(pyrazol-3-yl)-4,5,6,7-tetrahydrobenzo[c]thiophen-4-one;

6,6-Dimethyl-3-((4-phenylthiazol-2-yl)thio)-1-(pyrazol-3-yl)-4,5,6,7-tetrahydrobenzo[c]thiophen-4-one;

6,6-Dimethyl-1-(pyrazol-3-yl)-3-((1,2,4-triazol-3-yl)thio)-4,5,6,7-tetrahydrobenzo[c]thiophen-4-one;

6,6-Dimethyl-3-((5-methyl-1,3,4-thiadiazol-2-yl)thio)-1-(pyrazol-3-yl)-4,5,6,7-tetrahydrobenzo[c]thiophen-4-one;

6,6-Dimethyl-3-((4-methyl-1,2,4-triazol-3-yl)thio)-1-(pyrazol-3-yl)-4,5,6,7-tetrahydrobenzo[c]thiophen-4-one;

6,6-Dimethyl-3-((5-methylthio-1,3,4-thiadiazol-2-yl)thio)-1-(pyrazol-3-yl)-4,5,6,7-tetrahydrobenzo[c]thiophen-4-one;

3-Benzylthio-6,6-dimethyl-1-(pyrazol-3-yl)-4,5,6,7-tetrahydrobenzo[c]thiophen-4-one;

3-Cyclopentylthio-6,6-dimethyl-1-(pyrazol-3-yl)-4,5,6,7-tetrahydrobenzo[c]thiophen-4-one;

6,6-Dimethyl-3-((2-methylpropyl)thio)-1-(pyrazol-3-yl)-4,5,6,7-tetrahydrobenzo[c]thiophen-4-one;

6,6-Dimethyl-3-hexylthio-1-(pyrazol-3-yl)-4,5,6,7-tetrahydrobenzo[c]thiophen-4-one;

6,6-Dimethyl-3-isopropylthio-1-(pyrazol-3-yl)-4,5,6,7-tetrahydrobenzo[c]thiophen-4-one;

6,6-Dimethyl-3-((furan-2-ylmethyl)thio)-1-(pyrazol-3-yl)-4,5,6,7-tetrahydrobenzo[c]thiophen-4-one;

6,6-Dimethyl-3-((2-hydroxy-1-methylpropyl)thio)-1-(pyrazol-3-yl)-4,5,6,7-tetrahydrobenzo[c]thiophen-4-one;

6,6-Dimethyl-3-((2,3-dihydroxypropyl)thio)-1-(pyrazol-3-yl)-4,5,6,7-tetrahydrobenzo[c]thiophen-4-one;

6,6-Dimethyl-3-((2-hydroxypropyl)thio)-1-(pyrazol-3-yl)-4,5,6,7-tetrahydrobenzo[c]thiophen-4-one;

6,6-Dimethyl-3-(((N-methylaminocarbonyl)methyl)thio)-1-(pyrazol-3-yl)-4,5,6,7-tetrahydrobenzo[c]thiophen-4-one;

6,6-Dimethyl-1-(pyrazol-3-yl)-3-((pyrid-4-yl)thio)-4,5,6,7-tetrahydrobenzo[c]thiophen-4-one;

6,6-Dimethyl-1-(pyrazol-3-yl)-3-((pyrimidin-2-yl)thio)-4,5,6,7-tetrahydrobenzo[c]thiophen-4-one;

6,6-Dimethyl-1-(pyrazol-3-yl)-3-((thiazol-2-yl)thio)-4,5,6,7-tetrahydrobenzo[c]thiophen-4-one;

6,6-Dimethyl-3-(prop-2-enylthio)-1-(pyrazol-3-yl)-4,5,6,7-tetrahydrobenzo[c]thiophen-4-one;

6,6-Dimethyl-1-(pyrazol-3-yl)-3-((pyrid-2-yl)thio)-4,5,6,7-tetrahydrobenzo[c]thiophen-4-one;

6,6-Dimethyl-3-ethylthio-1-(pyrazol-3-yl)-4,5,6,7-tetrahydrobenzo[c]thiophen-4-one;

6,6-Dimethyl-3-phenylthio-1-(pyrazol-3-yl)-4,5,6,7-tetrahydrobenzo[c]thiophen-4-one;

6,6-Dimethyl-3-((N,N-dimethyl-2-aminoethyl)thio)-1-(pyrazol-3-yl)-4,5,6,7-tetrahydrobenzo[c]thiophen-4-one;

6,6-Dimethyl-3-[(2-hydroxyethyl)thio]-1-(pyrazol-3-yl)-4,5,6,7-tetrahydrobenzo[c]thiophen-4-one 6,6-Dimethyl-3-[(2-hydroxypropyl)thio]-1-(pyrazol-3-yl)-4,5,6,7-tetrahydrobenzo[c]thiophen-4-one;

6,6-Dimethyl-3-[(2-methoxyethyl)thio]-1-(pyrazol-3-yl)-4,5,6,7-tetrahydrobenzo[c]thiophen-4-one;

6,6-Dimethyl-1-(isoxazol-5-yl)-3-methylthio-4,5,6,7-tetrahydrobenzo[c]thiophen-4-one;

7,7-Dimethyl-3-methylthio-1-(thiazol-2-yl)-4,5,6,7-tetrahydrobenzo[c]thiophen-4-one;

3-(Benzylamino)-6,6-dimethyl-1-(pyrazol-3-yl)-4,5,6,7-tetrahydrobenzo[c]thiophen-4-one;

6,6-Dimethyl-3-((furan-2-ylmethyl)amino)-1-(pyrazol-3-yl)-4,5,6,7-tetrahydrobenzo[c]thiophen-4-one;

6,6-Dimethyl-3-((2-methylpropyl)amino)-1-(pyrazol-3-yl)-4,5,6,7-tetrahydrobenzo[c]thiophen-4-one;

6,6-Dimethyl-3-(propylamino)-1-(pyrazol-3-yl)-4,5,6,7-tetrahydrobenzo[c]thiophen-4-one;

6,6-Dimethyl-3-((3-imidazol-1-ylpropyl)amino)-1-(pyrazol-3-yl)-4,5,6,7-tetrahydrobenzo[c]thiophen-4-one;

6,6-Dimethyl-3-((2-methoxyethyl)amino)-1-(pyrazol-3-yl)-4,5,6,7-tetrahydrobenzo[c]thiophen-4-one;

3-Cyclopropylamino-6,6-dimethyl-1-(pyrazol-3-yl)-4,5,6,7-tetrahydrobenzo[c]thiophen-4-one;

6,6-Dimethyl-3-((pyrid-2-yl)methylamino)-1-(pyrazol-3-yl)-4,5,6,7-tetrahydrobenzo[c]thiophen-4-one;

6,6-Dimethyl-3-([3-(4-methylpiperazin-1-yl)propyl]amino)-1-(pyrazol-3-yl)-4,5,6,7-tetrahydrobenzo[c]thiophen-4-one;

6,6-Dimethyl-3-methylamino-1-(pyrazol-3-yl)-4,5,6,7-tetrahydrobenzo[c]thiophen-4-one;

6,6-Dimethyl-3-isopropylamino-1-(pyrazol-3-yl)-4,5,6,7-tetrahydrobenzo[c]thiophen-4-one;

6,6-Dimethyl-3-ethylamino-1-(pyrazol-3-yl)-4,5,6,7-tetrahydrobenzo[c]thiophen-4-one;

6,6-Dimethyl-3-((2-hydroxyethyl)amino)-1-(pyrazol-3-yl)-4,5,6,7-tetrahydrobenzo[c]thiophen-4-one;

3-Cyclobutylamino-6,6-dimethyl-1-(pyrazol-3-yl)-4,5,6,7-tetrahydrobenzo[c]thiophen-4-one;

3-(Azetidin-1-yl)-6,6-dimethyl-1-(pyrazol-3-yl)-4,5,6,7-tetrahydrobenzo[c]thiophen-4-one;

6,6-Dimethyl-3-isopropoxy-1-(pyrazol-3-yl)-4,5,6,7-tetrahydrobenzo[c]thiophen-4-one;

3-Methylthio-1-(pyrid-3-yl)-4,5,6,7-tetrahydrobenzo[c]thiophen-4-one;

3-Methylthio-1-(pyrid-4-yl)-4,5,6,7-tetrahydrobenzo[c]thiophen-4-one;

6,6-Dimethyl-3-methylthio-1-(2-methyl-1,3,4-oxadiazol-5-yl)-4,5,6,7-tetrahydrobenzo[c]thiophen-4-one; or 6,6-Dimethyl-3-methylthio-1-(1,3,4-oxadiazol-5-yl)-4,5,6,7-tetrahydrobenzo[c]thiophen-4-one;

and the pharmaceutically acceptable salts thereof.

Preferably the compositions according to the present invention are in unit dosage forms such as tablets, pills, capsules, powders, granules, solutions or suspensions, or suppositories, for oral, parenteral or rectal administration, by inhalation or insufflation or administration by trans-dermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Compositions for inhalation or insufflation include solutions and suspensions in pharmaceutically acceptable, aqueous or organic solvents or mixtures thereof, and powders. The liquid or solid compositions may contain suitable pharmaceutically acceptable excipients as set out above. Preferably the compositions are administered by the oral or nasal respiratory route for local or systemic effect. Compositions in preferably. sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

In disorders associated with $GABA_A$ $\alpha$ receptors, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The present invention also provides a process for the preparation of a pharmaceutical composition which comprises adding a compound of formula (I) or a pharmaceutically acceptable salt thereof to a pharmaceutically acceptable excipient.

The present invention also provides a compound of formula (I) or a pharmaceutically acceptable salt thereof for use in a method of treatment of the human or animal body, in particular for the treatment or prevention of conditions for which the administration of a cognition enhancing agent is desirable, such as Alzheimer's disease.

The compounds of formula (I) are of potential value in the treatment or prevention of a wide variety of clinical conditions which can be alleviated by a ligand selective for $GABA_A$ receptors containing the $\alpha 5$ subunit. In particular, they are desirably inverse agonists of the $\alpha 5$ subunit.

Thus, for example, such a ligand can be used in a variety of disorders of the central nervous system. Such disorders include delirium, dementia and amnestic and other cognitive disorders. Examples of delirium are delirium due to substance intoxication or substance withdrawal delirium due to multiple etiologies and delirium NOS (not otherwise specified). Examples of dementia are: dementia of the Alzheimer's type with early onset which can be uncomplicated or with delirium, delusions or depressed mood; dementia of the Alzheimer's type, with late onset, which can be uncomplicated or with delirium delusions or depressed mood; vascular dementia which can be uncomplicated or with delirium, delusions or depressed mood; dementia due to HIV disease; dementia due to head trauma; dementia due to Parkinson's disease; dementia due to Huntington's disease; dementia due to Pick's disease; dementia due to Creutzfeld-Jakob disease; dementia which is substance-induced persisting or due to multiple etiologies; and dementia NOS. Examples of amnestic disorders are amnestic disorder due to a particular medical condition or which is substance-induced persisting or which is amnestic disorder NOS. In particular the compounds of formula (I) may be of use in conditions which require cognition enhancement.

Where the compounds of the present invention are selective ligands for $GABA_A$ $\alpha 2$ or $\alpha 3$ subtype receptors they may be used in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; and depressive or bipolar disorders, for example single-episode or recurrent major depressive disorder, dysthymic disorder bipolar I and bipolar II manic disorders, and cyclothymic disorder.

The present invention also provides the use of a compound of formula (I) or a pharmaceutically acceptable salt thereof for the manufacture of a medicament for the treatment or prevention of a condition requiring the administration of a ligand selective for $GABA_A$ receptors containing the $\alpha 5$ subunit, in particular for conditions requiring cognition enhancement such as Alzheimer's disease.

There is also disclosed a method of treatment or prevention of a condition associated with $GABA_A$ receptors containing the $\alpha 5$ subunit which comprises administering to a subject suffering from or prone to such a condition a therapeutically or prophylactically effective amount of a compound of formula (I) or a pharmaceutically acceptable salt thereof. In particular there is disclosed the treatment and prevention of conditions which require the administration of a cognition enhancing agent, such as Alzheimer's disease.

As used herein, the expression "$C_{1-6}$alkyl" includes methyl and ethyl groups, and straight-chained and branched propyl, butyl, pentyl and hexyl groups. Particular alkyl groups are methyl, ethyl, n-propyl. isopropyl and t-butyl. Derived expressions such as "$C_{2-6}$alkenyl", "$C_{2-6}$alkynl", "$C_{1-4}$alkyl", "$C_{2-4}$alkenyl" and "$C_{2-4}$alkynyl" are to be construed in an analogous manner.

The expression "$C_{3-6}$cycloalkyl" includes cyclopropyl, cyclobutyl, cyclopentyl and cyclohexyl groups. "$C_{5-6}$cycloalkenyl", "$C_{3-8}$cycloalkyl" and "$C_{5-7}$cycloalkyl" are to be construed analogously.

Suitable 5- and 6-membered heteroaromatic rings include pyridinyl, pyridazinyl, pyrimidinyl, pyrazinyl, furyl, thienyl, pyrrolyl, pyrazolyl, oxazolyl, isoxazolyl, isothiazolyl, imidazolyl, tetrazolyl, oxadiazolyl and thiadiazolyl groups. These rings also include thiazolyl and triazolyl groups.

The term "halogen" as used herein includes fluorine, chlorine, bromine and iodine especially fluorine, chlorine and bromine.

The expression "aryl$C_{1-6}$alkyl" as used herein includes benzyl, phenylethyl, phenylpropyl and naphthylmethyl. "Aryl$C_{2-6}$alkenyl" and "aryl$C_{2-6}$alkynyl" should be construed in an analogous fashion.

Typical aryl groups include phenyl and naphthyl. Preferably the aryl is phenyl.

For use in medicine, the salts of the compounds of formula (I) will be pharmaceutically acceptable salts. Other salts may, however be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

Where the compounds of formula (I) have at least one asymmetric centre, they may accordingly exist as enantiomers. Where the compounds of formula (I) possess two or more asymmetric centres, they may additionally exist as diastereoisomers. It is to be understood that all such isomers and mixtures thereof in any proportion are encompassed within the scope of the present invention.

The present invention also provides a novel compound of formula (I) or a pharmaceutically acceptable salt thereof as defined above. The skilled person will appreciate that the alternative and preferred embodiments of these compounds in the pharmaceutical compositions described above are also alternative and preferred embodiments of the novel compounds of formula (I) provided by the present invention.

Aptly novel compounds of this invention include those wherein $R^2$ and $R^3$ are not 6-position gem-dimethyl.

Aptly novel compounds of this invention include those wherein p is 1 or 2.

Aptly novel compounds of this invention include those wherein Her is not a thiazole, pyrimidine or pyrazole.

Aptly novel compounds of this invention include those wherein $R^1$ is not methyl.

Aptly novel compounds of this invention include those wherein $R^4$ is not hydrogen, methyl or $CH_2(CO)_mNR^8R^9$.

The present invention also provides a process for producing a compound of formula (I) which comprises:

(i) reacting a compound of formula II:

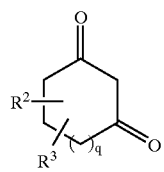

(II)

in which $R^2$, $R^3$ are as defined above, with NaH, then with $CS_2$, then with a compound of formula III and then with a compound of formula IV:

HalR$^1$      (III)

Hal'CH$_2$R$^{15}$      (IV)

in which $R^1$ is as defined above, Hal is a halogen atom such as iodine, Hal' is a halogen atom such as bromine or chlorine and $R^{15}$ is CN, COH C(O)$C_{1-6}$alkyl or CO$_2C_{1-6}$alkyl to produce a compound of formula VI:

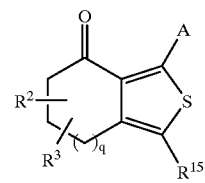

(VI)

in which A is $S(O)_pR^1$, p is zero and $R^1.R^2.R^{15}$ and q are as defined above and when $R^{15}$ is CO$_2C_{1-6}$alkyl optionally converting it by hydrolysis to a group of formula CO$_2$H and optionally decarboxylating this group to leave a hydrogen atom and optionally converting the hydrogen to a bromine atom by reacting with a brominating agent such as N-bromo succinimide or copper (I) bromide; and (ii) converting the group $R^{15}$ to a group B as defined above by standard techniques to obtain a compound of formula I;

(iii) optionally oxidising the compound of formula VI or the compound of formula I thus obtained to a compound of formula VI or I in which p is 1 or 2, for example by using a stoichiometric quantity of mCPBA, generally in a solvent such as CH$_2$Cl$_2$:dioxan with cooling to about −78° C.; and (iv) optionally converting the compound of formula VI or I, as the case may be, to a compound of formula VI or I in which A is other than $S(O)_pR^1$ by standard techniques.

Step (i) of the above process constitutes a further feature of the present invention. It is generally carried out in a solvent such as DMF and at about 0° C. to about room temperature.

Illustrative examples of conversions of the group $R^{15}$ to a group B are as follows; the skilled worker would have no difficulty in adapting these methods or in using other standard techniques to produce compounds in which B is other than as illustrated here:

when $R^{15}$ is CN it can be converted to: a tetrazole using, for example, sodium azide, a thiazole using $H_2S$ and $HC(O)CH_2Cl$: and a triazole using formyl hydrazine;

when $R^{15}$ is $CO_2H$ it can be converted to an oxadiazole by using: carbonyldiimidazole and an amide oxime; or hydrazine and formic acid:

when $R^{15}$ is $C(O)CH_3$ it can be converted to an isoxazole using EtOC(O)H and $NH_2OH.HCl$.

Alternatively the group B can replace the group $R^{15}$ when the latter is bromine by a Stille reaction using the appropriate trialkyltin derivative and a catalyst such as dichlorobis(triphenylphosphine)palladium (II) or palladium tetrakisphenylphosphine or by a Suzuki reaction using the appropriate boronic acid derivative.

Further details of the above reactions can be found, for example, in Comprehensive Organic Syntheses, ed. B. M. Trost. Pergamon Press, Oxford.

Compounds of formula I or VI in which A is $SR^1$ can be obtained by reacting a compound of formula I or VI in which A is $S(O)_pR^1$ where p is one or two and $R^1$ is as defined above with a thiol in the presence of a base.

Compounds of formula I or VI in which A is $C_{1-6}$alkyl, $C_{2-6}$alkenyl, $C_{2-6}$alkynyl or $C_{3-6}$cycloalkyl can be obtained by reacting a compound of formula I or VI in which A is $S(O)_pR$ where p is zero or two with an appropriate Grignard reagent.

Compounds of formula I or VI in which A is $OR^1$ can be obtained by reacting a compound of formula I or VI in which A is $S(O)_pR^1$ and p is one or two with an alcohol in the presence of a strong base.

Compounds of formula I or VI in which A is $NR^1R^{14}$ can be obtained by reacting a compound of formula I or VI in which A is $S(O)_pR^1$ and p is one or two with an amine.

It will be understood that the above transformations of $S(O)_pR^1$ are illustrative and other standard techniques known to the skilled person may alternatively be used. The above reactions are illustrated in the Examples.

Compounds of formula VI in which $R^{15}$ is CN, Br or $C(O)CH_3$, p is zero, $R^1$ is $CH_3$ and $R^2$ and $R^3$ are 6,6-dimethyl are commercially available.

The compound of formula VI in which p is zero, $R^1$ is $CH_3$, $R^2$ and $R^3$ are 6,6-dimethyl and $R^{15}$ is bromo can be prepared from

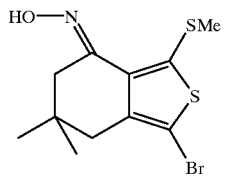

which is commercially available by heating the above compound with 1M HCl in THF and methanol.

The compound of formula I in which A is methylthio, B is pyrazol-3-yl, $R^2$ and $R^3$ are 6,6-dimethyl and q is 1 is commercially available; it can also be made by the methods disclosed herein.

Compounds of formulae (II), (III) and (IV) are known in the art or can be made by known methods from known starting materials.

The following Examples illustrate pharmaceutical compositions according to the invention.

COMPOSITION EXAMPLE 1A

Tablets Containing 1–25 MG of Compound

|  | Amount mg | | |
| --- | --- | --- | --- |
| Active Ingredients(s) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

COMPOSITION EXAMPLE 1B

Tablets Containing 26–100 MG of Compound

|  | Amount mg | | |
| --- | --- | --- | --- |
| Active Ingredients(s) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The active ingredient(s), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0 mg, 2.0 mg. 25.0 mg, 26.0 mg, 50.0 mg and 100 mg of the active compound per tablet.

COMPOSITION EXAMPLE 2

Parenteral Injection

|  | Amount |
| --- | --- |
| Active Ingredient(s) | 1 to 100 mg |
| Citric Acid Monohydrate | 0.75 mg |
| Sodium Phosphate | 4.5 mg |
| Sodium Chloride | 9 mg |
| Water for injection | to 10 ml |

The sodium phosphate, ditric acid monohydrate and sodium chloride are dissolved in a portion of the water. The active ingredient(s) is (are) dissolved or suspended in the solution and made up to volume.

COMPOSITION EXAMPLE 3

Topical Formulation

|  | Amount |
| --- | --- |
| Active Ingredient(s) | 1–10 g |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The active ingredient(s) is (are) is added and stirring continued until dispersed. The mixture is then cooled until solid.

The following Examples illustrate the compounds of the present invention.

The compounds in accordance with this invention potently inhibit the binding of [$^3$H]-flumazenil to the benzodiazepine binding site of human GABA$_A$ receptors containing the α5 subunit stably expressed in Ltk cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3λ2 cells; 18 nM for α2β3λ2 cells; 10 nM for α3β3λ2 cells; 10 nM for α5β3λ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3μ2: 1.8 nM; for α2β3λ2: 1.8 nM; for α3β3λ2: 1.0 nM; for α5β3λ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant K$_i$ can be calculated for each test compound.

The compounds of the accompanying Examples were tested in the above assay, and all were found to possess a K$_i$ value for displacement of [$^3$H]Ro 1.5-1788 from the α5 subunit of the human GABA$_A$ receptor of 500 nM or less, preferably of 100 nM or less, and more particularly of 50 nM or less.

EXAMPLE 1

6.6-Dimethyl-1-(2-methyltetrazol-5-yl)-3-methnethylthio-4,5,6,7-tetrahydrobenzo[c]thiophen-4-one Step 1:6.6-Dimethyl-3-methyithio-1-(tetrazol-5-yl)-4,5,6,7-tetrahydrobenzol[c]thiophen-4-one A solution of 1-cyano-6,6-dimethyl-3-methylthio-4,5,6,7-tetrahydrobenzo[c]thiophen-4-one (156 mg, 0.6 mmol), sodium azide (117 mg, 1.8 mmol) and triethylamine hydrochloride (124 mg, 0.9 mmol) in N-methylpyrrolidinone (4 mL) was heated at reflux for 2 h. After cooling to room temperature, hydrochloric acid (1 M) was added and the precipitate collected by filtration and washed with ether. The tetrazole (152 mg, 86%) was isolated as a tan solid. mp 268–270 20 C. Found; C, 49.16: H, 4.75; N, 18.67%. C$_{12}$H$_{14}$N$_4$S$_2$O requires: C, 48.96; H, 4.79; N, 19.03%. $^1$HNMR (360 MHz, d$_6$-DMSO) δ 1.02 (6H, s), 2.43 (2H, s), 2.66 (3H, s), 3.05 (2H, s). MS (ES$^+$) 295 (M+1).

Step 2; 6,6-Dimethyl-1-(2-methyltetrazol-5-yl)-3-methylthio-4,5,6,7-tetrahydrobenzo[c]thiophen-4-one To solution of 6,6-dimethyl-3-methylthio-1-(tetrazol-5-yl)-4,5,6,7-tetrahydrobenzo[c]thiophen-4-one (62 mg, 0.21 mmol) in DMF (5 mL) containing triethylamine (58 μL, 0.42 mmol) was added iodomethane (13 μL, 0.21 mmol). After stirring for 1 h more iodomethane (39 μL, 0.63 mmol) was added and stirring continued overnight. Ethyl acetate (20 ml) and water (20 mL) were added and the organic layer separated, dried (Na$_2$SO$_4$) and evaporated. The residue was triturated with CH$_2$Cl$_2$:EtOAc (1:1) and the undissolved solid (26 mg; 0.08 mmol) collected by filtration and washed with EtOAc. The filtrate was chromatographed on silica gel, eluting with petrol:EtOAc (2:) to give the title compound (10 mg, 0.03 mmol) as a tan solid. Total mass=36 mg (56%), mp 233–235° C. Found C, 50.26; H, 5.23; N, 17.94%. C$_{13}$H$_{16}$N$_4$S$_2$O requires: C,50.63; H, 5.23; N, 18.17%. $^1$HNMR (250 MHz, CDCl$_3$) δ 1.10 (6H, s), 2.45 (2H, s), 2.65 (3H, s), 3.11 (2H, s), 4.40 (3H, s). MS (ES$^+$) 309 (M+1).

EXAMPLE 2

6,6-Dimethyl-3-methanesulphinyl-1-(pyrazol-3-yl)-4,5,6,7-tetrahydrobenzo[c]thiophen-4-one To a stirred solution of 6,6-dimethyl-3-methylthio-1-(pyrazol-3-yl)-4,5,6,7-tetrahydrobenzo[c]thiophen-4-one (200 mg, 0.69 mmol) in CH$_2$Cl$_2$:dioxan (3:1; 9 mL) at −78° C. was added m-CPBA (169 mg (70% w/w); 0.69 mmol) portionwise. After addition the solution was diluted with CH$_2$Cl$_2$ (10 mL) and poured into NaHCO$_3$ (sat., 10 mL). The organic layer was separated, dried (Na$_2$SO$_4$) and evaporated. The residue was triturated in ether to give the sulphoxide (106 mg, 50%) as a cream solid. mp 206–210° C. $^1$HNMR (360 MHz, CDCl$_3$) δ 1.09 (3H, s), 1.11 (3H, s), 2.42 (1H, d, J=17 Hz), 2.52 (1H, d, J=17 Hz), 2.95 (2H, s), 3.01 (3H, s), 6.54 (1H, s), 7.68 (1H, s). MS (ES$^+$) 309 (M+1).

EXAMPLE 3

6,6-Dimethyl-3-ethyl-1-(pyrazol-3-yl)-4,5,6,7-tetrahydrobenzo[c]thiophen-4-one

To a stirred solution of the sulphoxide (122 mg, 0.4 mmol), prepared according to Example 2, in THF (7 mL) at −10° C. under nitrogen, was added ethylmagnesium bromide (0.79 mL of a 1.0 M solution in THF, 0.79 mmol). After addition the mixture was stirred at −10° C. for 1 h, then NH$_4$Cl (sat., 1 mL) was added. The cooling bath was removed and the mixture stirred at room temperature for 10 min. The mixture was then partitioned between EtOAc (15 mL) and water (15 mL). The organic layer was separated, dried (Na$_2$SO$_4$) and evaporated. The residue was chromatographed on silica, eluting with EtOAc:CH$_2$Cl$_2$ (6:1). The fractions containing the desired product were combined and evaporated and the residue triturated with ether. The title compound (6 mg, 6%) was isolated as a pale yellow solid. mp 152–155° C. $^1$HNMR (360 MHz, CDCl$_3$) δ 1.07 (6H, s), 1.34 (3H, t, J=7.4 Hz), 2.42 (2H, s), 2.87 (2H, s), 3.30 (2H, q, J=7.4 Hz), 6.49 (1H, d, J=2.2 Hz), 7.65 (1H, d, J=2.2 Hz). MS (ES$^+$) 275 (M+1).

EXAMPLE 4

6,6-Dimethyl-3-methylthio-1-(2-proyltetrazol-5-yl)-4,5,6,7-tetrahydrobenzo[c]thiophen-4-one In the same way as described in Example 1, using iodopropane, the title compound (26 mg, 32%) was isolated as a cream solid. mp 163–165° C. Found: C, 53.54; H, 5.67; N, 16.28%. C$_{15}$H$_{20}$N$_4$S$_2$O requires: C, 53.54; H, 5.99; N, 16.65%. $^1$HNMR (360 MHz, d$_6$-DMSO) δ 0.92 (3H, t, J=7.4 Hz), 1.03 (6H, s), 1.95–2.02 (2H, m), 2.43 (2H, s), 2.66 (3H, s), 3.09 (2H, s), 4.70 (2H, t, J=7.0 Hz). MS (ES$^+$) 337 (M+1).

EXAMPLE 5

6,6-Dimethyl-1-(1-methanesulphonylpyrazol-3-yl)-3-methylthio-4,5,6,7-tetrahydrobenzo[c]thiophen-4-one To a solution of 6,6-dimethyl-3-methylthio-1-(pyrazol-3-yl)-4,5,6,7-tetrahydrobenzo[c]thiophen-4-one (70 mg, 0.24 mmol) in CH$_2$Cl$_2$:THF (5:1, 6 mL), was added methanesulphonyl chloride (36 μL, 0.48 mmol) and 4-dimethylaminopyridine (58 mg, 0.48 mmol). The mixture was stirred at room temperature overnight then diluted with CH$_2$Cl$_2$ (10 mL) and washed with water (2×10 mL). The organic layer was separated, dried (Na$_2$SO$_1$) and evaporated. The residue was chromatographed on silica gel, eluting with CH$_2$Cl$_2$:MeOH (95:5), to give the title compound (38 mg, 43%) as a pale yellow solid. mp 193–195° C. Found: C, 47.72; H, 4,71; N, 7.16%. C$_{15}$H$_{18}$N$_2$S$_3$O$_3$.0.3 (H$_2$O) requires: C, 47.93, H, 4.99; N, 7.45%. $^1$HNMR (360 Hz, d$_6$-DMSO) δ 1.02 (6H, s), 2.41 (2H, s), 2.64 (3H, s), 2.90 (2H, s), 3.61 (3H, s), 6.91 (1H, d, J=2.8 Hz). MS (ES$^+$) 371 (M+1).

EXAMPLE 6

6,6-Dimethyl-3-(2-methylprop-1-yl)-1-(thiazol-2-yl)-4,5,6,7-tetrahydrobenzo[c]thiophen-4-one Step 1: 1-Cyano-6,6-dimethyl-3(2-methylprop-1-yl)-4,5,6,7-tetrahydrobenzo[c]thiophen-4-one To a stirred solution of 1-cyano-6,6-dimethyl-3-methanesulphonyl-4,5,6,7-tetrahydrobenzo[c]thiophen-4-one (1.5 g, 5.3 mmol) in THF (15 mL) at −10° C. was added isobutylmagnesium chloride. After 1 h the cooling bath was removed and the mixture stirred at room temperature for 2 h. After this time the mixture was partitioned between EtOAc (20 mL) and water (20 mL). The organic layer was separated, dried (Na$_2$SO$_4$) and evaporated. The residue was chromatographed on silica gel, eluting with petrol: EtOAc (6:1), to give the title compound (526 mg, 38%) as an orange oil. $^1$HNMR (360 MHz, CDCl$_3$) δ 0.97 (6H, d, J=6.6 Hz), 1.08 (6H, s), 1.94–2.02 (1H, m), 2,42 (2H, s), 2.85 (2H, s), 3.16 (2H, d, J=7.1 Hz).

Step 2: 6,6-Dimethyl-3-(2-methylprop-1-yl)-4,5,6,7-tetrahydrobenzo[c]thiophen -4-one-1-thiocarboxamide A solution of the nitrile (526 mg, 2.0 mmol) in pyridine (5 mL and triethylamine (0.3 mL) was treated with hydrogen sulphide for 20 min. After this time the solution was left to stand overnight. The solution was then poured into water (50 mL) and stirred for 1 h. The precipitate was collected by filtration, washed with water then triturated with hexane. The desired thioamide (600 mg, 100%) was collected by filtration and isolated as a yellow solid. mp 153–156° C. Found: C, 61.11; H, 7.31; N, 4.77%. Calc: C, 60.98; H, 7.16; N, 4,74%. $^1$HNMR (360 MHz, CDCl$_3$) δ 0.97 (6H, d, J=6.6 Hz), 1.07 (6H, s), 1.94–2.03 (1H, m), 2.40 (2H, s), 2.98 (2H, s), 3.12 (2H, d, J=7.0 Hz), 6.90 (1H, br s), 7.40 (1H, br s). MS (ES$^+$) 296 (M+1).

Step 3: 6,6-Dimethyl-3-(2-methylprop-1-yl)-1-(thiazol-2-yl)-4,5,6,7-tetrahydrobenzo[c]thiophen-4-one A solution of the thioamide (500 mg, 1.7 mmol) in EtOH (5 mL) was heated at relux, in the presence of chloroacetaldehyde (0.43 mL of a 50% (w/v) aqueous solution, 2.7 mmol), for 18 h. After this time the solvent was evaporated and the residue partitioned between EtOAc (20 mL) and water (20 mL). The organic layer was separated, dried (Na$_2$SO$_4$) and evaporated. The residue was chromatographed on silica gel, eluting with petrol: EtOAc (6:1→3:1), to give the thiazole (190 mg, 35%) as a beige solid. mp 98–100° C. Found: C, 64.29; H, 6.54; N, 4.37%. C$_{17}$H$_{21}$NOS$_2$ requires: C, 63.91; H, 6.63; N, 4.38%. $^1$HNMR (360 MHz, CDCl$_3$) δ 0.99 (6H, d, J=6.6 Hz), 1.11 (6H, s), 1.99–2.07 (1H, m), 2.44 (2H, s), 2.94 (2H, s), 3.17 (2H, d, J=7.1 Hz), 7.35 (1H, d, J=3.4 Hz), 7.84 (1H, d, J=3.4 Hz). MS (ES$^+$) 320 (M+1).

EXAMPLE 7

6,6-Dimethyl-3-isopropyl-1-(thiazol-2-yl)-4,5,6,7-tetrahydrobenzo[c]thiophen-4-one Step 1: 1-Cyano-6,6-dimethyl-3-isopropyl-4,5,6,7-tetrahydrobenzo[c]thiophen-4-one In the same way as described in Example 6, Step 1, using isopropylmagnesium chloride and 1-cyano-6,6-dimethyl-3-methylthio-4,5,6,7-tetrahydrobenzo[c]thiophen-4-one, the title compound (1.2 g, 36%) was isolated as a colourless solid. mp 59–60° C. Found: C, 68.08; H, 6.97; N, 5.48%. C$_{14}$H$_{17}$NOS requires: C, 67.98; H, 6.93; N, 5.66%. $^1$HNMR (360 MHz, CDCl$_3$) δ 1.08 (6H, s), 1.32 (6H, d, J=6.7 Hz), 2.43 (2H, s), 2.85 (2H, s), 4.24 (1H, heptet, J=6.7 Hz).

Step 2: 6,6-Dimethyl-3-isopropyl-4,5,6,7-tetrahydrobenzo[c]thiophen-4-one-1-thiocarboxamide In the same way as described in Example 6, Step 2, using 1-cyano-6,6-dimethyl-3-isopropyl-4,5,6,7-tetrahydrobenzo [c]thiophen-4-one, the title compound (0.58 g, 100%) was isolated as a yellow solid. mp 169–171° C. Found: C, 59,89; H, 6.64; N, 4.98%. C$_{14}$H$_{19}$NS$_2$O requires: C, 59.75; H, 6.81; N, 4.98%. $^1$HNMR (250 MHz, CDCl$_3$) δ 1.08 (6H, s), 1.32 (6H, d, J=6.8 Hz), 2.41 (2H, s), 2.98 (2H, s), 4.23 (1H, heptet, J=6.8 Hz), 6.88 (1H, br s), 7.40 (1H, br s). MS (ES$^+$) 282 (M+1).

Step 3: 6,6-Dimethyl-3-isopropyl-1-(thiazol-2-yl)-4,5,6,7-tetrahydrobenzo[c]thiophen-4-one In the same way as described in Example 6, Step 3, using 6,6-dimethyl-3-isopropyl-4,5,6,7-tetrahydrobenzo[c] thiophen-4-one-1-thiocarboxamide, the thiazole (185 mg, 33%) was isolated as a cream solid. mp. 106–108° C. Found:

C, 63.22; H, 6.17; N, 4.50%. $C_{16}H_{19}NS_2O$ requires: C, 62.91; H, 6.27; N, 4.59%. $^1$HNMR (360 MHz, $CDCl_3$) δ 1.11 (6H, s), 1.34 (6H, d, J=6.9 Hz), 2.45 (2H, s), 2.94 (2H, s), 4.27 (1H, heptet, J=6.9 Hz), 7.35 (1H, d, J=3.3 Hz), 7.83 (1H, d, J=3.3 Hz). MS ($ES^+$) 306 (M+1).

EXAMPLE 8

6,6-Dimethyl-3-propyl-1-(thiazol-2-yl)-4,5,6,7-tetrahydrobenzo[c]thiophen-4-one

Step 1: 1-Cyano-6,6-dimethyl-3-propyl-4,5,6,7-tetrahydrobenzo[c]thiophen-4-one

In the same way as described in Example 6, Step 1, using propylmagnesium chloride, the title compound (0.31 g, 36%) was isolated as an orange solid. mp 38–40° C. $^1$HNMR (360 MHz, $CDCl_3$) δ 1.02 (3H, t, J=7.3 Hz), 1.08 (6H, s), 1.68–1.78 (2H, m), 2.42 (2H, s), 2.85 (2H, s), 3.25 (2H, t, J=7.6 HZ). MS ($ES^+$) 248 (M+1).

Step 2: 6,6-Dimethyl-3-propyl-4,5,6,7-tetrahydrobenzo[c]thiophen-4-one-1-thiocarboxamide In the same way as described in Example 6, Step 2, using 1-cyano-6,6-dimethyl-3-propyl-4,5,6,7-tetrahydrobenzo[c]thiophen-4-one, the title compound (555 mg, 100%) was obtained as a yellow solid. mp 142–145° C. $^1$HNMR (360 MHz, $CDCl_3$) δ 1.02 (3H, t, J=7.3 Hz), 1.08 (6H, s), 1.67–1.79 (2H, m), 2.40 (2H, s), 2.98 (2H, s), 3.21 (2H, t, J=7.6 Hz), 6.86 (1H, br s), 7.44 (1H, br s). MS ($ES^+$) 282 (M+1).

Step 3: 6,6-Dimethyl-3-propyl-1-(thiazol-2-yl)-4,5,6,7-tetrahydrobenzo[c]thiophen-4-one In the same way as described in Example 6, Step 3, using 6,6-dimethyl-3-propyl-4,5,6,7-tetrahydrobenzo[c]thiophen-4-one-1-thiocarboxamide, the thiazole (185 mg, 34%) was isolated as a pale yellow solid. mp 69–72° C. Found: C, 63.31; H, 6.17; N, 4.62%. $C_{16}H_{19}NOS_2$ requires: C, 62.91; H, 6.27; N, 4.59%. $^1$HNMR (360 MHz, $CDCl_3$) δ 1.03 (3H, t, J=7.4 Hz), 1.11 (6H, s), 1.70–1.82 (2H, m), 2.45 (2H, s), 2.94 (2H, s), 3.26 (2H, t, J=7.5 Hz), 7.35 (1H, d, J=3.2 Hz), 7.84 (1H, d, J=3.4 Hz). MS ($ES^+$) 306 (M+1).

EXAMPLE 9

6,6-Dimethyl-3-phenyl-1-(thiazol-2-yl)-4,5,6,7-tetrahydrobenzo[c]thiophen-4-one

Step 1: 1-Cyano-6,6-dimethyl-3-phenyl-4,5,6,7-tetrahydrobenzo[c]thiophen-4-one

In the same way as described in Example 6, Step 1, using phenylmagnesium bromide, the title compound (0.17 g, 86%) was isolated as a cream solid. mp 100–103° C. $^1$HNMR (250 MHz, $CDCl_3$) δ 1.13 (6H, s), 2.47 (2H, s), 2.94 (2H, s), 7.40–7.48 (3H, m), 7.54–7.58 (2H, m).

Step 2: 6,6-Dimethyl-3-phenyl-4,5,6,7-tetrahydrobenzo[c]thiophen-4-one-1-thiocarboxamide In the same way as described in Example 6, Step 2, using 1-cyano-6,6-dimethyl-3-phenyl-4,5,6,7-tetrahydrobenzo[c]thiophen-4-one, the title compound (532 mg, 94%) was obtained as a yellow solid. mp 202–204° C. $^1$HNMR (360 MHz, $CDCl_3$) δ 1.12 (6H, s), 2.44 (2H, s), 3.05 (2H, s), 7.38–7.42 (3H, m), 7.52–7.55 (2H, m). MS ($ES^+$) 316 (M+1).

Step 3: 6,6-Dimethyl-3-phenyl-1-(thiazol-2-yl)-4,5,6,7-tetrahydrobenzo[c]thiophen-4-one In the same way as described in Example 6, Step 3, using 6,6-dimethyl-3-phenyl-4,5,6,7-tetrahydrobenzo[c]thiophen-4-one-1-thiocarboxamide, the thiazole (75 mg, 24%) was isolated as a cream solid. mp 141–143° C. Found: C, 67.45; H, 4.95; N, 4.17%. $C_{19}H_{17}NOS_2$ requires: C, 67.22; H, 5.05; N, 4.13%. $^1$HNMR (360 MHz, $CDCl_3$) δ 1.16 (6H, s), 2.49 (2H, s), 3.03 (2H, s), 7.39–7.42 (4H, m), 7.59–7.63 (2H, m), 7.88 (1H, d, J=3.3 Hz). MS ($ES^+$) 340 (M+1).

EXAMPLE 10

3-Cyclohexyl-6,6-dimethyl-1-(thiazol-2-yl)-4,5,6,7-tetrahydrobenzo[c]thiophen-4-one Step 1: 1-Cyano-3-cyclohexyl-6,6-dimethyl-4,5,6,7-tetrahydrobenzo[c]thiophen-4-one In the same way as described in Example 6, Step 1, using cyclohexylmagnesium chloride and 1-cyano-6,6-dimethyl-3-methylthio-4,5,6,7-tetrahydrobenzo[c]thiophen-4-one, the title compound (0.63 g, 28%) was isolated as a cream solid. mp 129–132° C. $^1$HNMR (360 MHz, $CDCl_3$) δ 1.07 (6H, s), 1.20–1.55 (5H, m), 1.75–1.85 (3H, m), 2.01–2.06 (2H, m), 2.42 (2H, s), 2.84 (2H, s), 3.85–3.94 (1H, M).

Step 2: 3-Cyclohexyl-6,6-dimethyl-4,5,6,7-tetrahydrobenzo[c]thiophen-4-one-1-thiocarboxamide In the same way as described in Example 6, Step 2, using 1-cyano-3-cyclohexyl-6,6-dimethyl-4,5,6,7-tetrahydrobenzo[c]thiophen-4-one, the title compound (614 mg, 100%) was obtained as a yellow solid. mp 196–199° C. $^1$HNMR (360 MHz, $CDCl_3$) δ 1.07 (6H, s), 1.21–1.52 (5H, m), 1.73–1.84 (3H, m), 2.00–2.05 (2H, m), 2.40 (2H, s), 2.98 (2H, s), 3.84–3.92 (1H, m), 6.86 (1H, br s), 7.50 (1H, br s). MS ($ES^+$) 322 (M+1).

Step 3: 3-Cyclohexyl-6,6-dimethyl-1-(thiazol-2-yl)-4,5,6,7-tetrahydrobenzo[c]thiophen-4-one In the same way as described in Example 6, Step 3, using 3-cyclohexyl-6,6-dimethyl-4,5,6,7-tetrahydrobenzo[c]thiophen-4-one-1-thiocarboxamide, the thiazole (180 mg, 56%) was isolated as a green solid. mp 101–103° C. Found: C, 66.39; H, 6.58; N, 4.06%. $C_{19}H_{23}NOS_2$ requires: C, 66.05; H, 6.71; N, 4.05%. $^1$HNMR (360 MHz, $CDCl_3$) δ 1.11 (6H, s), 1.23–1.50 (5H, m), 1.73–1.85 (3H, m), 2.04–2.09 (2H, m), 2.45 (2H, s), 2.94 (2H, s), 3.89–3.95 (1H, m), 7.34 (1H, d, J=3.4 Hz), 7.83 (1H, d, J=3.2 Hz). MS ($ES^+$) 346 (M+1).

EXAMPLE 11

3-Cyclobutyl-6,6-dimethyl-1-(thiazol-2-yl)-4,5,6,7-tetrahydrobenzo[c]thiophen-4-one Step 1: 1-Cyano-3-cyclobutyl-6,6-dimethyl-4,5,6,7-tetrahydrobenzo[c]thiophen-4-one In the same way as described in Example 6, Step 1, using cyclobutylmagnesium bromide and 1-cyano-6,6-dimethyl-3-methylthio-4,5,6,7-tetrahydrobenzo[c]thiophen-4-one, the title compound (0.37 g, 18%) was isolated as a pale yellow solid. mp 65–68° C. $^1$HNMR (360 MHz, $CDCl_3$) δ 1.06 (6H, s), 1.90–1.98 (1H, m), 2.00–2.12 (3H, m), 2.40 (2H, s), 2.50–2.62 (2H, m), 2.83 (2H, s), 4.45–4.56 (1H, m).

Step 2: 3-Cyclobutyl-6,6-dimethyl-4,5,6,7-
tetrahydrobenzo[c]thiophen-4-one-1-
thiocarboxamide In the same way as described in Example 6, Step 2, using 1-cyano-3-cyclobutyl-6,6-dimehtyl-4,5,6,7-tetrahydrobenzo[c]thiophen-4-one, the title compound (309 mg, 74%) was obtained as a yellow solid. mp 212–215° C. $^1$HNMR (360 MHz, CDCl$_3$) δ 1.07 (6H, s), 1.84–1.96 (1H, m), 2.00–2.16 (3H, m), 2.38 (2H, s), 2.50–2.58 (2H, m), 2.96 (2H, s), 4.40–4.50 (1H, m). MS (ES$^+$) 294 (M+1).

Step 3: 3-Cyclobutyl-6,6-dimethyl-1-(thiazol-2-yl)-
4,5,6,7-tetrahydrobenzo[c]thiophen-4-one In the same way as described in Example 6, Step 3, using 3-cyclobutyl-6,6-dimethyl-4,5,6,7-tetrahydrobenzo[c]thiophen-4-one-1-thiocarboxamide, the thiazole (273 mg, 86%) was isolated as a blue/green solid. mp 126–128° C. Found: C, 63.84; H, 5.98; N, 4.31%. $C_{17}H_{19}NOS_2$.0.1 (H$_2$O) requires: C, 63.95; H, 6.06; N, 4.93%. $^1$HNMR (360 MHz, CDCl$_3$) δ 1.10 (6H, s), 1.90–1.96 (1H, m), 2.04–2.20 (3H, m), 2.42 (2H, s), 2.50–2.60 (2H, m), 2.93 (2H, s), 4.50–4.60 (1H, m), 7.35 (1H, d, J=3.2 Hz), 7.84 (1H, d, J=3.2 Hz). MS (ES$^+$) 318 (M+1).

EXAMPLE 12

3-(But-3-enyl)-6,6-dimethyl-1-(thiazol-2-yl)-4,5,6,7-
tetrahydrobenzo[c]thiophen-4-one Step 1: 3-(But-3-enyl)-1-cyano-6,6-dimethyl-4,5,6,
7-tetrahydrobenzo[c]thiophen-4-one In the same way as described in Example 6, Step 1, using 3-butenylmagnesium bromide, the title compound (0.95 g, 70%) was isolated as a pale yellow solid. mp 43–46° C. $^1$HNMR (250 MHz, CDCl$_3$) δ 1.08 (6H, s), 2.40–2.50 (4H, m), 2.85 (2H, s), 3.38 (2H, t, J=10.5 Hz) 5.01–5.10 (2H, m), 5.74–5.90 (1H, m). MS (ES$^+$) 260 (M+1).

Step 2: 3-(But-3-enyl)-6,6-dimethyl-4,5,6,7-
tetrahydrobenzo[c]thiophen-4-one-1-
thiocarboxamide In the same way as described in Example 6, Step 2, using 3-(but-3-enyl)-1-cyano-6,6-dimethyl-4,5,6,7-tetrahydrobenzo[c]thiophen-4-one, the title compound (559 mg, 99%) was obtained as a yellow solid. mp 125–128° C. $^1$HNMR (360 MHz, CDCl$_3$) δ 1.08 (6H, s), 2.40–2.48 (4H, m), 2.98 (2H, s), 3.34 (2H, t, J=7.4 Hz), 5.00–5.09 (2H, m), 5.79–5.91 (1H, m), 6.86 (1H, br s), 7.42 (1H, br s). MS (ES$^+$) 294 (M+1).

Step 3: 3-(But-3-enyl)-6,6-dimethyl-1-(thiazol-2-
yl)-4,5,6,7-tetrahydrobenzo[c]thiophen-4-one In the same way as described in Example 6, Step 3, using 3-(but-3-enyl)-6,6-dimethyl-4,5,6,7-tetrahydrobenzo[c]thiophen-4-one-1-thiocarboxamide, the thiazole (0.21 g, 66%) was isolated as a cream solid. mp 62–65° C. Found: C, 64.40; H, 6.08; N, 4.44%. $C_{17}H_{19}NOS_2$ requires: C, 64.32; H, 6.03; N, 4.41%. $^1$HNMR (360 MHz, CDCl$_3$) δ 1.11 (6H, s), 2.45–2.52 (4H, m), 2.94 (2H, s), 3.39 (2H, t, J=7.3 Hz), 4.99–5.10 (2H, m), 5.82–5.94 (1H, m), 7.35 (1H, d, J=3.4 Hz), 7.84 (1H, d, J=3.4 Hz). MS (ES$^+$) 318 (M+1).

EXAMPLE 13

3-Cyclopropyl-6,6-dimethyl-1-(thiazol-2-yl)-4,5,6,7-
tetrahydrobenzo[c]thiophen-4-one Step 1: 1-Cyano-3-cyclopropyl-6,6-dimethyl-4,5,6,
7-tetrahydrobenzo[c]thiophen-4-one In the same way as described in Example 6, Step 1, using cyclopropylmagnesium bromide, the title compound (0.48 g, 29%) was isolated as a yellow solid. mp 80–83° C. $^1$HNMR (360 MHz, CDCl$_3$)δ 0.82 (2H, m), 1.09 (6H, s), 1.31–1.36 (2H, m), 2.45 (2H, s), 2.82 (2H, s), 3.34–3.42 (1H, m). MS (ES$^+$) 246 (M+1).

Step 2: 3-Cyclopropyl-6,6-dimethyl-4,5,6,7-
tetrahydrobenzo[c]thiophen-4-one-1-
thiocarboxamide In the same way as described in Example 6, Step 2, using 1-cyano-3-cyclopropyl-6,6-dimethyl-4,5,6,7-tetrahydrobenzo[c]thiophen-4-one, the title compound (536 mg, 94%) was obtained as a yellow solid. mp 196–199° C. $^1$HNMR (360 MHz, CDCl$_3$)δ 0.86–0.92 (2H, m), 1.09 (6H, s), 1.26–1.32 (2H, m), 2.43 (2H, s), 2.94 (2H, s), 3.33–3.40 (1H, m). MS (ES$^-$) 280 (M+1).

Step 3: 3-Cyclopropyl-6,6-dimethyl-1-(thiazol-2yl)-
4,5,6,7-tetrahydrobenzo[c]thiophen-4-one In the same way as described in Example 6, Step 3, using 3-cyclopropyl-6,6-dimethyl-4,5,6,7-tetrahydrobenzo[c]thiophen-4-one-1-thiocarboxamide, the thiazole (195 mg, 64%) was isolated as a cream solid. mp 103–105° C. Found: C, 63.47; H, 5.65; N, 4.58%. $C_{16}H_{17}NOS_2$ requires: C, 63.33; H, 5.65; N, 4.62%. $^1$HNMR (360 MHz, CDCl$_3$)δ 0.85–0.91 (2H, m), 1.13 (6H, s), 1.24–1.31 (2H, m), 2.47 (2H, s), 2.91 (2H, s), 3.36–3.42 (1H, m), 7.33 (1H, d, J=3.4 Hz), 7.80 (1H, d, J=3.2 Hz). MS (ES$^+$) 304 (M+1).

EXAMPLE 14

6,6-Dimethyl-3-(2-methylprop-1-enyl)-1-(thiazol-2-
yl)-4,5,6,7-tetrahydrobenzo[c]thiophen-4-thione Step 1: 1-Cyano-6,6-dimethyl-3-(2-methylprop-1-
enyl)-4,5,6,7-tetrahydrobenzo[c]thiophen-4-one In the same way as described in Example 6, Step 1, using 2-methyl-1-propenylmagnesium bromide, the title compound (0.59 g, 43%) was isolated as a pale yellow solid. mp 115–117° C. $^1$HNMR (360 MHz, CDCl$_3$)δ 1.08 (6H, s), 2.07 (6H, s), 2.44 (2H, s), 2.85 (2H, s), 7.64–7.65 (1H, m), MS (ES$^+$) 260 (M+1).

Step 2: 6,6-Dimethyl-3-(2-mercapto-2-
methylpropyl)-4,5,6,7-tetrahydrobenzo[c]thiophen-
4-one-1-thiocarboxamide In the same way as described in Example 6, Step 2, using 1-cyano-6,6-dimethyl-3-(2-methylprop-1-enyl)-4,5,6,7-tetrahydrobenzo[c]thiophen-4-one, the title compound (635 mg, 100%) was obtained as a yellow solid. mp 156–165° C. $^1$HNMR (360 MHz, CDCl$_3$)δ 1.08 (6H, s), 1.44 (6H, s), 2.41 (2H, s), 3.02 (2H, s), 3.71 (2H, s), 6.92 (1H, br s), 7.50 (1H, br s), MS (ES$^+$) 328 (M+1).

Step 3: 6,6-Dimethyl-3-(2-methylprop-1-enyl)-4,5,6,
7-tetrahydrobenzo[c]thiophen-4-thione-1-
thiocarboxamide A solution of the thiol (300 mg, 0.92 mmol) in THF (20 ml) and HCl (1M, 5 ml) was heated at reflux for 2 h. After cooling, the mixture was partitioned between EtOAc (50 mL) and water (50 mL). The two layers were separated and the aqueous extracted with EtOAc (50 mL). The combined organic layers were dried (Na$_2$SO$_4$) and evaporated. The residue was chromatographed on silica gel, eluting with a gradient of EtOAc: hexane (1:3) to EtOAc:hexane (1:1). The fractions containing the desired product were combined and evaporated to afford the title compound (0.2 g, 71%) as a yellow solid. mp 225–228° C. $^1$HNMR (250 MHz, CDCl$_3$)δ 1.12 (6H, s), 1.38 (6H, s), 2.95 (2H, s), 2.98 (2H, s), 5.60 (1H, s), 6.82 (1H, br s), 7.34 (1H, br s), MS (ES$^+$) 310 (M+1).

Step 4: 6,6-Dimethyl-3-(2-methylprop-1-enyl)-1-(thiazol-2-yl)-4,5,6,7-tetrahydrobenzo[c]thiophenp4-thione In the same was as described in Example 6, Step 3, using 6,6-dimethyl-3-(2-methylprop-1-enyl)-4,5,6,7-tetrahydrobenzo[c]thiophen-4-thione-1-thiocarboxamide, the thiazole (150 mg, 93%) was obtained as a pale yellow solid. mp 114–116° C.

Found: C, 61.24; H, 5.60; N, 4.19%. C$_{17}$H$_{19}$NS$_3$ requires: C, 61.22; H, 5.74; N, 4.20%. $^1$HNMR (360 MHz, CDCl$_3$)δ 1.15 (6H, s), 1.41 (6H, s), 2.93 (2H, s), 3.02 (2H, s), 5.60 (1H, s), 7.30 (1H, d, J=3.4 Hz), 7.81 (1H, d, J=3.2 Hz), MS (ES$^+$) 334 (M+1).

EXAMPLE 15

3-Methylthio-1-(pyrid-2-yl)-4,5,6,7-tetrahydro[c]thiophen-4-one

A mixture of 1-bromo-3-methylthio-4,5,6,7-tetrahydro[c]thiophen-4-one (0.1 g, 0.36 mmol) and 2-(tri-n-butylstannyl)pyridine (0.19 g, 0.52 mmol) in dioxane (10 mL) was purged with nitrogen for 20 min. Dichlorobis(triphenylphosphine)palladium (II) (10 mg) was added and the mixture heated at reflux for 4 h. Further dichlorobis(triphenylphosphine)palladium (II) (10 mg) was added and the mixture heated at reflux for 20 h. further catalyst (10 mg) and 2-(tri-n-butylstannyl) pyridine (66 mg, 0.18 mmol) were added and the mixture heated at reflux for 6 h. After cooling, the solvent was evaporated and the residue was chromatographed on silica gel, eluting with EtOAc:hexane (1:2). The fractions containing the desired product were combined and evaporated and the residue triturated with ether. The title compound (28 mg, 28%) was isolated as a yellow solid. mp 188–190° C.

Found: C, 60.98; H, 4.59; N, 4.83%. C$_{14}$H$_{13}$NOS$_2$ requires: C, 61.06; H, 4.76; N, 5.09%. $^1$HNMR (360 MHz, CDCl$_3$)δ 2.07–2.14 (2H, m), 2.57–2.61 (2H, m), 2.65 (3H, s), 3.10 (2H, t, J=6.1 Hz), 7.14–7.18 (1H, m), 7.48 (1H, d, J=8.1 Hz), 7.70–7.75 (1H, m), 8.59–8.62 (1H, m), MS (ES$^+$) 276 (M+1).

EXAMPLE 16

6,6-Dimethyl-3-methanesulphonyl-1-(pyrazol-3-yl)-4,5,6,7-tetrahydrobenzo[c]thiophen-4-one To a stirred solution of 6,6-dimethyl-3-methylthio-1-(pyrazol-3-yl)-4,5,6,7-tetrahydrobenzo[c]thiophen-4-one (2 g, 6.8 mmol) in CH$_2$Cl$_2$:dioxan (3:1:195 mL) at −78° C. was added m-CPBA (3.38 g (70% w/w), 13.6 mmol) portion-wise. The mixture was stirred at −78° C. for 30 min and then allowed to warm to room temperature. After stirring for 2 h, the mixture was poured into NaHCO$_3$ (sat., 100 mL). The organic layer was separated and washed with NaHCO$_3$ (sat., 2×100 mL), dried (Na$_2$SO$_4$) and evaporated. The residue was chromatographed on silica gel, eluting with EtOAc:hexane (1:1) followed by EtOAc. The fractions containing the desired product were combined and evaporated and the residue triturated with ether. The title compound (1.77 g, 80%) was isolated as a cream solid. mp 213–216° C.

Found: C, 50.48; H, 4.67; N, 8.16%. C$_{14}$H$_{16}$N$_2$O$_3$S$_2$.0.15 (CH$_2$Cl$_2$) requires: C, 50.41; H, 4.87; N, 8.31%. $^1$HNMR (360 MHz, CDCl$_3$)δ 1.12 (6H, s), 2.55 (2H, s), 2.98 (2H, s), 3.55 (3H , s), 6.58 (1H, d, J=2.6 Hz), 7.69 (1H, d, J=2.4 Hz). MS (ES$^+$) 325 (M+1).

EXAMPLE 17

1-(Thiazol-2-yl)-3,6,6-trimethyl-4,5,6,7-tetrahydrobenzo[c]thiophen-4-one

Step 1: 1-Cyano-3,6,6-trimethyl-4,5,6,7-tetrahydrobenzo[c]thiophen-4-one

In the same way as that described in Example 6, Step 1, using methylmagnesium bromide, the title compound (0.8 g, 69%) was isolated as a colourless solid. mp 73–75° C.

Found: C, 65.96; H, 5.86; N, 6.39%. C$_{12}$H$_{13}$NOS requires: C, 65.72; H, 5.98; N, 6.39%. $^1$HNMR (250 MHz, CDCl$_3$)δ 1.08 (6H, s), 2.42 (2H, s), 2.82 (3H, s), 2.85 (2H, s).

Step 2: 3,6,6-Trimethyl-4,5,6,7-tetrahydrobenzo[c]thiophen-4-one-1-thiocarboxamide In the same way as that described in Example 6, Step 2, using 1-cyano-3,6,6-trimethyl-4,5,6,7-tetrahydrobenzo[c]thiophen-4-one, gave the thioamide (0.478 g, 100%) as a yellow solid. mp 193–195° C. $^1$HNMR (250 MHz, CDCl$_3$)δ 1.08 (6H, s), 2.41 (2H, s), 2.78 (3H, s) 2.97 (2H, s), 6.88 (1H, br s), 7.49 (1H, br s). MS (ES$^+$) 254 (M+1).

Step 3: 1-(Thiazol-2-yl)-3,6,6-trimethyl-4,5,6,7-tetrahydrobenzo[c]thiophen-4-one In the same way as that described in Example 6, Step 3, using 3,6,6-trimethyl-4,5,6,7-tetrahydrobenzo[c]thiophen-4-one-1-thiocarboxamide, the thiazole (186 mg, 40%) was isolated as a colourless solid. mp 98–100° C.

Found: C, 60.93; H, 5.35; N, 5.11%. C$_{14}$H$_{15}$NO$_2$S$_2$ requires: C, 60.62; H, 5.45; N, 5.05%. $^1$HNMR (360 MHz, CDCl$_3$)δ 1.17 (6H, s), 2.45 (2H, s), 2.82 (3H, s), 2.93 (2H, s), 7.34 (1H, d, J=3.2 Hz), 7.83 (1H, d, J=3.2 Hz). MS (ES$^+$) 278 (M+1).

EXAMPLE 18

3-Benzyl-6,6-dimethyl-1-(thiazol-2-yl)-4,5,6,7-tetrahydrobenzo[c]thiophen-4-one

Step 1: 3-Benzyl-1-cyano-6,6-dimethyl-4,5,6,7-tetrahydrobenzo[c]thiophen-4-one

In the same way as that described in Example 6, Step 1, using benzylmagnesium bromide, the title compound (360 mg, 20%) was isolated as a colourless solid. $^1$HNMR (360 MHz, CDCl$_3$)δ 1.09 (6H, s), 2.46 (2H, s), 2.85 (2H, s), 4.60 (2H, s), 7.26–7.34 (5H, m).

Step 2: 3-Benzyl-6,6-dimethyl-4,5,6,7-tetrahydrobenzo[c]thiophen-4-one-1-thiocarboxamide In the same way as that described in Example 6, Step 2, using 3-benzyl-1-cyano-6,6-dimethyl-4,5,6,7-tetrahydrobenzo[c]thiophen-4-one, the thioamide (470 mg, 100%) was isolated as a yellow solid. mp 183–185° C.

Found: C, 63.25; H, 5.57; N, 4.21%. C$_{18}$H$_{19}$NOS$_2$. 0.6 (H$_2$O) requires: C, 63.53; H, 5.98; N, 4.12%. $^1$HNMR (250 MHz, CDCl$_3$)δ 1.09 (6H, s), 2.44 (2H, s), 3.00 (2H, s), 4.57 (2H, s), 6.82 (1H, br s), 7.20–7.36 (5H, m), 7.42 (1H, br s), MS (ES$^+$) 330 (M+1).

Step 3: 3-Benzyl-6,6'-dimethyl-1-(thiazol-2-yl)-4,5,6,7-tetrahydrobenzo[c]thiophen-4-one In the same way as that described in Example 6, Step 3, using 3-benzyl-6,6-dimethyl-4,5,6,7-tetrahydrobenzo[c]thiophen-4-one-1-thiocarboxamide, the thiazole (153 mg, 42%) was isolated as a colourless solid. mp 112–113° C.

Found: C, 68.14; H, 5.28; N, 4.0%. $C_{20}H_{19}NOS_2$ requires: C, 67.95; H, 5.42; N, 3.96%. $^1$HNMR (360 MHz, $CDCl_3$)δ 1.13 (6H, s), 2.48 (2H, s), 2.94 (2H, s), 4.62 (2H, s), 7.21–7.33 (6H, m), 7.79 (1H, d, J=3.3 Hz). MS (ES$^+$) 354 (M+1).

EXAMPLE 19

6,6-Dimethyl-3-methylthio-01-((1-phenylsulphonyl)pyrazol-3-yl)-4,5,6,7-tetrahydrobenzo[c]thiophen-4-one In the same way as that described in Example 5, using benzenesulphonyl chloride, the title compound (51 mg, 49%) was isolated as a colourless solid. mp 200–202° C.

Found: C, 55.58; H, 4.41; N, 6.19%. $C_{20}H_{20}N_2O_3S_3$ requires: C, 55.53; H, 4.66; N, 6.48%. $^1$HNMR (360 MHz, $CDCl_3$)δ 1.04 (6H, s), 2.40 (2H, s), 2.61 (3H, s), 2.80 (2H, s), 6.53 (1H, d, J=2.7 Hz), 7.56 (2H, t, J=7.5 Hz), 7.67 (1H, t, J=7.6 Hz), 8.07 (2H, d, J=7.3 Hz), 8.13 (1H, d, J=2.7 Hz). MS (ES$^+$) 433 (M+1).

EXAMPLE 20

6,6-Dimethyl-3-isopropylthio-1-(2-methyltetrazol-5-yl)-4,5,6,7-tetrahydrobenzo[c]thiophen-4-one

Step 1: 6,6-Dimethyl-3-isopropylthio-1-(tetrazol-5-yl)-4,5,6,7-tetrahydrobenzo[c]thiophen-4-one In the same way as that described in Example 1, Step 1, using 1-cyano-6,6-dimethyl-3-isopropylthio-4,5,6,7-tetrahydrobenzo[c]thiophen-4-one, the tetrazole (360 mg, 62%) was isolated as a yellow solid. mp 228–230° C.

Found: C, 52.17; H, 5.51; N, 17.34%. $C_{14}H_{18}N_4OS_2$ requires: C, 52.15; H, 5.63; N, 17.38%. $^1$HNMR (360 MHz, $d_6$-DMSO)δ 1.06 (6H, s), 1.46 (6H, d, J=6.6 Hz), 2.43 (2H, s), 3.05 (2H, s), 3.59 (1H, heptet, J=6.6 Hz). MS (ES$^+$) 323 (M+1).

Step 2: 6,6-Dimethyl-3-isopropylthio-1-(2-methyltetrazol-5-yl)-4,5,6,7-tetrahydrobenzo[c]thiophen-4-one In the same way as described in Example 1, Sep 2, the title compound (32 mg, 44%) was isolated as a yellow solid. mp 180–183° C.

Found: C, 53.37; H, 5.73; N, 15.96%. $C_{15}H_{20}N_4OS_2$. 0.2 ($H_2O$) requires: C, 52.98; H, 6.05, N, 16.47%. $^1$HNMR (250 MHz, $d_6$-DMSO)δ 0.98 (6H, s), 1.45 (6H, d, J=6.6 Hz), 2.43 (2H, s), 3.07 (2H, s), 3.59 (1H, heptet, J=6.6 Hz), 4.42 (3H, s). MS (ES$^+$) 337 (M+1).

EXAMPLE 21

1-(1-Acetylpyrazol-3-yl)-6,6-dimethyl-3-methanesulphinyl-4,5,6,7-tetrahydrobenzo[c]thiophen-4-one In the same way as that described in Example 2, using 1-(1-acetylpyrazol-3-yl)-6,6-dimethyl-3-methylthio-4,5,6,7-tetrahydrobenzo[c]thiophen-4-one, the sulphoxide (91 mg. 58%) was isolated as a colourless solid. mp 195–197° C.

Found: C, 55.23; H, 5.05; N, 7.86%. $C_{16}H_{18}N_2O_3S_2$ requires: C, 54.84; H, 5.18; N, 7.99%. $^1$HNMR (360 MHz, $CDCl_3$)δ 1.11 (3H, s), 1.13 (3H, s), 2.43 (1H, d, J=16.6 Hz), 2.53 (1H, d, J=16.6 Hz), 2.76 (3H, s), 2.99 (2H, s), 3.01 (3H, s), 6.67 (1H, d, J=2.9 Hz), 8.33 (1H, d, J=2.9 Hz). MS (ES$^+$) 351 (M+1).

EXAMPLE 22

6,6-Dimethyl-3-[(2-hydroxyethyl)thio]-1-(thiazol-2-yl)-4,5,6,7-tetrahydrobenzo[c]thiophen-4-one

Step 1: 6,6-Dimethyl-3-[(2-hydroxyethyl)thio]-4,5,6,7-tetrahydrobenzo[c]thiophen-4-one-1-thiocarboxamide In the same way as that described in Example 6, Steps 1 and 2, using 2-hydroxyethylmagnesium bromide and 1-cyano-6,6-dimethyl-3-[(2-hydroxyethyl) thio]-4,5,6,7-tetrahydrobenzo[c]thiophen-4-one, the thioamide (511 mg, 100%) was isolated as a pale yellow solid. $^1$HNMR (250 MHz, $d_6$-DMSO)δ 1.05 (6H, s), 2.35 (2H, s), 2.91 (2H, s), 3.17 (2H, t, J=6.3 Hz), 3.71–3.78 (2H, m), 5.16 (1H, t, J=5.5 Hz), 8.70 (1H, br s), 9.85 (1H, br s). MS (ES$^+$) 316 (M+1).

Step 2: 6,6-Dimethyl-3-[(2-hydroxyethyl)thio]-1-(thiazol-2-yl)-4,5,6,7-tetrahydrobenzo[c]thiophen-4-one In the same way as that described in Example 6, Step 3, using 6,6-dimethyl-3-[(2-hydroxyethyl)thio]-4,5,6,7-tetrahydrobenzo[c]thiophen-4-one-1-thiocarboxamide, the thiazole (247 mg, 47%) was isolated as a pale yellow solid. mp 168–170° C.

Found: C, 52.17; H, 5.14; N, 3.99%. $C_{15}H_{17}NS_3O_2$.0.2 ($H_2O$) requires: C, 52.51; H, 5.11; N, 4.08%. $^1$HNMR (360 Hz, $CDCl_3$)δ 1.12 (6H, s), 2.47 (2H, s), 2.90 (2H, s), 3.32 (2H, t, J=5.9 Hz), 4.01 (2H, t, 5.9 Hz), 7.36 (1H, d, J=3.2 Hz), 7.82 (1H, d, J=3.2 Hz). MS (ES$^+$)340 (M+1).

EXAMPLE 23

6,6-dimethyl-3-[(1,1-dimethylethyl)thio]-1-(pyrazol-3-yl)-4,5,6,7-tetrahydrobenzo[c]thiophen-4-one To a stirred solution of 1-(1-acetylpyrazol-3-yl)-6,6-dimethyl-3-methanesulphinyl-4,5,6,7-tetrahydrobenzo[c]thiophen-4-one (73 mg, 0.21 mmol) in THF (7 mL) was added sodium 2-methyl-2-propanethiolate (47 mg, 0.42 mmol). After 90 min more sodium 2-methyl-2-propanethiolate (15 mg, 0.14 mmol) was added, and after a further 30 min the mixture was partitioned between EtOAc (15 mL) and water (10 mL). The organic layer was separated, dried ($Na_2SO_4$) and evaporated. The residue was chromatographed on silica gel, eluting with petrol:EtOAc (1:1), to give the title compound (34 mg, 48%) as a yellow solid. mp 220–222° C.

Found: C, 60.67; H, 6.39; N, 8.31%. $C_{17}H_{22}N_2OS_2$ requires: C, 61.04; H, 6.63; N, 8.37%. $^1$NHMR (360 Hz, $d_6$-DMSO)δ 1.00 (6H, s), 1.45 (9H, s), 2.39 (2H, s), 2.88 (2H, s), 6.54 (1H, br s), 7.87 (1H, br s), 13.07 (1H, br s). MS (ES$^+$) 335 (M+1).

EXAMPLE 24

6,6-Dimethyl-3-methoxy-1-(pyrazol-3-yl)-4,5,6,7-tetrahydrobenzo[c]thiophen-4-one To a stirred solution of 6,6-dimethyl-3-methanesulphinyl-1-(pyrazol-3-yl)-4,5,6,7-tetrahydrobenzo[c]thiophen-4-one (80 mg, 0.26 mmol) in methanol (3 mL) was added a solution of sodium methoxide in methanol (1.0 mL of a 0.5M solution, 0.5 mmol). The solution was heated at 70° C. for 24 h. after which time the mixture was cooled to room temperature and partitioned between EtOAc (2×20 mL) and water (20 mL). The combined organic layers were dried ($Na_2SO_4$) and evaporated. The residue was chromatographed on silica gel, eluting with $CH_2Cl_2$:MeOH (95:5), to give the title compound (11 mg, 15%) as a pale yellow solid. mp 202–204° C. Found: C, 60.24; H, 5.66; N, 10.06%. $C_{14}H_{16}N_2O_2S.0.1$ ($H_2O$) requires: C, 60.45; H, 5.87; N, 10.07%. $^1$HNMR (360 MHz, $d_6$-DMSO)δ 0.98 (6H, s), 2.27 (2H, s), 2.79 (2H, s), 4.03 (3H, s), 6.54 (1H, br s), 7.81 (1H, br s), 12.92 (1H, br s). MS ($ES^+$) 277 (M+1).

EXAMPLE 25

6,6-Dimethyl-1-(4-methyl-1,2,4-triazol-3-yl)-3-methylthio-4,5,6,7-tetrahydrobenzo[c]thiophen-4-one Step 1: 6,6-Dimethyl-3-methylthio-4,5,6,7-tetrahydrobenzo[c]thiophen-4-one-1-carboximidic acid ethyl ester hydrochloride A solution of 1-cyano-6,6-dimethyl-3-methylthio-4,5,6,7-tetrahydrobenzo[c]thiophen-4-one (300 mg, 1.19 mmol) in saturated ethanolic hydrogen chloride solution (50 mL) was stirred at 20° C. for 18 h. The solvent was removed in vacuo and the residue was triturated with ethyl acetate. The product was filtered off, washed with ether and dried to yield the title compound as a white solid (350 mg, 98%). mp 134–136° C. $^1$HNMR (250 MHz, $d_6$-DMSO)δ 1.00 (6H, s), 1.44 (3H, t, J=7.0 Hz), 2.45 (2H, s), 2.67 (3H, s), 3.00 (2H, s), 4.52 (2H, q, J=7.0 Hz). MS ($ES^+$) 298 (M+1).

Step 2: Formic acid[ethoxy-(6,6-dimethyl-3-methylthio-4-oxo-4,5,6,7-tetrahydrobenzo[c]thiophen-1-yl)methylene]hydrazide A solution of 6,6-dimethyl-3-methylthio-4,5,6,7-tetrahydrobenzo[c]thiophene-1-carboximide acid ethyl ester hydrochloride (350 mg, 1.2 mmol) in ethanol (10 mL) was treated with formylhydrazine (70 mg, 1.2 mmol). The mixture was stirred for 16 h at 20° C. then warmed to 50° C. for 4 h. The solvent was removed in vacuo and the residue was purified by chromatographed on silica gel, eluting with methanol:dichloromethane (5.95). The title compound was obtained as a pale yellow oil (150 mg; 38%). $^1$HNMR (360 MHz, $CDCl_3$)δ 1.06 (6H, s), 1.36 (3H, t, J=7.2 Hz), 2.41 (2H, s), 2.60 (3H, s), 2.75 (2H, s), 4.07 (2H, q, J=7.2 Hz), 8.65 (1H, s). MS ($ES^+$) 341 (M+1).

Step 3: 6,6-Dimethyl-1-(4-methyl-1,2,4-triazol-3-yl)-3-methylthio-4,5,6,7-tetrahydrobenzo[c]thiophen-4-one Formic acid[ethoxy-(6,6-dimethyl-3-methylthio-4-oxo-4,5,6,7-tetrahydrobenzo[c]thiophen-1-yl)methylene] hydrazide (150 mg, 0.49 mmol) was dissolved in a solution of methylamine in ethanol (30%, 10 mL) and the mixture heated at 60° C. More methylamine solution (10 mL) was added periodically over 8 h. The solution was evaporated to dryness and the residue purified by chromatographed on silica gel, eluting with methanol:dichloromethane (5:95). The title compound was obtained as a white powder (60 mg, 44%). mp 178–180° C. Found: C, 52.50; H, 5.43; N, 12.73%. $C_{14}H_{17}N_3OS_2.0.8$ ($H_2O$) requires: C, 52.25; H, 5.83; N, 13.06%. $^1$HNMR (360 MHz, $CDCl_3$)δ 1.05 (6H, s), 2.44 (2H, s), 2.62 (3H, s), 2.79 (2H, s), 3.75 (3H, s), 8.28 (1H, s). MS ($ES^+$) 308 (M+1).

EXAMPLE 26

6,6-Dimethyl-1-((4-ethoxycarbonyl)thiazol-2-yl)-3-methylthio-4,5,6,7-tetrahydrobenzo[c]thiophen-4-one Step 1: 6,6-Dimethyl-3-methylthio-4,5,6,7-tetrahydrobenzo[c]thiophen-4-one-1-thiocarboxamide In the same way as in Example 6, Step 2 using 1-cyano-6,6-dimethyl-3-methylthio-4,5,6,7-tetrahydrobenzo[c] thiophen-4-one, the title compound was isolated as a yellow solid (450 mg, 80%). mp 216–218° C. $^1$HNMR (250 MHz, $CDCl_3$)δ 1.09 (6H, s), 2.41 (2H, s), 2.64 (3H, s), 2.91 (2H, s), Found: C, 50.67; H, 5.07; N, 4.88%. $C_{12}H_{15}NOS_3$ requires C, 50.50; H, 5.30; N, 4.91%. MS ($ES^+$) 286 (M+1).

Step 2: 6,6-Dimethyl-1-((4-ethoxycarbonyl)thiazol-2-yl)-3-methylthio-4,5,6,7-tetrahydrobenzo[c]thiophen-4-one In the same way as described in Example 6, Step 3, using 6,6-dimethyl-3-methylthio-4,5,6,7-tetrahydrobenzo[c] thiophen-4-one-1-thiocarboxamide and ethyl bromopyruvate, the title compound was isolated as a pale yellow solid (65 mg, 11%). mp 185–187° C. Found: C, 51.58; H, 4.87; N, 3.53%. $C_{17}H_{19}NO_3S_3.0.75$ ($H_2O$) requires: C, 51.69; H, 5.23; N, 3.55%. $^1$HNMR (360 MHz, $CDCl_3$)δ 1.12 (6H, s), 1.42 (3H, t, J=7.2 Hz), 2.45 (2H, s), 2.65 (3H, s), 2.89 (2H, s), 4.44 (2H, q, J=7.2 Hz), 7.26 (1H, s), 8.13 (1H, s). MS ($ES^+$) 382 (M+1).

EXAMPLE 27

6,6-Dimethyl-1-((4-trifluoromethyl)thiazol-2-yl)-3-methylthio-4,5,6,7tetrahydrobenzo[c]thiophen-4-one In the same way as in Example 26, Step 2 using 1-bromo-3,3,3-trifluoropropanone, the title compound was isolated as a pale yellow solid (85 mg, 26%). mp 165–167° C. Found: C, 47.73; H, 3.91; N, 3.60%. $C_{15}H_{14}F_3NOS_3$ requires: C, 47.73; H, 3.74; N, 3.71%. $^1$HNMR (360 MHz, $CDCl_3$)δ 1.13 (6H, s), 2.47 (2H, s), 2.65 (3H, s), 2.88 (2H, s), 7.72 (1H, s), MS ($ES^+$) 378 (M+1).

EXAMPLE 28

6,6-Dimethyl-3-methylthio-1-(thiazol-2-yl)-4,5,6,7-tetrahydrobenzo[c]thiophen-4-one In the same way as in Example 6, Step 3, using 6,6-dimethyl-3-methylthio-4,5,6,7-tetrahydrobenzo[c]thiophen-4-one-1-thiocarboxamide, the title compound was isolated as a pale yellow solid (350 mg, 65%). mp 149–151° C. Found: C, 52.41; H, 4.64; N, 4.59%. $C_{14}H_{15}NOS_3.0.6$ ($H_2O$) requires: C, 52.79; H, 5.06; N, 4.40%. $^1$HNMR (360 MHz, $CDCl_3$)δ 1.12 (6H, s), 2.46 (2H, s), 2.64 (3H, s), 2.90 (2H, s), 7.35 (1H, d, J=3.6 Hz), 7.81 (1H, d, J=3.6 Hz). MS ($ES^+$) 310 (M+1).

EXAMPLE 29

6,6-Dimethyl-3-dimethylamino-1-((4-ethoxycarbonyl)thiazol-2-yl)-4,5,6,7-tetrahydrobenzo[c]thiophen-4-one 6,6-Dimethyl-1-((4-ethoxycarbonyl)thiazol-2-yl)-4,5,6,7-tetrahydrobenzo[c]thiophen-4-one (100 mg, 0.26 mmol), was dissolved in a solution of dimethylamine in ethanol (30%, 5 mL). The solution was heated in a sealed tube for 3 days at 50° C. The solvent was removed in vacuo and the residue was purified by chromatographed on silica gel, eluting with ethyl acetate:hexane (1:3). The title compounds was isolated as a colourless solid (43 mg, 43%). mp 120–122° C. Found: C, 56.13; H, 5.76; N, 6.53%. $C_{18}H_{22}N_2O_3S_2.0.4$ ($H_2O$) requires: C, 56.05; H, 5.96; N, 6.26%. $^1$HNMR (360 MHz, $CDCl_3$)δ 1.11 (6H, s), 1.41 (3H, t, J=7.2 Hz), 2.40 (2H, s), 2.84 (2H, s), 3.16 (6H, s), 4.42 (2H, q, J=7.2 Hz), 8.03 (1H, s). MS ($ES^+$) 379 (M+1).

EXAMPLE 30

1-((4-Acetyl)thiazol-2-yl)-6,6-dimethyl-3-methylthio-4,5,6,7-tetrahydrobenzo[c]thiophen-4-one In the same way as described in Example 26, Step 2, using 1-bromo-2,3-butanedione, the title compound was isolated as a beige solid (0.21 g, 34%). mp 195–197° C. Found: C, 54.36; H, 4.57; N, 3.91%. $C_{16}H_{17}NO_2S_3$ requires: C, 54.67; H, 4.87; N, 3.98%. $^1$HNMR (360 MHz, $CDCl_3$)δ 1.12 (6H, s), 2.46 (2H, s), 2.67 (3H, s), 2.71 (3H, s), 2.90 (2H, s), 8.10 (1H, s). MS ($ES^+$) 352 (M+1).

EXAMPLE 31

6,6-Dimethyl-1-((4-methyl)thiazol-2-yl)-3-methylthio-4,5,6,7-tetrahydrobenzo[c]thiophen-4-one In the same was as Example 26, Steps 1 and 2, using isopropylmagnesium bromide an chloroacetone, the title compound was isolated as a beige solid (0.11 g, 18%). mp 183–185° C. Found: C, 54.57; H, 5.06; N, 4.36%. $C_{15}H_{17}NOS_3.0.4(H_2O)$ requires: C, 54.78; 5.39; N, 4.26%. $^1$HNMR (360 MHz, $CDCl_3$)δ 1.11 (6H, s), 2.44 (2H, s), 2.48 (3H, s), 2.64 (3H, s), 2.86 (2H, s), 6.89 (1H, s). MS ($ES^+$) 324 (M+1).

EXAMPLE 32

6,6-Dimethyl-3-isopropylthio-1-(thiazol-2-yl)-4,5,6,7-tetrahydrobenzo[c]thiophen-4-one Step 1: 6,6-Dimethyl-3-isopropylthio-4,5,6,7-tetrahydrobenzo[c]thiophen-4-one-1-thiocarboxamide In the same way as in Example 6, Step 2, using 1-cyano-6,6-dimethyl-3-isopropylthio-4,5,6,7-tetrahydrobenzo[c]thiophen-4-one, the title compound was isolated as a yellow solid (1.9 g, 85%). mp 185–187° C. $^1$HNMR (360 MHz, $CDCl_3$)δ 1.08 (6H, s), 1.51 (6H, d, J=7.2 Hz), 2.40 (2H, s), 2.90 (2H, s), 3.59 (1H, heptet, J=7.2 Hz). MS ($ES^+$) 314 (M+1).

Step 2: 6,6-Dimethyl-3-isopropylthio-1-(thiazol-2-yl)-4,5,6,7-tetrahydrobenzo[c]thiophen-4-one In the same way as in Example 6, Step 3, using 6,6-dimethyl-3-isopropylthio-4,5,6,7-tetrahydrobenzo[c]thiophen-4-one-1-thiocarboxamide, the title compound was isolated as a beige solid (0.24 g, 46%). mp 202–204° C. Found: C, 57.18; H, 5.52; N, 4.21%. $C_{16}H_{19}NOS_3$ requires: C, 56.94; H, 5.67; N, 4.15%. $^1$HNMR (250 MHz, $CDCl_3$)δ 1.12 (6H, s), 1.53 (6H, d, J=7.5 Hz), 2.46 (2H, s), 2.88 (2H, s), 3.59 (1H, heptet, J=7.5 Hz), 7.35 (1H, d, J=3.3 Hz), 7.82 (1H, d, J=3.3 Hz). MS ($ES^-$) 338 (M+1).

EXAMPLE 33

6,6-Dimethyl-3-methylthio-1-(pyrazol-4-yl)-4,5,6,7-tetrahydrobenzo[c]thiophen-4-one Step 1: 6,6-Dimethyl-3-methylthio-1-((1-triphenylmethyl)pyrazol-4-yl)-4,5,6,7-tetrahydrobenzo[c]thiophen-4-one To a solution of 1-bromo-6,6-dimethyl-3-methylthio-4,5,6,7-tetrahydrobenzo[c]thiophen-4-one (76 mg, 0.25 mmol) in water (3 mL) and ethylene glycol dimethyl ether (5 mL) was added (1-triphenylmethyl)pyrazol-4-yl boronic acid (115 mg, 0.32 mmol) and sodium carbonate (68 mg, 0.64 mmol). The solution was degassed by bubbling nitrogen through it, then tetrakis (triphenylphosphine) palladium (147 mg, 0.12 mmol) was added and the mixture refluxed for 10 h. The solution was then diluted with 10% sodium carbonate solution and extracted twice with ethyl acetate (10 mL). The combined extracts were dried ($Na_2SO_4$) and evaporated to dryness. The residue was purified by chromatographed on silica gel, eluting with ethyl acetate:hexane (1:4). The title compound was obtained as a yellow solid (45 mg, 34%). $^1$HNMR (360 MHz, $CDCl_3$)δ 1.01 (6H, s), 2.37 (2H, s), 2.50–2.58 (5H, m), 7.17–7.25 (6H, m), 7.33–7.35 (9H, m), 7.43, (1H, s), 7.75 (1H, s).

Step 2: 6,6-Dimethyl-3-methylthio-1-(pyrazol-4-yl)-4,5,6,7tetrahydrobenzo[c]thiophen-4-one 6,6-Dimethyl-3-methylthio-1-((1-triphenylmethyl) pyrazol-4-yl)-4,5,6,7-tetrahydrobenzo[c]thiophen-4-one (35 mg, 0.065 mmol) was dissolved in 98% formic acid (1 mL) and stirred at room temperature for 4 h. The solution was diluted with water and extracted with ethyl acetate (2×5 mL). The extracts were washed with dilute potassium carbonate solution and brine, then dried ($Na_2SO_4$). After evaporation to dryness, the residue was washed twice with diethyl ether to yield the title compound as a yellow powder (10 mg, 52%). mp 213–215° C. $^1$HNMR (360 MHz, $CDCl_3$)δ 1.05 (6H, s), 2.41 (2H, s), 2.60 (3H, s), 2.68 (2H, s), 7.25 (1H, s), 7.71 (1H, s). MS ($ES^+$) 293 (M+1).

EXAMPLE 34

6,6-Dimethyl-3-methylthio-1-(pyrrol-2-yl)-4,5,6,7-tetrahydrobenzo[c]thiophen-4-one Step 1: 6,6-Dimethyl-3-methylthio-1-((1-tert-butyloxycarbonyl)pyrrol-2-yl)-4,5,6,7-tetrahydrobenzo[c]thiophen-4-one In the same was as in Example 33, Step 1, using (1-tert-butyloxycarbonyl)pyrrol-2-yl boronic acid, the title compound was isolated as a pale yellow solid (80 mg, 20%). mp 165–167° C. Found: C, 60.85; H, 6.36, N, 3.55%. $C_{20}H_{25}NO_3S_2$ requires: C, 60.79; H, 6.48; N, 3.54%. $^1$HNMR (360 MHz, $CDCl_3$)δ 1.00 (6H, s), 1.42 (9H, s), 2.37 (2H, s), 2.45 (2H, s), 2.57 (3H, s), 6.23–6.26 (2H, m), 7.41 (1H, t, J=2.2 Hz). MS ($ES^+$) 392 (M+1).

Step 2: 6,6-Dimethyl-3-methylthio-1-(pyrrol-2-yl)-4,5,6,7-tetrahydrobenzo[c]thiophen-4-one 6,6-Dimethyl-3-methylthio-1-((1-tert-butyloxycarbonyl) pyrrol-2-yl)-4,5,6,7-tetrahydrobenzo[c]thiophen-4-one (80 mg, 0.20 mmol) was dissolved in trifluoracetic acid (5 mL) and allowed to stand at 20° C. for 30 min. The solvent was removed in vacuo and the residue dissolved in ethyl acetate. The solution was washed with dilute sodium carbonate solution, water and brine and dried (Na$_2$SO$_4$). The solution was evaporated to dryness and the residue purified by chromatographed on silica gel, eluting with ethyl acetate-:hexane (1:4). The title compound was isolated as a yellow solid (35 mg, 59%). mp 159–197° C. Found: C, 61.64; H, 6.05; N, 4.68%. C$_{15}$H$_{17}$NOS$_2$ requires: C, 61.82; H, 5.88; N, 4.81%. $^1$HNMR (360 MHz, CDCl$_3$)δ 1.04 (6H, s), 2.40 (2H, s), 2.59 (3H, s), 2.73 (2H, s), 6.30–6.33 (2H, m), 6.85–6.88 (1H, m), 8.23 (1H, br s). MS (ES$^+$) 292 (M+1).

EXAMPLE 35

6,6-Dimethyl-3-methylthio-1-(pyrid-2-yl)-4,5,6,7-tetrahydrobenzo[c]thiophen-4-one 1-Bromo-6,6-dimethyl-3-methylthio-4,5,6,7-tetrahydrobenzo[c]thiophen-4-one (300 mg, 1 mmol) was dissolved in dioxane (25 mL), and 2-(tri-n-butylstannyl)pyridine (550 mg, 1.35 mmol) was added. The solution was degassed with nitrogen then tetrakis (tri-phenylphosphine) palladium (30 mg, 0.025 mmol) was added and the solution refluxed for 16 h. The solvent was then removed in vacuo and the residue triturated with a mixture of ethyl acetate and hexane (1:3). After filtration the solid product was washed with a little diethyl ether to give the title compound as a white solid (170 mg, 57%). mp 217–220° C. Found: C, 63.02; H, 5.64; N, 4.47%. C$_{16}$H$_{17}$NOS$_2$ requires; C, 63.36; H, 5.61; N, 4.62%. $^1$HNMR (250 MHz, CDCl$_3$)δ 1.08 (6H, s), 2.44 (2H, s), 2.65 (3H, s), 2.93 (2H, s), 7.18 (1H, m), 7.47 (1H, d, J=8 Hz), 7.71–7.77 (1H, m), 8.61–8.63 (1H, m). MS (ES$^+$) 304 (M+1).

EXAMPLE 36

6,6-Dimethyl-3-((2-hydroxyethyl)thio)-1-(pyrid-2-yl)-4,5,6,7-tetrahydrobenzo[c]thiophen-4-one Step 1: 6,6-Dimethyl-3-methanesulphinyl-1-(pyrid-2-yl)-4,5,6,7-tetrahydrobenzo[c]thiophen-4-one 6,6-Dimethyl-3-methylthio-1-(pyrid-2-yl)-4,5,6,7-tetrahydrobenzo[c]thiophen-4-one (200 mg, 0.66 mmol) was dissolved in CH$_2$Cl$_2$ (20 mL) and cooled to −78° C. Meta-chloroperoxybenzoic acid (82 mg of 70% (w/w); 0.66 mmol) was dissolved in CH$_2$Cl$_2$ (5 mL) and added dropwise to the solution, which was allowed to stir at −50° C. for 1 h, then warmed to room temperature. The mixture was diluted with dichloromethane and washed with saturated sodium hydrogen carbonate solution, water and brine. After drying (Na$_2$SO$_4$), the solution was evaporated to dryness and the residue was purified by chromatography on silica gel, eluting with ethyl acetate:hexane (1:1). The title compound was isolated as a white solid (160 mg, 79%). $^1$HNMR (360 MHz, CDCl$_3$)δ 1.08 (3H, s), 1.11 (3H, s), 2.43 (1H, d, J=18 Hz), 2.53 (1H, d, J=18 Hz), 3.00 (3H, s), 3.03 (2H, s), 7.24–7.28 (1H, m), 7.52–7.54 (1H, m), 7.76–7.80 (1H, m), 8.64–8.66 (1H, m). MS (ES$^+$) 320 (M+1).

Step 2: 6,6-Dimethyl-3-((2-hydroxyethyl)thio)-1-(pyrid-2-yl)-4,5,6,7-tetrahydrobenzo[c]thiophen-4-one 6,6-Dimethyl-3-methanesulphinyl-1-(pyrid-2-yl)-4,5,6,7-tetrahydrobenzo[c]thiophen-4-one (160 mg, 0.5 mmol) was suspended in ethanol (5 mL) and 4M sodium hydroxide solution (138 μL, 0.55 mmol) was added. 2-Mercaptoethanol (43 mg, 0.55 mmol) was added and the suspension was stirred at 20° C. for 2 h. After this time, further 2-mercaptoethanol (10 mg, 0.12 mmol) and 4M sodium hydroxide solution (35 μL, 0.12 mmol) was added and the mixture stirred for a further 2 h. The mixture was then diluted with ethyl acetate and 1M HCL (1 mL) was added. The ethyl acetate layer was washed with water, dried (Na$_2$SO$_4$), then evaporated to dryness. The residue was purified by chromatographed on silica gel, eluting with ethyl acetate, to yield the title compound as a pale yellow solid (58 mg, 36%). mp 175–177° C. Found: C, 61.18; H, 5.62; N, 3.97%. C$_{17}$H$_{19}$NO$_2$S$_2$ requires: C, 61.26; H, 5.70; N, 4.20%. $^1$HNMR (360 MHz, CDCl$_3$)δ 1.08 (6H, s), 2.45 (2H, s), 2.93 (2H, s), 3.33 (2H, t, J=7.2 Hz), 3.98–4.02 (2H, m), 7.16–7.20 (1H, m), 7.46–7.49 (1H, m), 7.72–7.76 (1H, m), 8.64–8.66 (1H, m). MS (ES$^+$) 334 (M+1).

EXAMPLE 37

3-Methylthio-1-(thiazol-2-yl)-4-oxo-5,6,7,8-tetrahydro-4H-cyclohepta[c]thiophene Step 1: 1-Cyano-3-methylthio-4-oxo-5,6,7,8-tetrahydro-4H-cyclohepta[c]thiophene Cycloheptan-1,3-dione (0.5 g, 4 mmol) was dissolved in DMF (10 mL) and cooled to 0° C. Sodium hydride (0.48 g of 60% dispersion in oil, 12 mmol) was added and the suspension stirred at 0–5° C. for 30 min. Carbon disulphide (0.45 g, 6 mmol) was added in one portion and the solution was stirred at 0–5° C. for 30 min. Methyl iodide (0.66 g, 4.4 mmol) was added in one portion and the mixture stirred at room temperature for 30 min. After cooling to 0–5° C., bromoacetonitrile (0.27 mL, 4.4 mmol) was added in one portion and the mixture was stirred at room temperature for 30 min. The mixture was then poured into water, extracted with ethyl acetate and the extracts dried (Na$_2$SO$_4$). After evaporating to dryness, the residue was purified by chromatographed on silica gel, eluting with ethyl acetate:hexane (1:4) to yield the title compound as a pale yellow solid (280 mg, 32%). $^1$HNMR (360 MHz, CDCl$_3$) δ 1.88–1.96 (4H, m), 2.60 (3H, s), 2.75–2.78 (2H, m), 3.21–3.24 (2H, m). MS (ES$^+$) 296 (M+1).

Step 2: 3-Methylthio-4-oxo-5,6,7,8-tetrahydro-4H-cyclohepta[c]thiophene-1-thiocarboxamide In the same was as described in Example 6, Step 2, using 1-cyano-3-methylthio-4-oxo-5,6,7,8-tetrahydro-4H-cyclohepta[c]thiophene, the title compound was isolated as a yellow solid (0.22 g, 68%). $^1$HNMR (250 MHz, CDCl$_3$) δ 1.85–1.90 (4H, m), 2.58 (3H, s), 2.71–2.75 (2H, m), 3.13–3.18 (2H, m). MS (ES$^+$) 272 (M+1).

Step 3: 3-Methylthio-1-(thiazol-2-yl)-4-oxo-5,6,7,8-tetrahydro-4H-cyclohepta[c]thiophene In the same way as described in Example 6, Step 3, using 3-methylthio-4-oxo-5,6,7,8-tetrahydro-4H-cyclohepta[c]thiophene-1-thiocarboxamide, the title compound was isolated as a pale pink solid (110 mg, 46%). mp 143–145° C. Found: C, 52.85; H, 4.39; N, 4.67%. C$_{13}$H$_{13}$NOS$_3$ requires: C, 52.85; H, 4.44; N, 4.67%. $^1$HNMR (360 MHz, CDCl$_3$) δ 1.88–2.04 (4H, m), 2.60 (3H, s), 2.75–2.78 (2H, m), 3.21–3.24 (2H, m), 7.34 (1H, d, J=3.6 Hz), 7.82 (1H, d, J=3.6 Hz). MS (ES$^+$) 296 (M+1).

EXAMPLE 38

6,6-Dimethyl-3-methylthio-1-(3-methyl-1,2,4-oxadiazol-5-yl)-4,5,6,7-tetrahydrobenzo[c]thiophen-4-one To a solution of 6,6-dimethyl-3-methylthio-4,5,6,7-tetrahydrobenzo[c]thiophen-4-one-1-carboxylic acid (1.0 g, 3.7 mmol) in dioxan (90 mL) was added carbonyldiimidazole (0.6 g, 3.7 mmol) and the mixture stirred at 20° C. for 30 min. Acetamide oxime (0.41 g, 5.5 mmol) was added and the mixture was heated at 100° C. for 48 h. The solution was evaporated to dryness and the residue was purified by chromatographed on silica gel, eluting with ethyl acetate-:hexane (2:3) to yield the title compound as a pale yellow solid (0.1 g, 9%). mp 177–180° C. Found: C, 54.90; H, 5.05; N, 8.71%. $C_{14}H_{16}N_2O_2S_2$ requires: C, 54.52; H, 5.23; N, 9.08%. $^1$HNMR (250 MHz, $CDCl_3$) δ 1.11 (6H, s), 2.45–2.47 (5H, m), 2.65 (3H, s), 3.11 (2H, s). MS ($ES^+$) 309 (M+1).

EXAMPLE 39

6,6-Dimethyl-3-methylthio-1-(3-isopropyl-1,2,4-oxadiazol-5-yl)-4,5,6,7-tetrahydrobenzo[c]thiophen-4-one In the same way as in Example 38, using 2-methylpropionamide oxime, the title compound was isolated as a white solid (990 mg, 80%). mp 172–175° C. Found: C, 56.50; H, 5.94; N, 7.89%. $C_{16}H_{20}N_2O_2S_2 0.25$ ($H_2O$) requires: C, 57.12; H, 5.99; N, 8.33%. $^1$HNMR (250 MHz, $CDCl_3$) δ 1.10 (6H, s), 1.38 (6H, d, J=7.5 Hz), 2.45 (2H, s), 2.65 (3H, s), 3.10 (2H, s), 3.14 (1H, heptet, J=7.5 Hz). MS ($ES^+$) 337 (M+1).

EXAMPLE 40

6,6-Dimethyl-1-(4-benzyl-1,2,4-triazol-3-yl)-3-methylthio-4,5,6,7-tetrahydrobenzo[c]thiophen-4-one In the same way as in Example 25, Step 3, using benzylamine, the title compound was isolated as a yellow solid (50 mg, 8%). mp 206–208° C. Found: C, 61.51; H, 5.99; N, 9.68%. $C_{20}H_{21}N_3OS_2.0.5$ ($H_2O$) requires: C, 61.20; H, 5.65; N, 10.07%. $^1$HNMR (250 MHz, $CDCl_3$) δ 0.98 (6H, s), 2.40 (2H, s), 2.57 (3H, s), 2.63 (2H, s), 5.26 (2H, s), 7.04–7.12 (2H, m), 7.33–7.35 (3H, m). MS ($ES^+$) 384 (M+1).

EXAMPLE 41

6,6-Dimethyl-3-methylthio-1-(1-methyl-1,2,4-triazol-3-yl)-4,5,6,7-tetrahydrobenzo[c]thiophen-4-one 6,6-Dimethyl-3-methylthio-4,5,6,7-tetrahydrobenzo[c]thiophen-4-one-1-carboximidic acid ethyl ester (1.0 g, 3.37 mmol) was dissolved in ethanol (60 mL) and methyl hydrazine (0.16 g, 3.37 mmol) was added. The solution was heated at 50° C. for 7 h then evaporated to dryness and the residue was taken up in formic acid (20 mL). The solution was heated at 100° C. for 16 h then evaporated to dryness. The residue was dissolved in $CH_2Cl_2$ and washed with saturated potassium carbonate solution, then evaporated to dryness. The crude product was purified by chromatographed on silica gel, eluting with ethyl acetate to yield the title compound as a yellow solid (0.15 g, 15%). mp 146–148° C. Found: C, 54.55; H, 5.46; N, 13.27%. $C_{14}H_{17}N_3OS_2$ requires; C,54.70; H, 5.77; N, 13.27%. $^1$HNMR (250 MHz, $CDCl_3$) δ 1.05 (6H, s), 2.44 (2H, s), 2.63 (3H, s), 2.74 (2H, s), 3.96 (3H, s), 7.98 (1H, s). MS ($ES^+$) 308 (M+1).

EXAMPLE 42

6,6-Dimethyl-3-methylthio-1-(oxazolidin-2-yl)-4,5,6,7-tetrahydrobenzo[c]thiophen-4-one To a solution of 6,6-dimethyl-3-methylthio-4,5,6,7-tetrahydrobenzo[c]thiophen-4-one-1-caboximidic acid ethyl ester (0.3 g, 0.89 mmol) in ethanol (20 mL) was added ethanolamine (0.06 g, 0.8 mmol) and diisopropylethylamine (0.23 g, 1.8 mmol). The mixture was heated at 60° C. for 8 h, then the solvent was removed in vacuo. The residue was triturated with ethyl acetate and the solid product collected by filtration, to yield the title compound as a colourless solid (50 mg, 19%). mp 190–193° C. Found: C, 56.97; H, 5.51; N, 4.75%. $C_{14}H_{17}NO_2S_2$ requires: C, 56.92; H, 5.80; N, 4.74%. $^1$HNMR (250 MHz, $CDCl_3$), δ 1.06 (6H, s), 2.40 (2H, s), 2.60 (3H, s), 3.01 (2H, s), 4.04 (2H, t, J=10 Hz), 4.42 (2H, t, J=10 Hz). MS ($ES^+$) 296 (M+1).

EXAMPLE 43

3-Methylthio-1-(oxazol-2-yl)-4,5,6,7-tetrahydrobenzo[c]thiophen-4-one

In a similar way to that in Example 35, using 1-bromo-3-methylthio-4,5,6,7-tetrahydrobenzo[c]thiophen-4-one and 2-(tri-n-butylstannyl)oxazole, the title compound was isolated as a pale yellow solid (35 mg, 37%). mp 157–159° C. Found: C, 54.0; H, 3.7; N, 5.6%. $C_{12}H_{11}NO_2S_2$ requires: C, 54.32; H, 4.18; N, 5.28%. $^1$HNMR (250 MHz, $CDCl_3$) δ 2.05–2.16 (2H, m), 2.56–2.61 (2H, m), 2.63 (3H, s), 3.20–3.25 (2H, m), 7.20 (1H, s), 7.66 (1H, s). MS ($ES^+$) 266 (M+1).

EXAMPLE 44

6,6-Dimethyl-3-methylthio-1-(pyrazin-2-yl)-4,5,6,7-tetrahydrobenzo[c]thiophen-4-one In the same way as in Example 35, using 2-(tri-n-butylstannyl)pyrazine, the title compound was isolated as a pale yellow solid (90 mg, 30%). mp 208–210° C. Found: C, 58.53; H, 5.11; N, 8.38%. $C_{15}H_{16}N_2OS_2.0.3$ ($H_2O$) requires: C, 58.15; H, 5.40; N, 8.78%. $^1$HNMR (250 MHz, $CDCl_3$) δ 1.10 (6H, s), 2.46 (2H, s), 2.66 (3H, s), 2.98 (2H, s), 8.43 (1H, d, J=2.5 Hz), 8.56 (1H, d, J=2.5 Hz), 8.81 (1H, s). MS ($ES^+$) 305 (M+1).

EXAMPLE 45

6,6-Dimethyl-3-methylthio-1-(pyrimidin-5-yl)-4,5,6,7-tetrahydrobenzo[c]thiophen-4-one In the same way as in Example 33, Step 1, using pyrimidin-5-yl boronic acid, the title compound was isolated as a pale yellow solid (10 mg, 7%). mp 158–161° C. Found: C, 55.56; H, 4.59; N, 7.78%. $C_{15}H_{16}N_2OS_2.1.2$ ($H_2O$) requires: C, 55.26; H, 5.01; N, 8.05 %. $^1$HNMR (250 MHz, $CDCl_3$) δ 1.05 (6H, s), 2.45 (2H, s), 2.64 (3H, s), 2.76 (2H, s), 8.81 (2H, s). 9.17 (1H, s). MS ($ES^+$) 305 ((M+1).

EXAMPLE 46

6,6-Dimethyl-1-(imidazolin-2yl)-3-methylthio-4,5,6,7-tetrahydrobenzo[c]thiophen-4-one In the same was as described in Example 42, using 1,2-diaminoethane, the title compound was isolated as a white solid (90 mg, 70%). mp 172–175° C. Found: C, 43.76; H, 4.93; N, 6.85%. $C_{14}H_{18}N_2OS_2.2HCl.H_2O$ requires: C, 43.64; H, 5.25; N, 7.27%. $^1$HNMR (250 MHz, $CDCl_3$) δ 1.08 (6H, s), 2.42 (2H, s), 2.63 (3H, s), 2.92 (2H, s), 3.83 (4H, s). MS ($ES^+$) 295 (M+1).

EXAMPLE 47

3-Methylthio-6,6-spirocyclohexyl-1-(thiazol-2yl)-4,5,6,7-tetrahydrobenzo[c]thiophen-4-one Step 1: 1-Cyano-3-methylthio-6,6-spirocyclohexyl-4,5,6,7-tetrahydrobenzo[c]thiophen-4-one In the same way as described in Example 37, Step 1, using 5,5-spirocyclohexyl cyclohexane-1,3-dione, the title compound was isolated as a yellow solid (0.27 g, 33%). $^1$HNMR (250 MHz, CDCl$_3$) δ 1.18–1.47 (10H, m), 2.49 (2H, s), 2.62 (3H, s), 2.87 (2H, s).

Step 2: 3-Methylthio-6,6-spirocyclohexyl-4,5,6,7-tetrahydrobenzo[c]thiophen-4-one-1-thiocarboxamide In the same way as described in Example 37, Step 2, using 1-cyano-3-methylthio-6,6-spirocyclohexyl-4,5,6,7-tetrahydrobenzo[c]thiophen-4-one, the title compound was isolated as a yellow solid (0.29 g, 100%). $^1$HNMR (250 MHz, CDCl$_3$) δ 1.40–1.60 (10H, m), 2.50 (2H, s), 2.63 (3H, s), 2.95 (2H, s). MS (ES$^-$) 326 (M+1).

Step 3: 3-Methylthio-6,6-spirocyclohexyl-1-(thiazol-2-yl)-4,5,6,7-tetrahydrobenzo[c]thiophen-4-one In the same way as described in Example 37, Step 3, using 3-methylthio-6,6-spirocyclohexyl-4,5,6,7-tetrahydrobenzo[c]thiophen-4-one-1-thiocarboxamide, the title compound was isolated as cream-coloured solid (130 mg, 41%). mp 164–167° C. Found: C, 58.11; H, 5.37; N, 3.94%. C$_{17}$H$_{19}$NOS$_3$ requires: C, 58.42; H, 5.48; N, 4.01%. $^1$HNMR (250 MHz, CDCl$_3$) δ 1.40–1.60 (10H, m), 2.53 (2H, s), 2.64 (3H, s), 2.95 (2H, s), 7.35 (1H, d, J=3.3 Hz), 7.82 (1H, d, J=3.3 Hz). MS (ES$^+$) 350 (M+1).

EXAMPLE 48

6,6-Dimethyl-1-(3-(N-methylaminocarbonyl)thiazol-2-yl)-3-methylthio-4,5,6,7-tetrahydrobenzo[c]thiophen-4-one 6,6-Dimethyl-1-((4-ethoxycarbonyl)thiazol-2-yl)-3-methylthio-4,5,6,7-tetrahydrobenzo[c]thiophen-4-one (100 mg, 0.26 mmol) and methylamine (5 mL of a 33% (w/v) solution in ethanol) was stirred for 3h. After this time the solvent was evaporated and the solid triturated with ether. The title compound (65 mg, 69%) was isolated as a pale yellow solid. mp 202–204° C. $^1$HNMR (360 MHz, CDCl$_3$) δ 1.13 (6H, s), 2.47 (2H, s), 2.66 (3H, s), 2.87 (2H, s), 3.05 (2H, d, J=5.2 Hz), 8.08 (1H, s). MS (ES$^+$) 367 (M+1).

EXAMPLE 49

6,6-Dimethyl-3-methylthio-1-(thiazol-5-yl)-4,5,6,7-tetrahydrobenzo[c]thiophen-4-one In the same way as described in Example 35, using 5-(tri-n-butylstannyl)thiazole and dichlorobistriphenylphosphine palladium, the title compound (20 mg, 20% was isolated as a yellow solid. mp 138–140° C. $^1$ HNMR (250 MHz, CDCl$_3$) δ 1.07 (6H, s), 2.44 (2H, s), 2.62 (3H, s), 2.75 (2H, s), 7.90 (1H, s), 8.80 (1H, s). MS (ES$^+$) 310 (M+1).

EXAMPLE 50

6,6-Dimethyl-3-tert-butylamino)-1-(pyrazol-3-yl)-4,5,6,7-tetrahydrobenzo[c]thiophen-4-one A solution of 6,6-dimethyl-3-methanesulphinyl-1-(pyrazol-3-yl)-4,5,6,7-tetrahydrobenzo[c]thiophen-4-one (100 mg, 0.33 mmol) and tert-butylamine (0.69 mL, 6.6 mmol) in butanol (6 mL) was heated at 150° C., in a sealed tube, for 5 days. After this time the solvent was removed in vacuo and the residue partitioned between EtOAc (20 mL) and water (2×20 mL). The organic layer was separated, dried (MgSO$_4$) and evaporated. The residue was chromatographed on silica gel, eluting with petrol:EtOAc (2:1), to give the title compound (9 mg, 9%) as a beige solid. mp 260–262° C. $^1$H NMR (360 MHz, CDCl$_3$) δ 1.06 (6H, s), 1.48 (9H, s), 2.33 (2H, s), 2.71 (2H, s), 6.41 (1H, d, J=2.3 Hz), 7.59 (1H, d, J=2.3 Hz), 9.47 (1H, br, s). MS (ES$^+$). 318 (M+1).

EXAMPLE 51

3-Cyclobutoxy-6,6-dimethyl-1-(pyrazol-3-yl)-4,5,6,7-tetrahydrobenzo[c]thiophen-4-one To a solution of 6,6-dimethyl-3-methanesulphinyl-1-(pyrazol-3-yl)-4,5,6,7-tetrahydrobenzo[c]thiophen-4-one (178 mg, 0.59 mmol) in cyclobutanol (1 mL) and THF (3 mL) was added sodium hydride (70 mg of a 60% dispersion in oil, 1.76 mmol). After effervescence had ceased the mixture was heated at 95° C. for 2h before the solvent was evaporated. The residue was partitioned between EtOAc (20 mL) and water (20 mL) and the organic layer separated, dried (Na$_2$SO$_4$) and evaporated. The residue was chromatographed on silica gel, eluting with petrol:EtOAc (1:1) to give the title compound (22 mg, 12%) as a pale yellow solid. mp 202–204° C. Found: C, 62.48; H, 6.24; N, 8.49%. C$_{17}$H$_{20}$N$_2$O$_2$S .0.5(H$_2$O) requires: C, 62.74; H, 6.50; N, 8.61% $^1$H NMR (360 MHz, CDCl$_3$) δ 1.06 (6H, s), 1.60–1.76 (1H, m), 1.86–1.97 (1H, m), 2.37 (2H, s), 2.38–2.47 (2H, m), 2.50–2.60 (2H, m), 2.79 (2H, s), 4.76 (1H, pentet, J=7.2 Hz), 6.45 (1H, d, J=2.4 Hz), 7.62 (1H, d, J=2.4 Hz). MS (ES$^+$) 317 (M+1).

EXAMPLE 52

6,6-Dimethyl-1-[(3-ethoxycarbonyl)isoxazol-5-yl)-3-methylthio-4,5,6,7-tetrahydrobenzo[c]thiophen-4-one In the same way as that described in Example 35 using 1-bromo-6,6-dimethyl-3-methylthio-4,5,6,7-tetrahydrobenzo[c]thiophen-4-one, 2-(tri-n-butylstannyl)pyridine and dichlorobistriphenylphosphine palladium (II), the title compound (10 mg, 7%) was isolated as a solid. mp 178–179° C. $^1$H NMR (250 MHz, CDCl$_3$) δ 1.10 (6H, s), 1.45 (3H, t, J=7.1 Hz), 2.46 (2H, s), 2.65 (3H, s), 2.87 (2H, s), 4.48 (2H, q, J=7.1 Hz), 6.68 (1H, s). MS (ES$^+$) 366 (M+1).

EXAMPLE 53

6,6-Dimethyl-3-phenoxy-1-(pyrazol-3-yl)-4,5,6,7-tetrahydrobenzo[c]thiophen-4-one To a solution of phenol (116 mg, 1.1 mmol) in THF (10 mL) was added 6,6-dimethyl-3-methanesulphonyl-1-(pyrazol-3-yl)-4,5,6,7-tetrahydrobenzo[c]thiophen-4-one (0.2 g, 0.62 mmol) and NaOH (0.3 mL of a 4M solution, 1.1 mmol). The mixture was heated at reflux overnight. Phenol (50 mg, 0.62 mmol) and NaOH (0.15 mL of a 4M solution, 0.62 mmol) were then added and the mixture heated at reflux for an additional 8 h. The solution was cooled to room temperature, diluted with EtOAc (100 mL) and washed with NaOH (1M, 2×100 mL). The organic layer was separated, dried (Na$_2$SO$_4$) and evaporated. The residue was chromatographed on silica gel, eluting with hexane:EtOAc (2:1) to give the title compound (35 mg, 18%) as a yellow solid. mp 232–234° C. $^1$H NMR (360 MHz, CDCl$_3$) δ 1.10 (6H, s), 2.42 (2H, s), 2.86 (2H, s), 6.43 (1H, d, J=2.3 Hz), 7.20–7.26 (3H, m), 7.37 (1H, d, J=7.3 Hz), 7.39 (1H, d, J=8.7 Hz), 7.59 (1H, d, J=2.3 Hz). MS (ES$^+$) 339 (M+1).

The following process was used to prepare Examples 54–92.

To a suspension of 6,6-dimethyl-3-methanesulphonyl-1-(pyrazol-3-yl)-4,5,6,7-tetrahydrobenzo[c]thiophen-4-one (50 mg, 0.15 mmol) in EtOH (2 mL) was added NaOH (77 μL of a 4M solution, 0.31 mmol) followed by the appropriate thiol (0.31 mmol). The mixture was then stirred at room temperature for 90 min or at 70° C. for 3–72 h. The mixture was then diluted with MeOH:H$_2$O:1MHCl (5:5:1) and poured onto a C-18 Bond Elut cartridge (prewashed with MeOH followed by water). The cartridge was eluted with MeOH:H$_2$O (8 mL) (1:1→1:0) and the product fractions evaporated. The residue was triturated with Et$_2$O to give the appropriate thioether as a solid.

EXAMPLE 54

6,6-Dimethyl-3-pentylthio-1-(pyrazol-3-yl)-4,5,6,7-tetrahydrobenzo[c]thiophen-4one mp. 121–123° C. $^1$H NMR (360 MHz, CDCl$_3$) δ 0.92 (3H, t, J=7.2 Hz). 1.07 (6H, s), 1.18–1.50 (4H, m), 1.84 (2H, pentet, J=7.5 Hz), 2.43 (2H, s), 2.85 (2H, s), 3.07 (2H, t, J=7.3 Hz), 6.48 (1H, d, J=2.3 Hz), 7.64 (1H, d, J=2.3 Hz). MS (ES$^-$) 349 (M+1).

EXAMPLE 55

3-Butylthio-6,6-dimethyl-1-(pyrazol-3-yl)-4,5,6,7-tetrahydrobenzo[c]thiophen-4-one mp. 149–150° C. Found: C, 60.96; H, 6.43; N 8.43%. C$_{17}$H$_{22}$N$_2$OS$_2$ requires: C, 61.04; H, 6.63; N, 8.37%. $^1$H NMR (360 MHz, CDCl$_3$) δ 0.96 (3H, t, J=7.4 Hz), 1.07 (6H, s), 1.52 (2H, sextet, J=7.4 Hz), 1.82 (2H, pentet, J=7.6 Hz), 2.43 (2H, s), 2.85 (2H, s), 3.08 (2H, t, J=7.4 Hz), 6.48 (1H, d, J=2.3 Hz), 7.64 (1H, d, J=2.3 Hz). MS (ES$^+$) 335 (M+1).

EXAMPLE 56

3-[(3-Chloropropyl)thio]-6,6-dimethyl-1-(pyrazol-3-yl)-4,5,6,7-tetrahydrobenzo[c]thiophen-4-one mp 150–151° C. Found: C, 54.29; H, 5.43; N, 7.83%. C$_{16}$H$_{19}$ClN$_2$OS$_2$ requires: C, 54.15; H, 5.40; N, 7.89%. $^1$H NMR (360 MHz, CDCl$_3$) δ 1.08 (6H, s), 2.30 (2H, pentet, J=6.7 Hz), 2.43 (2H, s), 2.86 (2H, s), 3.24 (2H, t, J=7.1 Hz), 3.71 (2H, t, J=6.4 Hz), 6.49 (1H, d, J=2.3 Hz), 7.64 (1H, d, J=2.3 Hz). MS (ES$^+$) 355/357 (M+1).

EXAMPLE 57

6,6-Dimethyl-3-((2-phenylethyl)thio)-1-(pyrazol-3-yl)-4,5,6,7-tetrahydrobenzo[c]thiophen-4-one mp. 173–175° C. Found: C, 65.64; H, 5.64; N, 7.09%. C$_{21}$H$_{22}$N$_2$OS$_2$ requires: C, 65.94; H, 5.80; N, 7.32%. $^1$H NMR (360 MHz, CDCl$_3$) δ 1.08 (6H, s), 2.43 (2H, s), 2.86 (2H, s), 3.12 (2H, t, J=8.5 Hz), 3.33 (2H, t, J=8.5 Hz), 6.49 (1H, d, J=2.3 Hz), 7.25–7.32 (5H, m), 7.64 (1H, d, J=2.3 Hz). MS (ES$^+$) 383 (M+1).

EXAMPLE 58

6,6-Diemthyl-3-propylthio-1-(pyrazol-3-yl)-4,5,6,7-tetrahydrobenzo[c]thiophen-4-one mp. 181–182° C. Found: C, 59.90; H, 5.99; N, 8.64%. C$_{16}$H$_{20}$N$_2$OS$_2$ requires: C, 59.97; H, 6.29; N, 8.74%. $^1$H NMR (360 MHz. CDCl$_3$) δ1.07, (6H, s), 1.10 (3H, t, J=7.3 Hz), 2.43 (2H, s), 2.85 (2H, s), 3.05 (2H, t, J=7.3 Hz), 6.48 (1H, d, J=2.3 Hz), 7.64 (1H, d, J=2.3 Hz). MS (ES$^+$) 321 (M+1).

EXAMPLE 59

6,6-Dimethyl-3-((2-methylbutyl)thio)-1-(pyrazol-3-yl)-4,5,6,7-tetrahydrobenzo[c]thiophen-4-one mp. 158–159° C. Found: C, 62.06; H, 6.86; N, 8.03%. C$_1$–H$_{24}$N$_2$OS$_2$ requires: C,62.03; H, 6.94; N, 8.04%. $^1$H NMR (360 MHz. CDCl$_3$) δ0.95% (3H, t. J=7.4 Hz), 1.07 (6H, s), 1.30–1.40 (1H, m). 1.58–1.68 (1H. m), 1.83–1.94 (1H. m). 2.43 (2H, s). 2.84 (2H, s), 290–2.98 (1H, m). 3.07–3.12 (1H. m). 6.48 (1H, d, J=2.3 Hz), 7.64 (1H, d, J=2.3 Hz). MS (ES$^{34}$ ) 349 )M+1).

EXAMPLE 60

6,6-Dimethyl-1-(pyrazol-3-yl)-3-((2,2,2-trifluoroethyl)thio)-4,5,6,7-tetrahydrobenzo[c]thiophen-4-one mp. 141–142° C. Found: C, 50.02; H, 3.98: N, 7.84%, C$_{17}$H$_{15}$F$_3$N$_2$OS$_2$ requires: C, 49.99; H, 4.20; N, 7.77% $^1$H NMR (360 MHz. CDCl$_3$) δ1.08 (6H. s), 2.45 (2H. s). 2.88 (2H, s). 3.69 (2H. q, J=9.6 Hz). 6.50 (1H. d. J=2.3 Hz), 7.65 (1H. d. J=2.3 Hz). MS (ES$^+$) (M+1).

EXAMPLE 61

6,6-Dimethyl-3-((1-methylpropyl)thio)-1-(pyrazol-3-yl)-4,5,6,7-tetrahydrobenzo[c]thiophen-4-one mp. 151–152° C. Found: C, 61.30; H, 6.64; N, 8.36%. C$_{17}$H$_{22}$N$_2$OS$_2$ requires: C, 61.04; H, 6.63; N, 8.37%. $^1$H NMR (360 MHz, CDCl$_3$) δ1.04–1.09 (9H, m), 1.49 (3H, d, J=6.7 Hz), 1.69–1.78 (1H, m), 1.83–1.92 (1H, m), 2.43 (2H, s), 2.84 (2H, s), 3.36 (1H, sextet, J=6.6 Hz), 6.48 (1H, d, J=2.3 Hz), 7.65 (1H, d, J=2.3 Hz). MS (ES$^+$) 335 (M+1).

EXAMPLE 62

3-((4-Chlorophenyl)thio)-6,6-dimethyl-1-(pyrazol-3-yl)-4,5,6,7-tetrahydrobenzo[c]thiophen-4-one mp. 186–187° C. $^1$H NMR (360 MHz, CDCl$_3$) δ1.09 (6H, s), 2.46 (2H, s), 2.84 (2H, s), 6.40 (1H, d, J=2.3 Hz), 7.42 (2H, d, J=8.5 Hz). 7.58 (1H. d. J=2.3 Hz), 7.64 (2H, d, J=8.5 Hz). MS (ES$^+$) 389 (M+1).

EXAMPLE 63

6,6-Dimethyl-3-((3-fluorophenyl)thio)-1-(pyrazol-3-yl)-4,5,6,7-tetrahydrobenzo[c]thiophen-4-one mp. 264–266° C. Found: C. 60.39: H, 4.35: N, 7.33%. C$_{19}$H$_{17}$FN$_2$OS$_2$ .0.3(H$_2$O) requires: C. 60.39: H. 4.69; N. 7.41%. $^1$H NMR (360 MHz. CDCl$_3$) δ1.10 (6H, s), 2.84 (2H, s), 2.84 (2H. s). 6.41 (1H. d. J=2.3 Hz). 7.16–7.22 (1H. m). 7.40–7.46 (2H, m). 7.48–7.52 (1H. m). 7.58 (1H. d, J=2.3 Hz). MS (ES$^-$) 373 (M+1).

EXAMPLE 64

3-((4-Acetylaminophenyl)thio)-6,6-dimethyl-1-(pyrazol-3-yl)-4,5,6,7-tetrahydrobenzo[c]thiophen-4-one mp. 236–237° C. Found: C, 61.06; H, 4.87; N, 10.54%. C$_{21}$H$_{21}$N$_3$O$_3$S$_2$ requires: C, 61.29; H, 5.14; N, 10.21%. $^1$H NMR (360 MHz, CDCl$_3$) δ1.09 (6H, s), 2.21 (3H, s), 2.46 (2H, s), 2.83 (2H, s), 6.39 (1H, s), 7.26 (1H, br s). 7.50–7.70 (5H, m). MS (ES$^+$) 412 (M+1).

EXAMPLE 65

6,6-dimethyl-3-((4-methoxyphenyl)thio)-1-(pyrazol-3-yl)-4,5,6,7-tetrahydrobenzo[c]thiophen-4-one mp. 227–229° C. Found: C, 62.13; H, 5.03; N, 7.18%. C$_{20}$H$_{20}$N$_2$O$_2$S$_2$ requires: C, 62.47; H, 5.24; N, 7.29%. $^1$H NMR (360 MHz, CDCl$_3$) δ1.09 (6H. s). 2.46 (2H, s), 2.82 (2H. s), 3.86 (3H, s), 6.39 (1H, d, J=2.4 Hz), 6.96 (2H. d. J=8.8 Hz), 7.56 (1H, d, J=2.4 Hz), 7.61 (2H. d. J=8.8 Hz). MS (ES$^+$) 385 (M+1).

EXAMPLE 66

6,6-Dimethyl-3-((1-methylimidazol-2-yl)thio)-1-(pyrazol-3-yl)-4,5,6,7-tetrahydrobenzo[c]thiophen-4-one $^1$H NMR (360 MHz, CDCl$_3$+d$_4$_MeOH) δ1.09 (6H. s). 2.47 (2H. s), 2.83 (2H. s). 3.80 (3H. s). 6.39 (1H, d, J=3.3 Hz). 7.22 (1H. s). 7.24 (1H. s). 7.59 (1H. d. J=3.4 Hz). MS (ES$^+$) 359 (M+1).

EXAMPLE 67

6,6-Dimethyl-3-((thiophen-2-yl)thio)-1-(pyrazol-3-yl)-4,5,6,7-tetrahydrobenzo[c]thiophen-4-one mp. 226–228° C. Found: C, 56.16; H, 4.27; N, 7.55%. C$_{17}$H$_{16}$N$_2$OS$_3$ .0.15(H$_2$O) requires: C, 56.22; H, 4.52; N, 7.71%. $^1$H NMR (360 MHz, CDCl$_3$) δ1.09 (6H, s), 2.46 (2H, s), 2.83 (2H, s), 6.40 (1H, d, J=2.3 Hz), 7.13 (1H, dd, J=5.3 and 3.6 Hz), 7.43 (1H, d, J=3.6 Hz), 7.57–7.61 (2H, m). MS (ES$^+$) 361 (M+1).

EXAMPLE 68

6,6-Dimethyl-3-((imidazol-2-yl)thio)-1-(pyrazol-3yl)-4,5,6,7-tetrahydrobenzo[c]thiophen-4-one mp. 242–245° C. Found: C, 54.99; H, 4.70; N, 15.59%. C$_{16}$H$_{16}$N$_4$OS$_2$ .0.4(H$_2$O) requires: C, 54.65; H, 4.82; N, 15.93%. $^1$H NMR (360 MHz, CDCl$_3$+d$_4$_MeOH) δ1.07 (6H, s), 2.45 (2H, s), 2.80 (2H, s). 6.37 (1H, d, J=2.4 Hz), 7.22 (2H, br s), 7.57 (1H, d, J=2.4 Hz). MS (ES$^+$) 345 (M+1).

EXAMPLE 69

6,6-Dimethyl-3-((4-phenylthiazol-2-yl)-2-(pyrazol-3-yl)-4,5,6,7-tetrahydrobenzo [c]thiophen-4-one mp. 227–228° C. Found: C, 60.44; H, 4.30; N, 9.32%. C$_{22}$H$_{19}$N$_3$OS$_3$ requires: C. 60.39: H. 4.38: N, 9.60%. $^1$H NMR (360 MHz. CDCl$_3$) δ1.00 (6H. s). 2.39 (2H. s), 2.78 (2H, s). 6.34 (1H, d. J=2.3 Hz). 7.16–7.36 (3H. m). 7.49 (1H. d. J=2.3 Hz). 7.54 (1H. s). 7.85–7.88 (2H. m). MS (ES$^-$) 438 (M+1).

EXAMPLE 70

6,6-Dimethyl-1-(pyrazol-3-yl)-3-((1,2,4-triazol-3-yl)thio)-4,5,6,7-tetrahydrobenzo[c]thiophen-4-one mp. 182–184° C. $^1$H NMR (360 MHz, CDCl$_3$+d$_4$_MeOH) δ1.08 (6H, s). 2.46 (2H, s), 2.82 (2H, s), 6.40 (1H, d, J=2.2 Hz), 7.58 (1H, d, J=2.2 Hz), 8.33 (1H, s). MS (ES$^+$) 346 (M+1).

EXAMPLE 71

6,6-Dimethyl-3-((5-methyl-1,3,4-thiadiazol-2-yl)thio)-1-(pyrazol-3-yl)-4,5,6,7-tetrahydrobenzo[c]thiophen-4-one mp. 170–172° C. $^1$H NMR (360 MHz, CDCl$_3$) δ1.10 (6H, s), 2.48 (2H. s), 2.82 (3H, s), 2.90 (2H, s), 6.48 (1H, d, J=2.3 Hz), 7.63 (1H, d. J=2.3 Hz). MS (ES$^+$) 377 (M+1).

EXAMPLE 72

6,6-Dimethyl-3-((4-methyl-1,2,4-triazol-2-yl)thio)-1-(pyrazol-3-yl)-4,5,6,7-tetrahydrobenzo[c]thiophen-4-one mp. 234–236° C. $^1$H NMR (360 MHz. CDCl$_3$+d$_4$_MeOH) δ1.10 (6H. s). 2.48 (2H, s), 2.84 (2H, s). 3.79 (3H, s), 6.40 (1H, d. J=2.1 Hz). 7.59 (1H. d. J=2.1 Hz). 8.47 (1H, s). MS (ES$^+$) 360 (M+1).

EXAMPLE 73

6,6-Dimethyl-3-((5-methylthio-1,3,4-thiadiazol-2-yl)thio)-1-pyrazol-3-yl)-4,5,6,7-tetrahydrobenzo[c]thiophen-4-one mp. 192–194° C. $^1$H NMR (360 MHz, CDCl$_3$) δ1.09 (6H, s), 2.48 (2H, s), 2.82 (3H, s), 2.88 (2H, s), 6.45 (1H, d, J=2.4 Hz), 7.61 (1H, d, J=2.4 Hz). MS (ES$^+$) 409 (M+1).

EXAMPLE 74

3-Benzylthio-6,6-dimethyl-1-(pyrazol-3-yl)-4,5,6,7-tetrahydrobenzo[c]thiophen-4-one mp 215–218° C. Found: C, 62.83; H, 5.47; N, 7.03%. C$_{20}$H$_{20}$N$_2$OS$_2$.0.8 (H$_2$O) requires: C, 62.73; H, 5.69; N, 7.32%.

$^1$H NMR (360 MHz, d$_6$_DMSO) δ0.99 (6H, s), 2.37 (2H, s), 2.83 (2H, s), 4.34 (2H, s), 6.47–6.49 (1H, m), 7.27–7.31 (1H, m), 7.34–7.38 (1H, m), 7.46–7.49 (1H, m), 7.83–7.85 (1H, m). 13.00 (1H, br s). MS (ES$^+$) 369 (M+1).

EXAMPLE 75

3-Cyclopenthylthio-6,6-dimethyl-1-(pyrazol-3-yl)-4,5,6,7-tetrahydrobenzo[c]thiophen-4-one mp 212–214° C. Found: C, 61.36; H, 6.27; N, 7.78%. C$_{18}$H$_{22}$N$_2$OS$_2$.0.4 (H$_2$O) requires: C. 61.12: H. 6.50; N. 7.92%.

$^1$H NMR (360 MHz. d$_6$_DMSO) δ0.99 (6H, s), 1.60–1.80 (6H. m), 2.20–2.30 (2H. m). 2.36 (2H, s). 2.83 (2H, s), 3.66–3.72 (1H. m). 6.49 (1H. d. J=2.3 Hz). 7.84 (1H. br s). 13.02 (1H. br s). MS (ES$^+$) 346 (M+1).

EXAMPLE 76

6,6-Dimethyl-3-((2-methylpropyl)thio)-1-(pyrazol-3-yl)-4,5,6,7-tetrahydrobenzo[c]thiophen-4-one mp 186–188° C.

$^1$H NMR (360 MHz, d$_6$DMSO) δ0.99 (6H, s), 1.05 (6H, d, J=6.6 Hz), 1.98–2.08 (1H, m), 2.37 (2H, s), 2.84 (2H, s), 2.95 (2H, d, J=6.8 Hz). 6.49 (1H, d, J=2.2 Hz), 7.84 (1H, br s), 13.00 (1H, br s). MS (ES$^+$) 335 (M+1).

EXAMPLE 77

6,6-Dimethyl-3-hexylthio-1-(pyrazol-3-yl)-4,5,6,7-tetrahydrobenzo[c]thiophen-4-one mp 134–137° C. Found: C, 62.27; H, 7.28; N, 7.35%. C$_{19}$H$_{26}$N$_2$OS$_2$.0.25 (H$_2$O) requires: C, 62.17; H, 7.28; N, 7.63%.

¹H NMR (360 MHz, d₆-DMSO) δ0.85–0.90 (3H, m), 1.00 (6H. s), 1.26–1.34 (4H. m), 1.40–1.50 (2H, m), 1.60–1.78 (2H, m), 2.37 (2H, s). 2.84 (2H. s). 3.05 (2H, t, J=7.2 Hz), 6.48–6.50 (1H, m), 7.82–7.86 (1H, m), 13.00 (1H, br s). MS (ES⁺) 363 )(M+1).

EXAMPLE 78

6,6-Dimethyl-3-isopropylthio-1-(pyrazol-3-yl)-4,5,6,7-tetrahydrobenzo[c]thiophen-4-one mp 195–198° C. Found: C, 59.29: H, 6.00: N, 8.31%. $C_{16}H_{20}N_2OS_2.0.2$ ($H_2O$) requires: C. 59.30: H. 6.35: N, 8.64%.

¹H NMR (360 MHz, d₆-DMSO) δ0.99 (6H, s), 1.42 (6H, d, J=6.7 Hz). 2.37 (2H, s), 2.84 (2H, s), 3.50–3.58 (1H, m), 6.50 (1H, d, J=2.2 Hz), 7.85 (1H, br s), 13.02 (1H, br s). MS (ES⁺) 320 )M+1).

EXAMPLE 79

6,6-Dimethyl-3-((furan-2-ylmethyl)thio)-1-(pyrazol-3-yl)-4,5,6,7-tetrahydrobenzo[c]thiophen-4-one mp 198–200° C. Found: C, 58.91; H, 490; N, 7.39%. $C_{18}H_{18}N_2O_2S_2.0.5$ ($H_2O$) requires: C, 58.83; H, 4.90; N, 7.62%.

¹H NMR (360 MHz, D₆-DMSO) δ0.99 (6H, s), 2.38 (2H, s), 2.84 (2H, s), 4.40 (2H, s), 6.40–6.45 (2H, m), 6.48–6.52 (1H, m), 7.63 (1H, s), 7.85 (1H, br s). 13.02 (1H, br s). MS (ES⁺) 359 (M+1).

EXAMPLE 80

6,6-Dimethyl-3-((2-hydroxy-1-methylpropyl)thio)-1-(pyrazol-3-yl)-4,5,6,7-tetrahydrobenzo[c]thiophen-4-one mp 171–174° C. Found: C, 56.86; H. 6.12; N, 7.64%. $C_{17}H_{22}N_2O_2S_2.0.5$ ($H_2O$) requires: C, 56.80; H, 6.45; N, 7.79%.

¹H NMR (360 MHz, d₆-DMSO) δ0.98–1.00 (6H, m). 1.14–1.19 (3H. m), 1.36–1.40 (3H, m). 2.37 (2H, s), 2.83 (2H. s). 3.30–3.44 (1H. m), 3.90–3.98 (1H. m). 5.03 and 5.12 (1H. 2xd, J=5.2 Hz), 6.49 (1H. br s). 7.84 (1H. br s). 13.00 (1H, br s). MS (ES⁺) 351 (M+1).

EXAMPLE 81

6,6-Dimethyl-3-((2,3-dihydroxypropyl)thio)-1-(pyrazol-3-yl)-4,5,6,7-tetrahydrobenzo [c]thiophen-4-one mp 70° C.

¹H NMR (360 MHz, d₆-DMSO) δ 1.00 (6H, s), 2,37 (2H, s), 3.01 (1H, dd, J=12.1 and 7.7 Hz), 3.25 (1H, dd, J=12.2 and 4.3 Hz), 3.38 (1H, dd, J=11.1 and 5.9 Hz), 3.45–351 (3H, m). 6.48 (1H, d, J=2.3 Hz), 7.82 (1H, d, J=2.3 Hz). MS (ES⁺) 353 (M+1).

EXAMPLE 82

6,6-Dimethyl-3-((2-hydroxypropyl)thio)-1-(pyrazol-3-yl)-4,5,6,7-tetrahydrobenzo [c]thiophen-4-one mp 175–178° C. Found: C, 53.03; H, 6.12; N, 7.57%. $C_{16}H_{20}N_2O_2S_2.1.4$ ($H_2O$) requires: C, 53.13; H, 6.35; N, 7.75%.

¹H NMR (360 MHz, d₆-DMSO) δ 0.99 (3H, s), 1.00 (3H, s), 1.21 (3H, d, J=6.2 Hz), 2.37 (2H, s), 3.07 (2H, d, J=5.9 Hz), 3.97 (1H, q, J=6.1 Hz), 6.49 (1H, d, J=2.3 Hz), 7.83 (1H, br s). MS (ES⁺) 337 (M+1).

EXAMPLE 83

6,6-Dimethyl-3-(((N-methylaminocarbonyl)methyl)thio)-1-(pyrazol-3-yl)-4,5,6,7-tetrahydrobenzo [c]thiophen-4-one mp 180° C.

¹H NMR (360 MHz, d₆-DMSO) δ 1.00 (6H, s), 2.38 (2H, s), 2.60–2.64 (3H, m), 2.83 (2H, s), 3.99 (2H, s), 6.48 (1H, d, J=2.3 Hz), 7.83 (1H, d, J=2.4 Hz), 8.20–8.28 (1H, m). MS (ES⁺) 350 (M+1).

EXAMPLE 84

6.6-Dimethyl-1-(pyrazol-3-yl)-3-((pyrid-4-yl)thio-4,5,6,7-tetrahydrobenzo [c]thiophen-4-one mp 190° C. Found: C, 58.44; H, 4.65; N, 10.98%. $C_{18}H_{17}N_3OS_2.0.75$ ($H_2O$) requires: C, 58.59; H, 5.05; N, 11.39%.

¹NMR (360 MHz, d₆-DMSO) δ 1.03 (6H, s), 2.45 (2H, s), 2.90 (2H, s), 6.53 (1H, d, J=2.3 Hz), 7.50–7.52 (2H, m), 7.84 (1H, d, J=2.3 Hz), 8.58–8.60 (2H, m). MS (ES⁺) 356 (M+1).

EXAMPLE 85

6,6-Dimethyl-1-(pyrazol-3-yl)-3-((pyrimidin-2-yl)thio)-4,5,6,7-tetrahydrobenzo [c]thiophen-4-one mp 245° C. Found: C, 56.64; H, 4.40; N, 15.07%. $C_{17}H_{16}N_4OS_2.0.5$ ($H_2O$) requires: C, 55.87; H, 4.69; N, 15.33%.

¹H NMR (360 MHz, d₆-DMSO) δ 1.03 (6H, s), 2.45 (2H, s), 2.91 (2H, s), 6.56 (1H, d, J=2.3 Hz), 7.39 (1H, t, J=4.9 Hz), 7.88 (1H, br s), 8.78 (2H, d, J=4.9 Hz), 13.08 (1H, br s). MS (ES³⁰) 357 (M+1).

EXAMPLE 86

6,6-Dimethyl-1-(pyrazol-3-yl)-3-((thiazol-2-yl)thio)-4,5,6,7-tetrahydrobenzo [c]thiophen-4-one mp 195–198° C. Found: C, 52.89; H, 3.82; N, 11.30%. $C_{16}H_{15}N_4OS$, requires: C, 53.16; H, 4.18: N, 11.62%.

¹H NMR (360 MHz, d₆-DMSO) δ 1.03 (6H, s), 2.47 (2H, s), 2.87 (2H, s), 6.48–6.50 (1H, m), 7.83–7.85 (1H, m), 8.04–8.08 (2H, m), 13.03 (1H, br s). MS (ES⁺) 362 (M+1).

EXAMPLE 87

6,6-Dimethyl-3-(prop-2-enylthio)-1-(pyrazol-3-yl)-4,5,6,7-tetrahydrobenzo [c]thiophen-4-one mp. 164–167° C. Found: C, 59.80; H, 5.67; N, 8.43%. $C_{16}H_{18}N_2OS_2.0.1$ ($H_2O$) requires: C, 60.10; H, 5.73; N, .875%. ¹H NMR (360 MHz, CDCl₃) δ 1.07 (6H, s), 2.43 (2H, s), 2.85 (2H, s), 3.71–3.75 (2H, m), 5.23–5.27 (1H, m), 5.83–5.44 (1H, m), 5.93–6.05 (1H, m), 6.48 (1H, d, J=2.5 Hz), 7.65 (1H, d, J=2.4 Hz). MS (ES⁺) 319 (M+1).

EXAMPLE 88

6,6-Dimethyl-1-(pyrazol-3-yl)-3-((pyrid-2-yl)thio)-4,5,6,7-tetrahydrobenzo [c]thiophen-4-one mp. 207–209° C. Found: C, 60.75; H, 4.69; N, 11.49%. $C_{18}H_{17}N_3OS_2$ requires: C, 60.82; H, 4.82; N, 11.82%. ¹H NMR (360 MHz, CDCl$_3$) δ 1.09 (6H, s), 2.47 (2H, s), 2.89 (2H, s), 6.49 (1H, d, J=2.3 Hz), 7.19–7.23 (1H, m), 7.50 (1H, d, J=8.0 Hz), 7.63–7.69 (2H, m), 8.60–8.64 (1H, m). MS (ES$^+$) 356 (M+1).

EXAMPLE 89

6,6-Dimethyl-3-ethylthio-1-(pyrazol-3-yl)-4,5,6,7-tetrahydrobenzo [c]thiophen-4-one mp. 182–184° C. Found: C, 58.41; H, 5.79; N, 8.95%. C$_{15}$H$_{18}$N$_2$OS$_2$ requires: C, 58.79; H, 5.92; N, 9.14%. $^1$H NMR (360 MHz, CDCl$_3$) δ 1.07 (6H, s), 1.48 (3H, t, J=7.4 Hz), 2.43 (2H, s), 2.85 (2H, s), 3.10 (2H, q, J=7.3 Hz), 6.49 (1H, br s), 7.65 (1H, d, J=2.3 Hz). MS (ES$^+$) 307 (M+1).

EXAMPLE 90

6,6-Dimethyl-3-phenylthio-1-(pyrazol-3-yl)-4,5,6,7-tetrahydrobenzo [c]thiophen-4-one mp. 231–234° C. Found: C, 62.36; H, 5.07; N, 7.46%. C$_{19}$H$_{18}$OS$_2$.0.6 (H$_2$O) requires: C, 62.47; H, 5.30; N, 7.67%. $^1$H NMR (360 MHz, CDCl$_3$) δ 1.09 (6H, s), 2.47 (2H, s), 2.83 (2H, s), 6.38 (1H, br s), 7.43–7.47 (3H, m), 7.55 (1H, d, J=2.3 Hz), 7.69–7.73 (2H, m). MS (ES$^+$) 355 (M+1).

EXAMPLE 91

6,6-Dimethyl-3-((N,N-dimethyl-2-aminoethyl)thio)-1-(pyrazol-3-yl)-4,5,6,7-tetrahydrobenzo [c]thiophen-4-one mp. 212–214° C. Found: C, 58.03; H, 6.41; N, 11.58%. C$_{17}$H$_{23}$N$_3$OS$_2$.0.1 (H$_2$O) requires: C, 58.12; H, 6.66; N, 11.96%. $^1$H NMR (360 MHz, CDCl$_3$) δ 1.07 (6H, s), 2.32 (6H, s), 2.42 (2H, s), 2.75 (2H, t, J=7.6 Hz), 2.85 (2H, s), 3.20 (2H, t, J=7.5 Hz), 6.47 (1H, d, J=2.5 Hz), 7.63 (1H, d, J=2.5 Hz). MS (ES$^+$) 350 (M+1).

EXAMPLE 92

6,6-Dimethyl-3-[(2-hydroxyethyl)thio]-1-(pyrazol-3-yl)-4,5,6,7-tetrahydrobenzo [c]thiophen-4-one mp. 182–185° C. Found: C, 54.74; H, 5.74; N, 8.22%. C$_{15}$H$_{18}$N$_2$O$_2$S$_2$.0.4 (H$_2$O) requires: C, 54.65; H, 5.75; N, 8.50%. $^1$H NMR (360 MHz, d$_6$-DMSO) δ 1.00 (6H, s) 2.37 (2H, s), 2.83 (2H, s), 3.16 (2H, t, J=9.2 Hz), 3.70–3.80 (2H, m), 5.14 (1H, br m), 6.49 (1H, d, J=3.3 Hz), 7.84 (1H, br s), 13.04 (1H, br s). MS (ES$^+$) 323 (M+1).

EXAMPLE 93

6,6-Dimethyl-3-[(2-hydroxypropyl)thio]-1-(pyrazol-3-yl)-4,5,6,7-tetrahydrobenzo [c]thiophen-4-one mp. 172–175° C. Found: C, 56.96; H, 5.88; N, 8.34%. C$_{16}$H$_{20}$N$_2$O$_2$S$_2$ requires: C, 57.11; H, 5.99; N, 8.33%. $^1$H NMR (360 MHz, d$_6$-DMSO) δ 1.00 (6H, s), 1.83–1.92 (2H, m), 2.37 (2H, s), 2.84 (2H, s), 3.09 (2H, t, J=7.2 Hz), 3.51–3.56 (2H, m), 4.66 (1H, t, J=5.3 Hz), 6.49 (1H, br s), 7.84 (1H, br s), 13.00 (1H, br s). MS (ES$^+$) 337 (M+1).

EXAMPLE 94

6,6-Dimethyl-3-[(2-methoxyethyl)thio]-1-(pyrazol-3-yl)-4,5,6,7-tetrahydrobenzo [c]thiophen-4-one mp. 159–162° C. Found: C, 56.64; H, 5.80; N, 8.44%. C$_{10}$H$_{20}$N$_2$O$_2$S$_2$.0.2 (H$_2$O) requires: C, 56.51; H, 6.05; N, 8.24%. $^1$H NMR (360 MHz, CDCl$_3$) δ 1.07 (6H, s), 2.43 (2H, s), 2.85 (2H, s), 3.29 (2H, t, J=6.5 Hz), 3.41 (3H, s), 3.77 (2H, t, J=6.6 Hz), 6.49 (2H, d, J=2.2 Hz), 7.66 (2H, d, J=2.4 Hz). MS (ES$^+$) 337 (M+1).

EXAMPLE 95

6,6-Dimethyl-1-(isoxazol-5-yl)-3-methylthio-4,5,6,7-tetrahydrobenzo [c]thiophen-4-one Step 1: 6,6-Dimethyl-1-(3-hydroxy-1-oxoprop-2-enyl)-3-methylthio-4,5,6,7-tetrahydrobenzo [c]thiophen-4-one To a suspension of sodium hydride (149 mg of a 60% dispersion in oil. 3.7 mmol) in THF (7 mL) was added ethyl formate (0.75 mL, 9.3 mmol) at 0° C., under nitrogen. After addition a solution of 1-acetyl-6,6-dimethyl-3-methylthio-4,5,6,7-tetrahydrobenzo [c]thiophen-4-one (0.5 g, 1.9 mmol) in THF (7 mL) was added. The mixture was stirred overnight at room temperature. Methanol (0.5 mL) and water (0.5 mL) were then added to the mixture and the solvent removed in vacuo. The residue was dissolved in water and acidified using 1M HCl. The resultant solid was collected by filtration then partitioned between EtOAc (30 mL) and water (30 mL). The organic layer was separated, dried (Na$_2$SO$_4$) and evaporated. The residue was triturated with ether and the title compound (0.4 g, 80%) was isolated as a yellow solid. $^1$H NMR (360 MHz, CDCl$_3$) δ 1.09 (6H, s), 2.43 (2H, s), 2.63 (3H, s), 3.08 (2H, s), 5.85 (1H, d, J=5.1 Hz), 7.77 (1H, d, J=5.1 Hz), 14.90 (1H, br s). MS (ES$^+$) 297 (M+1).

Step 2: 6,6-Dimethyl-1-(isoxazol-5-yl)-3-methylthio-4,5,6,7-tetrahydrobenzo [c]thiophen-4-one A solution of 6,6-dimethyl-1-(3-hydroxy-1-oxoprop-2-enyl)-3-methylthio-4,5,6,7-tetrahydrobenzo [c]thiophen-4-one (200 mg, 0.68 mmol) in ethanol (14 mL) and water (1.6 mL) was heated to 80° C., after which hydroxylamine hydrochloride (52 mg, 0.74 mmol) was added. The mixture was heated at reflux for 4 h, after which time the solvent was removed in vacuo and the residue triturated in hexane/ether. The isoxazole (50 mg, 20%) was isolated as a colourless solid. mp 143–145° C. $^1$H NMR (360 MHz, CDCl$_3$) δ 1.09 (6H, s), 2.45 (2H, s), 2.64 (3H, s), 2.90 (2H, s), 6.28 (1H, d, J=1.9 Hz), 8.29 (1H, d, J=1.9 Hz). MS (ES$^+$) 294 (M+1).

EXAMPLE 96

7,7-Dimethyl-3-methylthio-1-(thiazol-2-yl)-4,5,6,7-tetrahydrobenzo [c]thiophen-4-one Step 1: 1-Cyano 7,7-dimethyl-3-methylthio-4,5,6,7-tetrahydrobenzo [c]thiophen-4-one In the same way as described in Example 37, Step 1, using 4,4-dimethylcyclohexan-1,3-dione the title compound (0.2 g, 5%) was isolated as a colourless solid. $^1$H NMR (250 MHz, CDCl$_3$) δ 1.55 (6H, s), 1.95 (2H, t, J=6.4 Hz), 2.60 (3H, s), 2.63 (2H, t, J=6.4 Hz).

Step 2: 7,7-Dimethyl-3-methylthio-4-oxo-4,5,6,7-tetrahydrobenzo [c]thiophene-1-thiocarboxamide In the same way as described in Example 6, Step 2, using 1-cyano 7,7-dimethyl-3-methylthio-4,5,6,7-tetrahydrobenzo [c]thiophen-4-one, the title compound (170 mg, 61%) was isolated as a yellow solid. $^1$H NMR (250 MHz, CDCl$_3$) δ

1.56 (6H, s), 1.89 (2H, t, J=6.8 Hz), 2.56 (3H, s), 2.61 (2H, t, J=6.8 Hz), 6.98 (1H, br s), 7.70 (1H, br s). MS (ES$^+$) 286 (M+1).

Step 3: 7,7-Dimethyl-3-methylthio-1-(thiazol-2-yl)-4,5,6,7-tetrahydrobenzo [c]thiophen-4-one In the same way as described in Example 6, Step 3, using 7,7-dimethyl-3-methylthio-4-oxo-4,5,6,7-tetrahydrobenzo [c]thiophene-1-thiocarboxamide, the title compound (90 mg, 50%) was isolated as a colourless solid. mp 188–190° C. Found: C, 52.56; H, 4.85; N, 4.28%. $C_{14}H_{15}NOS_3.0.5$ ($H_2O$) requires: C, 52.80; H, 5.06; N, 4.40%. $^1$H NMR (360 MHz, CDCl$_3$) δ 1.38 (6H, s), 1.89 (2H, t, J=6.5 Hz), 2.58 (3H, s), 2.63 (2H, t, J=6.5 Hz), 7.45 (1H, d, J=3.4 Hz), 7.89 (1H, d, J=3.4 Hz). MS (ES$^{30}$) 310 (M+1).

The following process was used to prepare Examples 97–105.

To a suspension of 6,6-dimethyl-3-methanesulphinyl-1-(pyrazol-3-yl)-4,5,6,7-tetrahydrobenzo [c]thiophen-4-one (50 mg, 0.16 mmol) in butanol (1mL) was added the appropriate amine (3.25 mmol). The mixture was heated at 100° C. for 24 h. The mixture was then diluted with MeOH:H$_2$O (1:1) and poured onto a C-18 Bond Elut cartridge (prewashed with MeOH followed by H$_2$O). The cartridge was eluted with MeOH:H$_2$O (10 mL) (1:1→1:0) and the product fractions evaporated. The residue was triturated with Et$_2$O to give the appropriate amino compound as a solid.

EXAMPLE 97

3-(Benzylamino)-6,6-dimethyl-1-(pyrazol-3-yl)-4,5,6,7-tetrahydrobenzo [c]thiophen-4-one mp 204–206° C. Found: C, 67.74; H, 5.92; N, 11.45%. $C_{20}H_{21}N_3OS.0.25$ ($H_2O$) requires: C, 67.48; H, 6.09; N, 11.80%.

$^1$H NMR (360 MHz, d$_6$-DMSO) δ 0.99 (6H, s), 2.26 (2H, s), 2.68 (2H, s), 4.50 (2H, d, J=6.1 Hz), 6.34 (1H, br s), 7.24–7.40 (5H, m), 7.74 (1H, br s), 9.08–9.14 (1H, br m), 12.73 (1H, br s). MS (ES$^+$) 352 (M+1).

EXAMPLE 98

6,6-Dimethyl-3-((furan-2-ylmethyl)amino)-1-(pyrazol-3-yl)-4,5,6,7-tetrahydrobenzo [c]thiophen-4-one mp 204–206° C. Found: C, 62.54; H, 5.36; N, 11.69%. $C_{18}H_{19}N_2O_2S.0.35$ ($H_2O$) requires: C, 62.17; H, 5.71; N, 12.08%.

$^1$H NMR (360 MHz, d$_6$-DMSO) δ 0.98 (6H, s), 2.25 (2H, s), 2.68 (2H, s), 4.50 (2H, d, J=6.1 Hz), 6.36 (1H, br s), 6.40–6.45 (2H, m), 7.63 (1H, s), 7.76 (1H, br s), 8.90–8.95 (1h, br m), 12.76 (1H, br s). MS (ES$^+$) 342 (M+1).

EXAMPLE 99

6,6-Dimethyl-3-((2-methylpropyl)amino)-1-(pyrazol-3-yl)-4,5,6,7-tetrahydrobenzo [c]thiophen-4-one mp 208–210° C. Found: C, 63.78; H, 7.21; N, 12.85%. $C_{17}H_{23}N_3OS.0.2$ ($H_2O$) requires: C, 63.60; H, 7.35; N, 13.09%.

$^1$H NMR (360 MHz, d$_6$-DMSO) δ 0.94 (6H, d, J=6.7 Hz), 0.99 (6H, s), 1.92–2.02 (1H, m), 2.24 (2H, s), 2.68 (2H, s), 3.10 (2H, t, J=6.5 Hz), 6.37 (1H, br s), 7.76 (1H, br s), 8.72–8.78 (1H, br m), 12.76 (1H, br s). MS (ES$^+$) 318 (M+1).

EXAMPLE 100

6,6-Dimethyl-3-(propylamino)-1-(pyrazol3-yl)-4,5,6,7-tetrahydrobenzo [c]thiophen-4-one mp 171–173° C.

$^1$H NMR (360 MHz, d$_6$-DMSO) δ 0.93 (3 H, t, J=7.4 Hz), 0.99 (6 H, s) 1.60–1.70 (2 H, m), 2.24 (2 H, s), 2.68 (2 H, s), 3.19–3.26 (2 H, m), 6.36 (1 H, br s), 7.76 (1 H, br s), 8.64–8.70 (1 H, br m), 12.76 (1 H, br s). MS (ES$^+$) 304 (M+1).

EXAMPLE 101

6,6-Dimethyl-3-((3-imidazol-1-ylpropyl)amino)-1-(pyrazol-3-yl)-4,5,6,7-tetrahydrobenzo[c]thiophen-4-one mp 85° C. Found: C, 59.49; H, 6.53; N, 18.45%. $C_{19}H_{23}N_5OS.0.7$ ($H_2O$) requires: C, 59.72; H, 6.44; N, 18.33%.

$^1$H NMR (360 MHz, d$_6$-DMSO) δ 0.99 (6 H, s), 2.06–2.16 (2 H, m), 2.24 (2 H, s), 2.68 (2 H, s), 3.18–3.26 (2 H, m), 4.05 (2 H, t, J=7.0 Hz), 6.36 (1 H, br s), 6.90 (1 H, s), 7.20 (1 H, s), 7.64 (1 H, s), 7.75 (1 H, br s), 8.62–8.68 (1 H, br m), 12.77 (1 H, br s). MS (ES$^+$) 370 (M+1).

EXAMPLE 102

6,6-Dimethyl-3-((2-methoxyethyl)amino)-1-(pyrazol-3-yl)-4,5,6,7-tetrahydrobenzo[c]thiophen-4-one mp 171–173° C. Found: C, 59.19; H, 6.60; N, 12.49%. $C_{16}H_{21}N_3OS.0.4$ ($H_2O$) requires: C, 58.84; H, 6.73; N, 12.86%

$^1$H NMR (360 MHz, d$_6$-DMSO) δ 0.99 (6 H, s) 2.24 (2 H, m), 2.69 (2 H, s), 3.30 (3 H, m), 3.38–3.44 (2 H, m), 3.57 (2 H, t, J=5.3 Hz), 6.37 (1 H, br s), 7.76 (1 H, br s), 8.64–8.68 (1 H, br m), 12.77 (1 H, br s), MS (ES$^+$) 320 (M+1).

EXAMPLE 103

3-Cyclopropylamino-6,6-dimethyl-1-(pyrazol-3-yl)-4,5,6,7-tetrahydrobenzo[c]thiophen-4-one mp 232–235° C. Found: C, 62.35; H, 6.24; N, 13.20%. $C_{16}H_{19}N_3OS.0.45$ ($H_2O$) requires: C, 62.09; H, 6.48; N, 13.58%.

$^1$H NMR (360 MHz, d$_6$-DMSO) δ 0.68–0.72 (2 H, m), 0.78–0.84 (2 H, m), 0.98 (6 H, s), 2.23 (2 H, s), 2.64–2.72 (3 H, m), 6.38 (1 H, br s), 7.76 (1 H, br s), 8.54 (1 H, br s), 12.77 (1 H, br s). MS (ES$^+$) 302 (M+1).

EXAMPLE 104

6,6-Dimethyl-3-((pyrid-2-yl)methylamino)-1-(pyrazol-3-yl)-4,5,6,7-tetrahydrobenzo[c]thiophen-4-one mp 210–213° C. found: C, 62.98; H, 5.49; N, 15.45%. $C_{19}H_{20}N_4OS.0.5$ ($H_2O$) requires: C, 63.13; H, 5.86, N, 15.50%.

$^1$H NMR (360 MHz, d$_6$-DMSO) δ 1.00 (6 H, s), 2.27 (2 H, s), 2.70 (2 H, s), 4.60 (2 H, d, J=5.8 Hz), 6.35 (1 H, s), 7.30–7.34 (1 H, m), 7.39–7.42 (1 H, m), 7.75 (1 H, br s), 7.78–7.83 (1 H, m), 8.56–8.60 (1 H, m), 9.26–9.32 (1 H, br m), 12.75 (1 H, br s), MS (ES$^+$) 353 (M+1).

EXAMPLE 105

6,6-Dimethyl-3-([3-(4-methylpiperazin-1-yl)propyl]amino)-1-(pyrazol-3-yl)-4,5,6,7-tetrahydrobenzo[c]thiophen-4-one mp 160–163° C. Found: C, 62.29; H, 8.14; N, 17.26%. $C_{21}H_{31}N_5OS.0.25$ ($H_2O$) requires: C, 62.11; H, 7.82; N, 17.25%

¹H NMR (360 MHz, d₆-DMSO) δ 0.98 (6 H, s) 1.74–1.82 (2 H, m), 2.15 (3 H, s), 2.23 (2 H, s), 2.28–2.40 (10 H, m), 2.68 (2 H, s), 3.26–3.32 (2 H, m), 6.36 (1 H, br s), 7.74 (1 H, br s), 8.70–8.76 (1 H, br s), 12.76 (1 H, br s). MS (ES⁺) 402 (M+1).

EXAMPLE 106

6,6-Dimethyl-3-methylamino-1-(pyrazol-3-yl)-4,5,6,7-tetrahydrobenzo[c]thiophen-4-one In the same way as in Example 50 using methylamine, the title compound (92 mg, 89%) was isolated as an orange solid. mp 240–243° C. Found: C, 59.88; H, 6.22; N, 14.67%. $C_{14}H_{17}N_3OS$ .0.3($H_2O$) requires: C, 59.89; H, 6.32; N, 14.97%. ¹H NMR (360 MHz, CDCl₃) δ 1.06 (6 H, s), 2.32 (2 H, s), 2.72 (2 H, s), 3.06 (3 H, d, J=5.2 Hz), 6.41 (1 H, br s), 7.60 (1 H, d, J=2.3 Hz). 8.58 (1 H, br s). MS (ES⁺) 276 (M+1).

EXAMPLE 107

6,6-Dimethyl-3-isopropylamino-1-(pyrazol-3-yl)-4,5,6,7-tetrahydrobenzo[c]thiophen-4-one In the same way as in Example 50 using isopropylamine, the title compound (57 mg, 58%) was isolated as an orange solid. mp 215–218° C. Found: C, 63.09; H, 6.67; N, 13.65% $C_{16}H_{21}N_3OS$ requires: C, 63.34; H, 6.98; N, 13.85%. ¹H NMR (360 MHz, CDCl₃) δ 1.06 (6 H, s). 1.35 (6 H, d, J=6.3 Hz), 2.32 (2 H, s), 2.71 (2 H, s), 3.50–3.60 (1 H, m), 6.40 (1 H, d, J=2.2 Hz), 7.60 (1 H, d, J=2.4 Hz), 8.64–8.70 (1 H, br m). MS (ES⁺) 304 (M+1).

EXAMPLE 108

6,6-Dimethyl-3-ethylamino-1-(pyrazol-3-yl)-4,5,6,7-tetrahydrobenzo[c]thiophen-4-one In the same way as in Example 50 using ethylamine, the title compound (66 mg, 70%) was isolated as a pale yellow solid. mp 237–240° C. Found: C, 61.16; H, 6.46; N, 14.02%. $C_{15}H_{19}N_3OS$ .0.3($H_2O$) requires: C, 61.11; H, 6.70; N, 14.25%. ¹H NMR (360 MHz, CDCl₃) δ 1.06 (6 H, s), 1.36 (3 H, t, J=7.2 Hz), 2.32 (2 H, s), 2.72 (2 H, s), 3.30–3.38 (2 H, m), 6.41 (1 H, br s), 7.59 (1 H, br s), 8.58–8.66 (1 H, br m). MS (ES⁺) 290 (M+1).

EXAMPLE 109

6,6-Dimethyl-3-((2-hydroxyethyl)amino)-1-(pyrazol-3-yl)-4,5,6,7-tetrahydrobenzo[c]thiophen-4-one In the same way as in Example 50 using ethanolamine, the title compound (57 mg, 58%) was isolated as a pale yellow solid. mp 227–230° C. Found: C, 58.18; H, 6.20; N, 13.24%. $C_{15}H_{19}N_3OS$ .0.25($H_2O$) requires: C, 58.14; H, 6.34; N, 13.56%. ¹H NMR (360 MHz, d₆-DMSO) δ 0.99 (6 H, s), 2.24 (2 H, s), 2.68 (2 H, s), 3.28–3.34 (2 H, m), 3.60–3.65 (2 H, m), 6.36 (1 H, d, J=2.2 Hz), 7.74 (1 H, d, J=2.3 Hz), 8.66–8.76 (1 H, m). MS (ES⁺) 306 (M+1).

EXAMPLE 110

3-Cyclobutylamino-6,6-dimethyl-1-(pyrazol-3-yl)-4,5,6,7-tetrahydrobenzo[c]thiophen-4-one In the same way as in Example 50 using cyclobutylamine, the title compound (57 mg, 56%) was isolated as a pale yellow solid. mp 207–209° C. Found: C, 62.90; H, 6.42; N, 12.70%. $C_{17}H_{21}N_3OS$ .0.45($H_2O$) requires: C, 63.11; H, 6.82; N, 12.99%. ¹H NMR (360 MHz, CDCl₃) δ 1.05 (6 H, s), 1.76–1.96 (2 H, m), 2.02–2.26 (2 H, m), 2.32 (2 H, s), 2.44–2.54 (2 H, m), 2.71 (2 H, s), 3.86–2.96 (1 H, m), 6.40 (1 H, d, J=2.3 Hz), 7.62 (1 H, d, J=2.3 Hz). MS (ES⁺) 316 (M+1).

EXAMPLE 111

3-(Azetidin-1-yl)-6,6-dimethyl-1-(pyrazol-3-yl)-4,5,6,7-tetrahydrobenzo[c]thiophen-4-one In the same way as in Example 50 using zaetidine, the title compound (62 mg, 63%) was isolated as a yellow solid. mp 263–265° C. Found: C, 63.47; H, 6.35; N, 13.42%. $C_{16}H_{19}N_3OS$ .0.15($H_2O$) requires: C, 63.19; H, 6.40; N, 13.82%. ¹H NMR (360 MHz, CDCl₃) δ 1.04 (6 H, s), 2.31 (2 H, s), 2.36–2.45 (2 H, m), 2.74 (2 H, br s), 4.16–4.32 (4 H, m), 6.41 (1 H, br s), 7.62 (1 H, d, J=2.2 Hz). MS (ES⁺) 302 (M+1).

EXAMPLE 112

6,6-Dimethyl-3-isopropoxy-1-(pyrazol-3-yl)-4,5,6,7-tetrahydrobenzo[c]thiophen-4-one In the same way as in Example 24 using sodium isopropoxide in isopropanol and 6,6-dimethyl-3-methanesulphonyl-1-(pyrazol-3-yl)-4,5,6,7-tetrahydrobenzo[c]thiophen-4-one, the title compound (40 mg, 43%) was isolated as a yellow solid. mp 196–198° C. Found: C, 61.64; H, 6.44; N, 8.81%; $C_{16}H_{20}N_2O_2S$ .0.4 ($H_2O$) requires: C, 61.67; H, 6.73; N, 8.99%. ¹H NMR (360 MHz, CDCl₃) δ 1.06 (6 H, s), 1.51 (6 H, d, J=6.1 Hz), 2.36 (2 H, s), 2.80 (2 H, s), 4.54–4.62 (1 H, m), 6.45 (1 H, br s), 7.62 (1 H, d, J=2.3 Hz). MS (ES⁺) 305 (M+1).

EXAMPLE 113

3-Methylthio-1-(pyrid-3-yl)-4,5,6,7-tetrahydrobenzo[c]thiophen-4-one

In the same way as in Example 33 using 1-bromo-3-methylthio-4,5,6,7-tetrahydrobenzo[c]thiophen-4-one and 3-pyridyl boronic acid, the title compound (62 mg, 62%) was obtained as a pale yellow solid. mp 130–132° C. Found: C, 61.26; H, 4.49; N, 4.85%. $C_{14}H_{13}NOS_2$ requires: C, 61.06; H, 4.76; N, 5.09% ¹H NMR (360 MHz, CDCl₃) δ 2.00–2.08 (2 H, m), 2.56–2.62 (2 H, m), 2.63 (3 H, s), 2.88–2.94 (2 H, m), 7.36–7.40 (1 H, m), 7.72–7.76 (1 H, m), 8.54–8.76 (2 H, br m). MS (ES⁺) 276 (M+1).

EXAMPLE 114

3-Methylthio-1-(pyrid-4-yl)-4,5,6,7-tetrahydrobenzo[c]thiophen-4-one

In the same way as in Example 33 using 1-bromo-3-methylthio-4,5,6,7-tetrahydrobenzo[c]thiophen-4-one and 4-pyridyl boronic acid, the title compound (24 mg, 24%) was obtained as a yellow solid. mp 112–114° C. Found: C, 60.08; H, 4.35; N, 5.16%. $C_{14}H_{13}NOS_2$ .0.15($H_2O$) requires: C, 60.47; H, 48.82; N, 5.04%. MS (ES⁺) 276 (M+1).

EXAMPLE 115

6,6-Dimethyl-3-methylthio-1-(2-methyl-1,3,4-oxadiazol-5-yl)-4,5,6,7-tetrahydrobenzo[c]thiophen-4-one Step 1: 6,6-Dimethyl-3-methylthio-4,5,6,7-tetrahydrobenzo[c]thiophen-4-one-1-carboxylic acid hydrazide To a suspension of 6,6-dimethyl-3-methylthio-4,5,6,7-tetrahydrobenzo[c]thiophen-4-one-1-carboxylic acid methyl ester (0.5 g, 1.8 mmol) in MeOH (10 mL) was added hydrzine monohydrate (0.51 mL, 10.5 mmol). This mixture was heated at reflux for 5 h. The solvent was evaporated and the residue triturated with ether to give the title compound (0.40 g, 80%) as a bright yellow solid. mp 225–228° C. Found: C, 48.26; H, 5.71; N, 9.34%; $C_{12}H_{16}N_2O_2S_2$ .0.75 ($H_2O$) requires: C, 48.38; H, 5.92; N, 9.40%. $^1$H NMR (360 MHz, $CDCl_3$) δ 1.07 (6 H, s), 2.42 (2 H, s), 2.61 (3 H, s), 2.96 (2 H, s), 6.89 (1 H, br s). MS ($ES^+$) 285 (M+1).

Step 2: 6,6-Dimethyl-3-methylthio-4,5,6,7-tetrahydrobenzo[c]thiophen-4-one-1-carboxylic acid N'-acetyl hydrazide To a suspension of the hydrazide (0.1 g, 0.35 mmol) in anhydrous DCM (4 mL) was added acetic anhydride (1 mL). The mixture was stirred at room temperature for 30 min. The solvent was evaporated and the residue azeotroped with toluene (2×10 mL). The residue was chromatographed on silica gel, eluting with DCM:MeOH (19:1) to give the title compound (90 mg, 78%) as a pale yellow solid. mp. 133–135° C. Found: C, 51.20; H, 5.37; N, 8.34%. $C_{14}H_{18}N_2O_3S_2$ requires: C, 51.51; H, 5.56; N, 8.58%. $^1$H NMR (6 H, s), 2.14 (3 H, s), 2.41 (2 H, s), 2.60 (3 H, s), 2.99 (2 H, s), 8.44–8.52 (2 H, m). MS ($ES^+$) 327 (M+1).

Step 3: 6,6-Dimethyl-3-methylthio-1-(2-methyl-1,3,4-oxadiazol-5-yl)-4,5,6,7-tetrahydrobenzo[c]thiophen-4-one To a suspension of the hydrazide (62 mg, 0.2 mmol) in dry toluene (5 mL) was added thionyl chloride (19 μL, 0.26 mmol) and triethylamine (44 μL, 0.23 mmol). This mixture was heated at 90° C. for 1 h. The solvent was evaporated and the residue chromatographed on silica using EtOAC:DCM (1:9) as the eluent. The fractions containing the desired product were combined and evaporated and the residue triturated with ether. The title compound (39 mg, 64%) was isolated as a pale yellow solid. mp 186–188° C. Found: C, 53.96; H, 4.76; N, 8.95%. $C_{14}H_{16}N_2O_2S_2$ .0.1($H_2O$) requires: C, 54.20; H, 5.26; N, 9.03%. $^1$H NMR (360 MHz, $CDCl_3$) δ 1.10 (6 H, s), 2.45 (2 H, s), 2.61 (3 H, s) 2.65 (3 H, s), 3.07 (2 H, s). MS ($ES^+$) 309 (M+1).

EXAMPLE 116

6,6-Dimethyl-3-methylthio-1-(1,3,4-oxadiazol-5-yl)-4,5,6,7-tetrahydrobenzo[c]thiophen-4-one Step 1: 6,6-Dimethyl-3-methylthio-1-4,5,6,7-tetrahydrobenzo[c]thiophen-4-one-1-carboxylic acid N'-formyl hydrazide A solution of 6,6-dimethyl-3-methylthio-4,5,6,7-tetrahydrobenzo[c]thiophen-4-one-1-carboxylic acid hydrazide (0.1 g, 0.35 mmol) in formic acid (98%, 2 mL) was heated at reflux for 2 h. The solvent was evaporated and the residue azeotroped with toluene (2×10 mL). The residue was chromatographed on silica with DCM:MeOH (19:1→9:1). The fractions containing the desired product were combined and evaporated and the residue triturated with ether. The title compound (90 mg, 82%) was isolated as a yellow solid. mp 87–90° C. found: C, 49.33; H, 5.26; N, 8.37%. $C_{13}H_{16}N_2O_3S_2$ 0.4($H_2O$) .0.15($Et_2O$) requires: C, 49.39; H, 5.58; N, 8.47%. $^1$H NMR (360 MHz, $CDCl_3$) δ 1.07 (6 H, s), 2.42 (2 H, s), 2.60 (3 H, s), 3.00 (2 H, s), 8.23 (1 H, s), 8.44–8.50 (1 H, m), 8.54–8.60 (1 H, m). MS ($ES^+$) 313 (M+1).

Step 2: 6,6-Dimethyl-3-methylthio-1-(1,3,4-oxadiazol-5-yl)-4,5,6,7-tetrahydrobenzo[c]thiophen-4-one In the same way as Example 115, Step 3, the title compound (27 mg, 41%) was obtained as a yellow solid. mp 185–189° C. Found: C, 51.86; H, 4.65; N, 8.84%. $C_{13}H_{14}N_2O_2S_2$ 0.5($H_2O$) requires: C, 51.46; H, 4.98; N, 9.23% $^1$H NMR (360 MHz, $CDCl_3$) δ 1.11 (6 H, s), 2.46 (2 H, s), 2.66 (3 H, s), 3.11 (2 H, s), 8.41 (1 H, s). MS ($ES^+$) 295 (M+1).

The following compounds of formula I in which q is 1 and $R^2$ and $R^3$ are 6,6-dimethyl also form part of the present invention and can be made by the processes disclosed herein. They all have $K_i$ value of less than 100 nM as measured by the aforementioned test method.

| | A | B |
|---|---|---|
| 1. | methylthio | (2-methylthio)pyrimidin-4-yl |
| 2. | methylthio | 3-(N,N-dimethyl)propenonyl |
| 3. | methylthio | (4-bromo)pyrazol-3-yl |
| 4. | methylthio | [N-(4-chlorophenyl)aminocarbonyl]pyrazol-3-yl |
| 5. | methylthio | pyrazol-3-yl |
| 6. | methylthio | (4-ethoxycarbonyl)thiazol-2-yl |
| 7. | methylthio | [(N-phenyl)aminocarbonyl]pyrazol-3-yl |
| 8. | methylthio | (1-methylcarbonyl)pyrazol-3-yl |
| 9. | 4-chloro-benzylthio | 3-(N,N-dimethyl)propenonyl |
| 10. | methylthio | 2-[N-(4-chlorophenyl)aminocarbonylmethylthio]pyrimidin-4-yl |

What is claimed is:
1. A pharmaceutical composition comprising a compound of formula (I) or a pharmaceutically acceptable salt thereof:

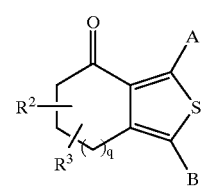

(I)

where A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^{14}$;

B is a 5-membered ring having one or two unsaturations containing 1, 2, 3 or 4 heteroatoms chosen from O, N and S provided that not more than one heteroatom is other than N, or a 6-membered aromatic ring containing 1, 2, 3 or 4 nitrogen atoms, which ring is optionally substituted by one or more substituents independently chosen from: $C_{1-6}$alkyl; $C_{1-6}$haloalkyl; halogen; $S(O)_pR^4$; $COR^5$; and aryl or aryl $C_{1-6}$alkyl wherein the aryl ring is optionally substituted by one, two or three substituents independently chosen from halogen, $CF_3$, $OCH_3$, nitro and cyano;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl $C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ is hydrogen, $C_{1-8}$alkyl, $C_{2-8}$alkenyl, $C_{2-8}$alkynyl, aryl or $CH_2(CO)_mNR^8R^9$;

$R^5$ is $NR^6R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{14}$ is hydrogen or $C_{1-6}$alkyl;

m is zero or 1;

p is zero, 1 or 2;

q is 1 or 2; and r is 0, 1 or 2;

and a pharmaceutically acceptable excipient.

2. A composition according to claim 1 in which:

A is $SR^1$;

B is a nitrogen containing aromatic ring which is 5-membered and contains 1, 2, 3 or 4 heteroatoms chosen from O, N and S provided that not more than one heteroatom is other than N, or is 6-membered and contains 1, 2, 3 or 4 nitrogen atoms, which ring is optionally substituted by $C_{1-6}$alkyl, halogen, $SR^4$, $COR^5$ or benzyl optionally substituted by one or two substituents independently chosen from halogen, nitro and cyano;

$R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio;

$R^2$ and $R^3$ are independently chosen from hydrogen and methyl;

$R^4$ is hydrogen, methyl or $CH_2CONR^8R^9$;

$R^5$ is methyl, methoxy, ethoxy or $NR^6R^7$;

$R^6$ is hydrogen or $C_{1-4}$alkyl;

$R^7$ is phenyl unsubstituted or substituted by halogen, nitro or cyano;

$R^8$ is hydrogen or $C_{1-6}$alkyl;

$R^9$ is $C_{1-6}$alkyl or phenyl optionally substituted by one or two substituents independently chosen from halogen or nitro;

$R^{14}$ is hydrogen or $C_{1-4}$alkyl;

p is zero; and q is 1.

3. A composition according to claim 1 in which the compound of formula I is 6,6-Dimethyl-1-(2-methyltetrazol-5-yl)-3-methylthio-4,5,6,7-tetrahydrobenzo[c]thiophen-4-one;

6,6-Dimethyl-3-methanesulphinyl-1-(pyrazol-3-yl)-4,5,6,7-tetrahydrobenzo[c]thiophen-4-one;

6,6-Dimethyl-3-ethyl-1-(pyrazol-3-yl)-4,5,6,7-tetrahydrobenzo[c]thiophen-4-one;

6,6-Dimethyl-3-methylthio-1-(2-propyltetrazol-5-yl)-4,5,6,7-tetrahydrobenzo[c]thiophen-4-one;

6,6-Dimethyl-1-(1-methanesulphonylpyrazol-3-yl)-3-methylthio-4,5,6,7-tetrahydrobenzo[c]thiophen-4-one;

6,6-Dimethyl-3-(2-methylprop-1-yl)-1-(thiazol-2-yl)-4,5,6,7-tetrahydrobenzo[c]thiophen-4-one;

6,6-Dimethyl-3-isopropyl-1-(thiazol-2-yl)-4,5,6,7-tetrahydrobenzo[c]thiophen-4-one;

6,6-Dimethyl-3-propyl-1-(thiazol-2-yl)-4,5,6,7-tetrahydrobenzo[c]thiophen-4-one;

6,6-Dimethyl-3-phenyl-1-(thiazol-2-yl)-4,5,6,7-tetrahydrobenzo[c]thiophen-4-one.

4. A compound of formula I or a pharmaceutically acceptable salt thereof

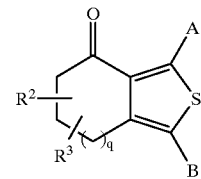

(I)

wherein A is $C_{1-6}$alkyl, $C_{2-6}$alkenyl, $C_{2-6}$alkynyl, $C_{3-6}$cycloalkyl, aryl$C_{1-6}$alkyl, aryl, $S(O)_pR^1$, $OR^1$ or $NR^1R^{14}$;

B is a 5-membered ring having one or two unsaturations containing 1, 2, 3 or 4 heteroatoms chosen from O, N and S provided that not more than one heteroatom is other than N, or a 6-membered aromatic ring containing 1, 2, 3 or 4 nitrogen atoms, which ring is optionally substituted by one or more substituents independently chosen from: $C_{1-6}$alkyl; $C_{1-6}$haloalkyl; halogen; $S(O)_r R^4$; $COR^5$; and aryl or aryl $C_{1-6}$alkyl wherein the aryl ring is optionally substituted by one, two or three substituents independently chosen from halogen, $CF_3$, $OCH_3$, nitro and cyano;

$R^1$ is hydrogen; $C_{1-6}$alkyl, $C_{2-6}$alkenyl, $C_{2-6}$alkynyl, $C_{3-6}$cycloalkyl or $C_{3-6}$cycloalkenyl each of which is optionally substituted by amino, $C_{1-6}$alkylamino, di($C_{1-6}$alkyl)amino, $C_{1-6}$alkoxy, $C_{1-6}$alkylaminocarbonyl, one, two or three hydroxy groups, one, two or three halogen atoms or a four, five or six-membered saturated heterocyclic ring containing a nitrogen atom and optionally either an oxygen atom or a further nitrogen atom which ring is optionally substituted by $C_{1-4}$alkyl on the further nitrogen atom; aryl, aryl$C_{1-6}$alkyl, aryl$C_{2-6}$alkenyl or aryl$C_{2-6}$alkynyl optionally substituted on the aryl ring by halogen, nitro, cyano, $C_{1-6}$alkylcarbonylamino, hydroxy or $C_{1-6}$alkoxy; or a five-membered aromatic ring containing 1, 2, 3 or 4 heteroatoms chosen from O, N and S provided that not more than one heteroatom is other than N, or a six-membered aromatic ring containing 1, 2, 3 or 4 nitrogen atoms, which ring is optionally substituted by halogen, $C_{1-6}$alkoxy, $C_{1-6}$alkylthio, aryl, $C_{1-6}$alkyl, $C_{2-6}$alkenyl or $C_{2-6}$alkynyl;

$R^2$ and $R^3$ are independently hydrogen or $C_{1-6}$alkyl or together with the carbon atom to which they are attached form a $C_{3-8}$cycloalkyl group;

$R^4$ is hydrogen, $C_{1-8}$alkyl, $C_{2-8}$alkenyl, $C_{2-8}$alkynyl, aryl or $CH_2(CO)_m NR^8 R^9$;

$R^5$ is $NR^6 R^7$, $C_{1-6}$alkyl or $C_{1-6}$alkoxy;

$R^6$ is independently as defined for $R^4$;

$R^7$ is aryl optionally substituted by halogen, nitro or cyano;

$R^8$ is hydrogen, $C_{1-6}$alkyl, $C_{3-6}$cycloalkyl, $C_{3-6}$cycloalkenyl, $C_{2-6}$alkenyl, $C_{2-6}$alkynyl; aryl$C_{1-6}$alkyl, aryl$C_{2-6}$alkenyl or aryl$C_{2-6}$alkynyl optionally substituted on the aryl ring by halogen, nitro or cyano; thiophene or pyridine;

$R^9$ is $C_{1-6}$alkyl; $C_{2-6}$alkenyl; $C_{2-6}$alkynyl; or phenyl optionally substituted by one, two or three substituents independently chosen from halogen, $CF_3$, $OCH_3$, nitro and cyano;

$R^{14}$ is hydrogen or $C_{1-6}$alkyl;

m is zero or 1;

p is zero, 1 or 2;

q is 1 or 2; and r is 0, 1 or 2.

5. A method of treatment of a condition associated with GABA$_A$ receptors containing the α5 subunit which comprises administering to a subject suffering from or prone to such a condition a therapeutically effective amount of a compound of formula I as defined in claim 1 or a pharmaceutically acceptable salt thereof.

6. The compound of claim 4 wherein

A is $SR^1$;

B is a nitrogen containing aromatic ring which is 5-membered and contains 1, 2, 3 or 4 heteroatoms chosen from O, N and S provided that not more than one heteroatom is other than N, or is 6-membered and contains 1, 2, 3 or 4 nitrogen atoms, which ring is optionally substituted by $C_{1-6}$alkyl, halogen, $SR^4$, $COR^5$ or benzyl optionally substituted by one or two substituents independently chosen from halogen, nitro and cyano;

$R^1$ is $C_{1-6}$alkyl, $C_{1-4}$alkenyl, or $C_{3-6}$cycloalkyl each of which is optionally substituted by di($C_{1-4}$alkyl)amino, $C_{1-4}$alkoxy, $C_{1-4}$alkylaminocarbonyl, one or two hydroxy groups or three fluorine atoms; phenyl or phenyl$C_{1-4}$alkyl optionally substituted on the phenyl ring by chlorine, fluorine, $C_{1-4}$alkoxy or $C_{1-4}$alkylcarbonylamino; or a pyridine, thiophene, furan, pyrimidine, thiazole, imidazole, triazole or thiadiazole, each of which is unsubstituted or substituted by $C_{1-4}$alkyl, phenyl, fluorine or $C_{1-4}$alkylthio;

$R^2$ and $R^3$ are independently chosen from hydrogen and methyl;

$R^4$ is hydrogen, methyl or $CH_2 CONR^8 R^9$;

$R^5$ is methyl, methoxy, ethoxy or $NR^6 R^7$;

$R^6$ is hydrogen or $C_{1-4}$alkyl;

$R^7$ is phenyl unsubstituted or substituted by halogen, nitro or cyano;

$R^8$ is hydrogen or $C_{1-6}$alkyl;

$R^9$ is $C_{1-6}$alkyl or phenyl optionally substituted by one or two substituents independently chosen from halogen or nitro;

$R^{14}$ is hydrogen or $C_{1-4}$alkyl;

p is zero; and q is 1.

7. The compound of claim 4 in which the compound of formula I is 6,6-Dimethyl-1-(2-methyltetrazol-5-yl)-3-methylthio-4,5,6,7-tetrahydrobenzo[c]thiophen-4-one;

6,6-Dimethyl-3-methanesulphinyl-1-(pyrazol-3-yl)-4,5,6,7-tetrahydrobenzo[c]thiophen-4-one;

6,6-Dimethyl-3-ethyl-1-(pyrazol-3-yl)-4,5,6,7-tetrahydrobenzo[c]thiophen-4-one;

6,6-Dimethyl-3-methylthio-1-(2-propyltetrazol-5-yl)-4,5,6,7-tetrahydrobenzo[c]thiophen-4-one;

6,6-Dimethyl-1-(1-methanesulphonylpyrazol-3-yl)-3-methylthio-4,5,6,7-tetrahydrobenzo[c]thiophen-4-one;

6,6-Dimethyl-3-(2-methylprop-1-yl)-1-(thiazol-2-yl)-4,5,6,7-tetrahydrobenzo[c]thiophen-4-one;

6,6-Dimethyl-3-isopropyl-1-(thiazol-2-yl)-4,5,6,7-tetrahydrobenzo[c]thiophen-4-one;

6,6-Dimethyl-3-propyl-1-(thiazol-2-yl)-4,5,6,7-tetrahydrobenzo[c]thiophen-4-one;

6,6-Dimethyl-3-phenyl-1-(thiazol-2-yl)-4,5,6,7-tetrahydrobenzo[c]thiophen-4-one;

3-Cyclohexyl-6,6-dimethyl-1-(thiazol-2-yl)-4,5,6,7-tetrahydrobenzo[c]thiophen-4-one;

3-Cyclobutyl-6,6-dimethyl-1-(thiazol-2-yl)-4,5,6,7-tetrahydrobenzo[c]thiophen-4-one;

3-(But-3-enyl)-6,6-dimethyl-1-(thiazol-2-yl)-4,5,6,7-tetrahydrobenzo[c]thiophen-4-one;

3-Cyclopropyl-6,6-dimethyl-1-(thiazol-2-yl)-4,5,6,7-tetrahydrobenzo[c]thiophen-4-one;

6,6-Dimethyl-3-(2-methylprop-1-enyl)-1-(thiazol-2-yl)-4,5,6,7-tetrahydrobenzo[c]thiophen-4-one;

3-Methylthio-1-(pyrid-2-yl)-4,5,6,7-tetrahydrobenzo[c]thiophen-4-one;

6,6-Dimethyl-3-methanesulphonyl-1-(pyrazol-3-yl)-4,5,6,7-tetrahydrobenzo[c]thiophen-4-one;

1-(Thiazol-2-yl)-3,6,6-trimethyl-4,5,6,7-tetrahydrobenzo[c]thiophen-4-one;

3-Benzyl-6,6-dimethyl-1-(thiazol-2-yl)-4,5,6,7-tetrahydrobenzo[c]thiophen-4-one;

6,6-Dimethyl-3-methylthio-1-((1-phenylsulphonyl)pyrazol-3-yl)-4,5,6,7-tetrahydrobenzo[c]thiophen-4-one;

6,6-Dimethyl-3-isopropylthio-1-(2-methyltetrazol-5-yl)-4,5,6,7-tetrahydrobenzo[c]thiophen-4-one;

1-(1-Acetylpyrazol-3-yl)-6,6-dimethyl-3-methanesulphinyl-4,5,6,7-tetrahydrobenzo[c]thiophen-4-one;

6,6-Dimethyl-3-[(2-hydroxyethyl)thio]-1-(thiazol-2-yl)-4,5,6,7-tetrahydrobenzo[c]thiophen-4-one;

6,6-Dimethyl-3-[(1,1-dimethylethyl)thio]-1-(pyrazol-3-yl)-4,5,6,7-tetrahydrobenzo[c]thiophen-4-one;

6,6-Dimethyl-3-methoxy-1-(pyrazol-3-yl)-4,5,6,7-tetrahydrobenzo[c]thiophen-4-one;

6,6-Dimethyl-1-(4-methyl-1,2,4-triazol-3-yl)-3-methylthio-4,5,6,7-tetrahydrobenzo[c]thiophen-4-one;

6,6-Dimethyl-1-((4-ethoxycarbonyl)thiazol-2yl)-3-methylthio-4,5,6,7-tetrahydrobenzo[c]thiophen-4-one;

6,6-Dimethyl-1-((4-trifluoromethyl)thiazol-2-yl)-3-methylthio-4,5,6,7-tetrahydrobenzo[c]thiophen-4-one;

6,6-Dimethyl-3-methylthio-1-(thiazol-2-yl)-4,5,6,7-tetrahydrobenzo[c]thiophen-4-one;

6,6-Dimethyl-3-dimethylamino-1-((4-ethoxycarbonyl)thiazol-2-yl)-4,5,6,7-tetrahydrobenzo[c]thiophen-4-one;

1-((4-Acetyl)thiazol-2-yl)-6,6-dimethyl-3-methylthio-4,5,6,7-tetrahydrobenzo[c]thiophen-4-one;

6,6-Dimethyl-1-((4-methyl)thiazol-2-yl)-3-methylthio-4,5,6,7-tetrahydrobenzo[c]thiophen-4-one;

6,6-Dimethyl-3-isopropylthio-1-(thiazol-2-yl)-4,5,6,7-tetrahydrobenzo[c]thiophen-4-one;

6,6-Dimethyl-3-methylthio-1-(pyrazol-4-yl)-4,5,6,7-tetrahydrobenzo[c]thiophen-4-one;

6,6-Dimethyl-3-methylthio-1-(pyrrol-2-yl)-4,5,6,7-tetrahydrobenzo[c]thiophen-4-one;

6,6-Dimethyl-3-methylthio-1-(pyrid-2-yl)-4,5,6,7-tetrahydrobenzo[c]thiophen-4-one;

6,6-Dimethyl-3-((2-hydroxyethyl)thio)-1-(pyrid-2-yl)-4,5,6,7-tetrahydrobenzo[c]thiophen-4-one;

3-Methylthio-1-(thiazol-2-yl)-4-oxo-5,6,7,8-tetrahydro-4H-cyclohepta[c]thiophen;

6,6-Dimethyl-3-methylthio-1-(3-methyl-1,2,4-oxadiazol-5-yl)-4,5,6,7-tetrahydrobenzo[c]thiophen-4-one;

6,6-Dimethyl-3-methylthio-1-(3-isopropyl-1,2,4-oxadiazol-5-yl)-4,5,6,7-tetrahydrobenzo[c]thiophen-4-one;

6,6-Dimethyl-1-(4-benzyl-1,2,4-triazol-3-yl)-3-methylthio-4,5,6,7-tetrahydrobenzo[c]thiophen-4-one;

6,6-Dimethyl-3-methylthio-1-(1-methyl-1,2,4-triazol-3-yl)-4,5,6,7-tetrahydrobenzo[c]thiophen-4-one;

6,6-Dimethyl-3-methylthio-1-(oxazolidin-2-yl)-4,5,6,7-tetrahydrobenzo[c]thiophen-4-one;

3-Methylthio-1-(oxazol-2-yl)-4,5,6,7-tetrahydrobenzo[c]thiophen-4-one;

6,6-Dimethyl-3-methylthio-1-(pyrazin-2-yl)-4,5,6,7-tetrahydrobenzo[c]thiophen-4-one;

6,6-Dimethyl-3-methylthio-1-(pyrimidin-5-yl)-4,5,6,7-tetrahydrobenzo[c]thiophen-4-one;

6,6-Dimethyl-1-(imidazolin-2-yl)-3-methylthio-4,5,6,7-tetrahydrobenzo[c]thiophen-4-one;

3-Methylthio-6,6-spirocyclohexyl-1-(thiazol-2-yl)-4,5,6,7-tetrahydrobenzo[c]thiophen-4-one;

6,6-Dimethyl-1-(3-(N-methylaminocarbonyl)thiazol-2-yl)-3-methylthio-4,5,6,7-tetrahydrobenzo[c]thiophen-4-one;

6,6-Dimethyl-3-methylthio-1-(thiazol-5-yl)-4,5,6,7-tetrahydrobenzo[c]thiophen-4-one;

6,6-Dimethyl-3-tert-butylamino)-1-(pyrazol-3-yl)-4,5,6,7-tetrahydrobenzo[c]thiophen-4-one;

3-Cyclobutoxy-6,6-dimethyl-1-(pyrazol-3-yl)-4,5,6,7-tetrahydrobenzo[c]thiophen-4-one;

6,6-Dimethyl-1-[(3-ethoxycarbonyl)isoxazol-5-yl)-3-methylthio-4,5,6,7-tetrahydrobenzo[c]thiophen-4-one;

6,6-Dimethyl-3-phenoxy-1-(pyrazol-3-yl)-4,5,6,7-tetrahydrobenzo[c]thiophen-4-one;

6,6-Dimethyl-3-pentylthio-1-(pyrazol-3-yl)-4,5,6,7-tetrahydrobenzo[c]thiophen-4-one;

3-Butylthio-6,6-dimethyl-1-(pyrazol-3-yl)-4,5,6,7-tetrahydrobenzo[c]thiophen-4-one;

3-[(3-Chloropropyl)thio]-6,6-dimethyl-1-(pyrazol-3-yl)-4,5,6,7-tetrahydrobenzo[c]thiophen-4-one;

6,6-Dimethyl-3-((2-phenylethyl)thio)-1-(pyrazol-3-yl)-4,5,6,7-tetrahydrobenzo[c]thiophen-4-one;

6,6-Dimethyl-3-propylthio-1-(pyrazol-3-yl)-4,5,6,7-tetrahydrobenzo[c]thiophen-4-one;

6,6-Dimethyl-3-((2-methylbutyl)thio)-1-(pyrazol-3-yl)-4,5,6,7-tetrahydrobenzo[c]thiophen-4-one;

6,6-Dimethyl-1-(pyrazol-3-yl)-3-((2,2,2-trifluoroethyl)thio)-4,5,6,7-tetrahydrobenzo[c]thiophen-4-one;

6,6-Dimethyl-3-((1-methylpropyl)thio)-1-(pyrazol-3-yl)-4,5,6,7-tetrahydrobenzo[c]thiophen-4-one;

3-((4-Chlorophenyl)thio)-6,6-dimethyl-1-(pyrazol-3-yl)-4,5,6,7-tetrahydrobenzo[c]thiophen-4-one;

6,6-Dimethyl-3-((3-fluorophenyl)thio)-1-(pyrazol-3-yl)-4,5,6,7-tetrahydrobenzo[c]thiophen-4-one;

3-((4-Acetylaminophenyl)thio)-6,6-dimethyl-1-pyrazol-3-yl)-4,5,6,7-tetrahydrobenzo[c]thiophen-4-one;

6,6-Dimethyl-3-((4-methoxyphenyl)thio)-1-(pyrazol-3-yl)-4,5,6,7-tetrahydrobenzo[c]thiophen-4-one;

6,6-Dimethyl-3-((1-methylimidazol-2-yl)thio)-1-(pyrazol-3-yl)-4,5,6,7-tetrahydrobenzo[c]thiophen-4-one;

6,6-Dimethyl-3-((thiophen-2-yl)thio)-1-(pyrazol-3-yl)-4,5,6,7-tetrahydrobenzo[c]thiophen-4-one;

6,6-Dimethyl-3-((imidazol-2-yl)thio)-1-(pyrazol-3-yl)-4,5,6,7-tetrahydrobenzo[c]thiophen-4-one;

6,6-Dimethyl-3-((4-phenylthiazol-2-yl)thio)-1-(pyrazol-3-yl)-4,5,6,7-tetrahydrobenzo[c]thiophen-4-one;

6,6-Dimethyl-1-(pyrazol-3-yl)-3-((1,2,4-triazol-3-yl)thio)-4,5,6,7-tetrahydrobenzo[c]thiophen-4-one;

6,6-Dimethyl-3-((5-methyl-1,3,4-thiadiazol-2-yl)thio)-1-(pyrazol-3-yl)-4,5,6,7-tetrahydrobenzo[c]thiophen-4-one;

6,6-Dimethyl-3-((4-methyl-1,2,4-triazol-3-yl)thio)-1-(pyrazol-3-yl)-4,5,6,7-tetrahydrobenzo[c]thiophen-4-one;

6,6-Dimethyl-3-((5-methylthio-1,3,4-thiadiazol-2-yl)thio)-1-(pyrazol-3-yl)-4,5,6,7-tetrahydrobenzo[c]thiophen-4-one;

3-Benzylthio-6,6-dimethyl-1-(pyrazol-3-yl)-4,5,6,7-tetrahydrobenzo[c]thiophen-4-one;

3-Cyclopentylthio-6,6-dimethyl-1-(pyrazol-3-yl)-4,5,6,7-tetrahydrobenzo[c]thiophen-4-one;

6,6-Dimethyl-3-((2-methylpropyl)thio)-1-(pyrazol-3-yl)-4,5,6,7-tetrahydrobenzo[c]thiophen-4-one;

6,6-Dimethyl-3-hexylthio-1-(pyrazol-3-yl)-4,5,6,7-tetrahydrobenzo[c]thiophen-4-one;

6,6-Dimethyl-3-isopropylthio-1-(pyrazol-3-yl)-4,5,6,7-tetrahydrobenzo[c]thiophen-4-one;

6,6-Dimethyl-3-((furan-2-ylmethyl)thio)-1-(pyrazol-3-yl)-4,5,6,7-tetrahydrobenzo[c]thiophen-4-one;

6,6-Dimethyl-3-((2-hydroxy-1-methylpropyl)thio)-1-(pyrazol-3-yl)-4,5,6,7-tetrahydrobenzo[c]thiophen-4-one;

6,6-Dimethyl-3-((2,3-dihydroxypropyl)thio)-1-(pyrazol-3-yl)-4,5,6,7-tetrahydrobenzo[c]thiophen-4-one;

6,6-Dimethyl-3-((2-hydroxypropyl)thio)-1-(pyrazol-3-yl)-4,5,6,7-tetrahydrobenzo[c]thiophen-4-one;

6,6-Dimethyl-3-(((N-methylaminocarbonyl)methyl)thio)-1-(pyrazol-3-yl)-4,5,6,7-tetrahydrobenzo[c]thiophen-4-one;

6,6-Dimethyl-1-(pyrazol-3-yl)-3-((pyrid-4-yl)thio)-4,5,6,7-tetrahydrobenzo[c]thiophen-4-one;

6,6-Dimethyl-1-(pyrazol-3-yl)-3-((pyrimidin-2-yl)thio)-4,5,6,7-tetrahydrobenzo[c]thiophen-4-one;

6,6-Dimethyl-1-(pyrazol-3-yl)-3-((thiazol-2-yl)thio)-4,5,6,7-tetrahydrobenzo[c]thiophen-4-one;

6,6-Dimethyl-3-(prop-2-enylthio)-1-(pyrazol-3-yl)-4,5,6,7-tetrahydrobenzo[c]thiophen-4-one;

6,6-Dimethyl-1-(pyrazol-3-yl)-3-((pyrid-2-yl)thio)-4,5,6,7-tetrahydrobenzo[c]thiophen-4-one;

6,6-Dimethyl-3-ethylthio-1-(pyrazol-3-yl)-4,5,6,7-tetrahydrobenzo[c]thiophen-4-one;

6,6-Dimethyl-3-phenylthio-1-(pyrazol-3-yl)-4,5,6,7-tetrahydrobenzo[c]thiophen-4-one;

6,6-Dimethyl-3-((N,N-dimethyl-2-aminoethyl)thio)-1-(pyrazol-3-yl)-4,5,6,7-tetrahydrobenzo[c]thiophen-4-one;

6,6-Dimethyl-3-[(2-hydroxyethyl)thio]-1-(pyrazol-3-yl)-4,5,6,7-tetrahydrobenzo[c]thiophen-4-one;

6,6-Dimethyl-3-[(2-hydroxypropyl)thio]-1-(pyrazol-3-yl)-4,5,6,7-tetrahydrobenzo[c]thiophen-4-one;

6,6-Dimethyl-3-[(2-methoxyethyl)thio]-1-(pyrazol-3-yl)-4,5,6,7-tetrahydrobenzo[c]thiophen-4-one;

6,6-Dimethyl-1-(isoxazol-5-yl)-3-methylthio-4,5,6,7-tetrahydrobenzo[c]thiophen-4-one;

7,7-Dimethyl-3-methylthio-1-(thiazol-2-yl)-4,5,6,7-tetrahydrobenzo[c]thiophen-4-one;

3-(Benzylamino)-6,6-dimethyl-1-(pyrazol-3-yl)-4,5,6,7-tetrahydrobenzo[c]thiophen-4-one;

6,6-Dimethyl-3-((furan-2-ylmethyl)amino)-1-(pyrazol-3-yl)-4,5,6,7-tetrahydrobenzo[c]thiophen-4-one;

6,6-Dimethyl-3-((2-methylpropyl)amino)-1-(pyrazol-3-yl)-4,5,6,7-tetrahydrobenzo[c]thiophen-4-one;

6,6-Dimethyl-3-(propylamino)-1-(pyrazol-3-yl)-4,5,6,7-tetrahydrobenzo[c]thiophen-4-one;

6,6-Dimethyl-3-((3-imidazol-1-ylpropyl)amino)-1-(pyrazol-3-yl)-4,5,6,7-tetrahydrobenzo[c]thiophen-4-one;

6,6-Dimethyl-3-((2-methoxyethyl)amino)-1-(pyrazol-3-yl)-4,5,6,7-tetrahydrobenzo[c]thiophen-4-one;

3-Cyclopropylamino-6,6-dimethyl-1-(pyrazol-3-yl)-4,5,6,7-tetrahydrobenzo[c]thiophen-4-one;

6,6-Dimethyl-3-((pyrid-2-yl)methylamino)-1-(pyrazol-3-yl)-4,5,6,7-tetrahydrobenzo[c]thiophen-4-one;

6,6-Dimethyl-3-([3-(4-methylpiperazin-1-yl)propyl]amino)-1-(pyrazol-3-yl)-4,5,6,7-tetrahydrobenzo[c]thiophen-4-one;

6,6-Dimethyl-3-methylamino-1-(pyrazol-3-yl)-4,5,6,7-tetrahydrobenzo[c]thiophen-4-one;

6,6-Dimethyl-3-isopropylamino-1-(pyrazol-3-yl)-4,5,6,7-tetrahydrobenzo[c]thiophen-4-one;

6,6-Dimethyl-3-ethylamino-1-(pyrazol-3-yl)-4,5,6,7-tetrahydrobenzo[c]thiophen-4-one;

6,6-Dimethyl-3-((2-hydroxyethyl)amino)-1-(pyrazol-3-yl)-4,5,6,7-tetrahydrobenzo[c]thiophen-4-one;

3-Cyclobutylamino-6,6-dimethyl-1-(pyrazol-3-yl)-4,5,6,7-tetrahydrobenzo[c]thiophen-4-one;

3-(Azetidin-1-yl)-6,6-dimethyl-1-(pyrazol-3-yl)-4,5,6,7-tetrahydrobenzo[c]thiophen-4-one;

6,6-Dimethyl-3-isopropoxy-1-(pyrazol-3-yl)-4,5,6,7-tetrahydrobenzo[c]thiophen-4-one;

3-Methylthio-1-(pyrid-3-yl)-4,5,6,7-tetrahydrobenzo[c]thiophen-4-one;

3-Methylthio-1-(pyrid-4-yl)-4,5,6,7-tetrahydrobenzo[c]thiophen-4-one;

6,6-Dimethyl-3-methylthio-1-(2-methyl-1,3,4-oxadiazol-5-yl)-4,5,6,7-tetrahydrobenzo[c]thiophen-4-one; or 6,6-Dimethyl-3-methylthio-1-(1,3,4-oxadiazol-5-yl)-4,5,6,7-tetrahydrobenzo[c]thiophen-4-one;

or a pharmaceutically acceptable salt thereof.

8. The compound of claim 4 wherein q is 1;

$R^2$ and $R^3$ are 6,6-dimethyl; and

A and B are chosen from the following pairings:

| | A | B |
|---|---|---|
| 1. | methylthio | (2-methylthio)pyrimidin-4-yl |
| 3. | methylthio | (4-bromo)pyrazol-3-yl |
| 4. | methylthio | {N-(4-chlorophenyl)aminocarbonyl}pyrazol-3-yl |
| 5. | methylthio | pyrazol-3-yl |
| 6. | methylthio | (4-ethoxycarbonyl)thiazol-2-yl |
| 7. | methylthio | {(N-phenyl)aminocarbonyl}pyrazol-3-yl |
| 8. | methylthio | (1-methylcarbonyl)pyrazol-3-yl |
| 10. | methylthio | 2-{N-(4-chlorophenyl)aminocarbonylmethylthio}pyrimidin-4-yl | or a pharmaceutically acceptable salt thereof.

9. A method of treatment of a condition associated with $GABA_A$ receptors containing the α5 subunit which comprises administering to a subject suffering from or prone to such a condition a therapeutically effective amount of a compound of formula I as defined in claim 6 or a pharmaceutically acceptable salt thereof.

10. A method of treatment of a condition associated with $GABA_A$ receptors containing the α5 subunit which comprises administering to a subject suffering from or prone to such a condition a therapeutically effective amount of a compound of formula I as defined in claim 7 or a pharmaceutically acceptable salt thereof.

11. A method of treatment of a condition associated with $GABA_A$ receptors containing the α5 subunit which comprises administering to a subject suffering from or prone to such a condition a therapeutically effective amount of a compound of formula I as defined in claim 8 or a pharmaceutically acceptable salt thereof.

12. The method of claim 5 wherein the condition associated with $GABA_A$ receptors containing the α5 subunit is Alzheimer's disease.

13. The method of claim 9 wherein the condition associated with $GABA_A$ receptors containing the α5 subunit is Alzheimer's disease.

14. The method of claim 10 wherein the condition associated with $GABA_A$ receptors containing the α5 subunit is Alzheimer's disease.

15. The method of claim 11 wherein the condition associated with $GABA_A$ receptors containing the α5 subunit is Alzheimer's disease.

* * * * *